United States Patent
Bates et al.

(10) Patent No.: US 10,717,710 B2
(45) Date of Patent: *Jul. 21, 2020

(54) SOLID FORMS OF SUBSTITUTED 5,6-DIHYDRO-6-PHENYLBENZO[F] ISOQUINOLIN-2-AMINE COMPOUNDS

(71) Applicant: ArQule, Inc., Burlington, MA (US)

(72) Inventors: Craig Bates, Pelham, NH (US); David P. Reed, Pelham, NH (US)

(73) Assignee: ArQule, Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/261,744

(22) Filed: Jan. 30, 2019

(65) Prior Publication Data

US 2020/0002293 A1 Jan. 2, 2020

Related U.S. Application Data

(63) Continuation of application No. 15/966,091, filed on Apr. 30, 2018, now Pat. No. 10,227,311, which is a continuation of application No. 15/381,414, filed on Dec. 16, 2016, now Pat. No. 9,981,921.

(60) Provisional application No. 62/268,747, filed on Dec. 17, 2015.

(51) Int. Cl.
*C07D 239/84* (2006.01)
*A61K 31/517* (2006.01)
*A61P 35/00* (2006.01)

(52) U.S. Cl.
CPC .......... *C07D 239/84* (2013.01); *A61K 31/517* (2013.01); *A61P 35/00* (2018.01); *C07B 2200/13* (2013.01); *Y02A 50/411* (2018.01)

(58) Field of Classification Search
CPC ............................ C07D 239/84; A61K 31/517
USPC .......................................... 544/249; 514/267
See application file for complete search history.

(56) References Cited

U.S. PATENT DOCUMENTS

| | | | |
|---|---|---|---|
| 6,133,257 A | 10/2000 | Batchelor et al. | |
| 8,357,694 B2 | 1/2013 | Ali et al. | |
| 9,981,921 B2 | 5/2018 | Bates et al. | |
| 10,093,632 B2 * | 10/2018 | Bates .................. | C07D 239/70 |
| 10,277,311 B2 | 3/2019 | Bates et al. | |
| 2015/0072959 A1 | 3/2015 | Goff et al. | |
| 2017/0174637 A1 | 6/2017 | Bates et al. | |

FOREIGN PATENT DOCUMENTS

| WO | WO 98/28281 A1 | 7/1998 |
|---|---|---|
| WO | WO 2010/078421 A1 | 7/2010 |
| WO | WO 2012/177852 A1 | 12/2012 |

\* cited by examiner

*Primary Examiner* — Venkataraman Balasubramanian
(74) *Attorney, Agent, or Firm* — Cooley LLP; Matthew Pavao; Chen Chen

(57) ABSTRACT

The present application provides solid forms of (R)-6-(2-fluorophenyl)-N-(3-(2-(2-methoxyethylamino)ethyl)phenyl)-5,6-dihydrobenzo[h]quinazolin-2-amine dihydrochloride, and methods of preparing and using same.

37 Claims, 41 Drawing Sheets

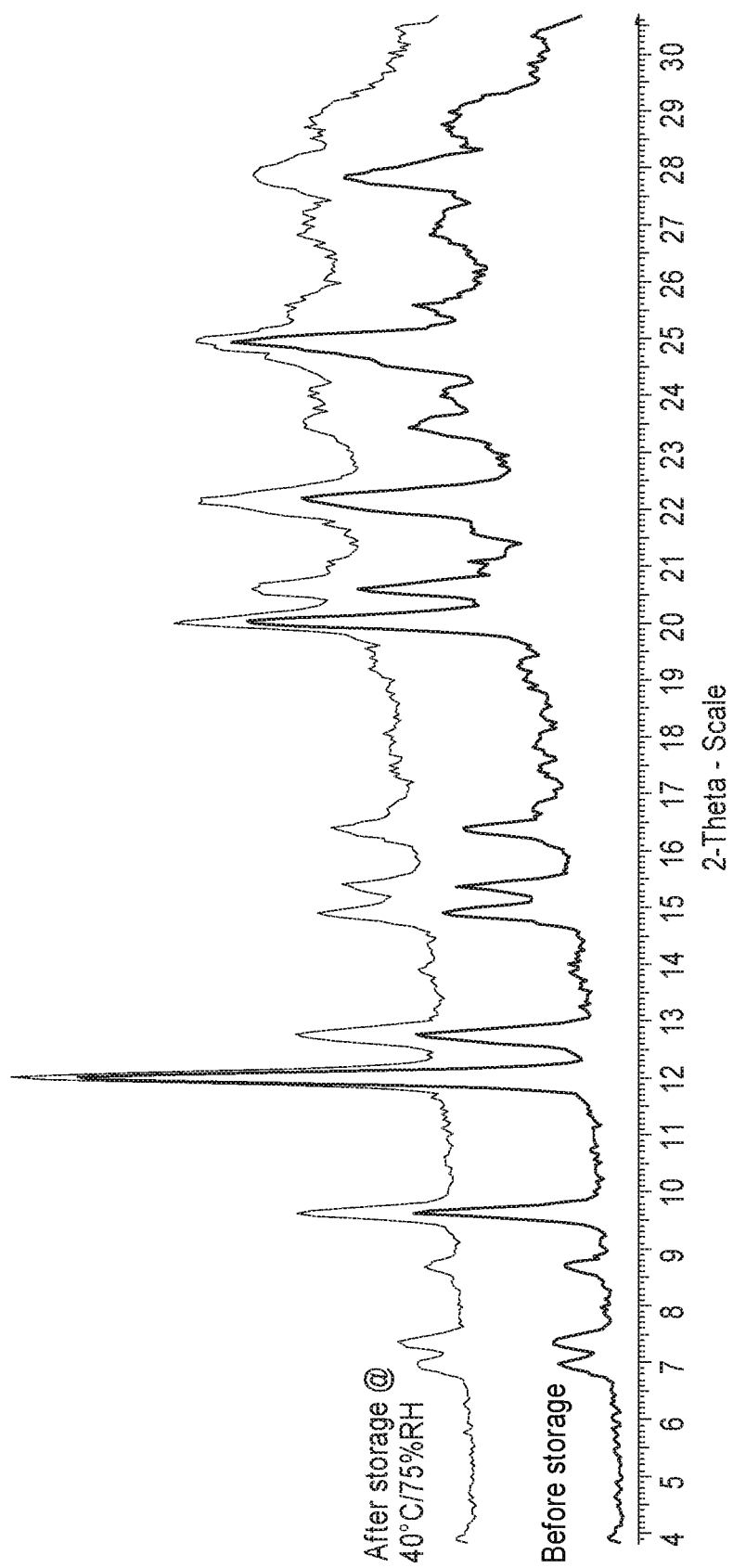

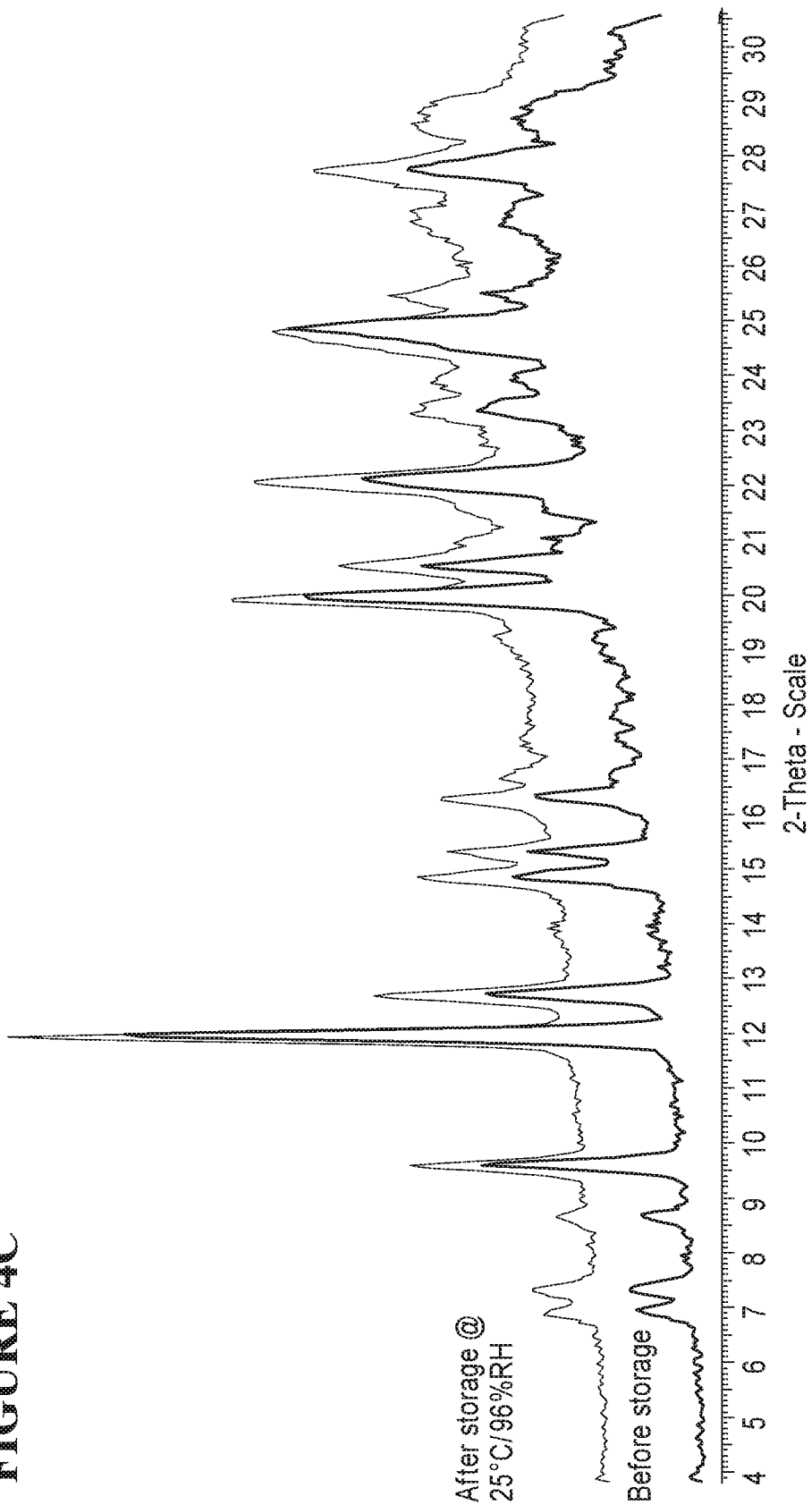

SOLID FORMS OF SUBSTITUTED 5,6-DIHYDRO-6-PHENYLBENZO[F] ISOQUINOLIN-2-AMINE COMPOUNDS

CROSS-REFERENCE TO RELATED APPLICATION

This application is a continuation of U.S. Ser. No. 15/966,091, filed on Apr. 30, 2018 (now allowed), which is a continuation of U.S. Ser. No. 15/381,414, filed on Dec. 16, 2016 (now U.S. Pat. No. 9,981,921), which claims priority to, and the benefit of, U.S. Ser. No. 62/268,747, filed on Dec. 17, 2015, the entire contents of each of which are incorporated herein by reference in their entireties.

BACKGROUND

Cancer is the second leading cause of death in the United States, exceeded only by heart disease. Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

Cancer cells are by definition heterogeneous. For example, within a single tissue or cell type, multiple mutational "mechanisms" may lead to the development of cancer. As such, heterogeneity frequently exists between cancer cells taken from tumors of the same tissue and same type that have originated in different individuals. Frequently observed mutational "mechanisms" associated with some cancers may differ between one tissue type and another (e.g., frequently observed mutational "mechanisms" leading to colon cancer may differ from frequently observed "mechanisms" leading to leukemias). It is therefore often difficult to predict whether a particular cancer will respond to a particular chemotherapeutic agent.

Components of cellular signal transduction pathways that regulate the growth and differentiation of normal cells can, when dysregulated, lead to the development of cellular proliferative disorders and cancer. Mutations in cellular signaling proteins may cause such proteins to become expressed or activated at inappropriate levels or at inappropriate times during the cell cycle, which in turn may lead to uncontrolled cellular growth or changes in cell-cell attachment properties. For example, dysregulation of receptor tyrosine kinases by mutation, gene rearrangement, gene amplification, and overexpression of both receptor and ligand has been implicated in the development and progression of cancers.

FGFR2 is a member of the fibroblast growth factor receptor family, where amino acid sequence is highly conserved between members and throughout evolution. FGFR family members differ from one another in their ligand affinities and tissue distribution. A full-length representative protein consists of an extracellular region, composed of three immunoglobulin-like domains, a single hydrophobic membrane-spanning segment, and a cytoplasmic tyrosine kinase domain. The extracellular portion of the protein interacts with fibroblast growth factors, setting downstream signals, ultimately influencing mitogenesis and differentiation.

Alterations in the activity (expression) of the FGFR2 gene are associated with certain cancers. The altered gene expression may enhance several cancer-related events such as cell proliferation, cell movement, and the development of new blood vessels that nourish a growing tumor. The FGFR2 gene is abnormally active (overexpressed) in certain types of stomach cancers, and this amplification is associated with a poorer prognosis and response to standard clinical methods. Abnormal expression of FGFR2 is also found in patients with prostate cancer. More than 60 percent of women with breast cancer in the United States carry at least a single mutation in this gene as well.

Accordingly, new compounds and methods for modulating FGFR2 and treating proliferation disorders, including cancer, are needed. The present application addresses these needs.

SUMMARY

The present application provides solid forms of (R)-6-(2-fluorophenyl)-N-(3-(2-(2-methoxyethylamino)ethyl)phenyl)-5,6-dihydrobenzo[h]quinazolin-2-amine dihydrochloride (Compound A) of the following structure:

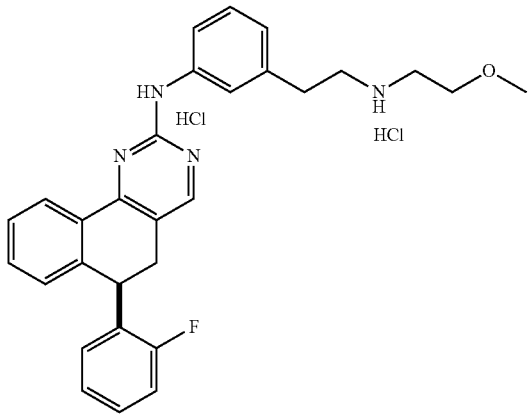 [SMILES: COCCNCCc1cccc(Nc2ncc3c(n2)-c2ccccc2[C@H](c2ccccc2F)C3)c1 ; Cl ; Cl]

In one embodiment, the present application provides an amorphous form of Compound A. In one embodiment, the amorphous form is characterized an X-ray powder diffraction pattern substantially similar to that set forth in FIG. 1. In one embodiment, the amorphous form is characterized by a glass transition temperature at approximately 102° C. In one embodiment, the amorphous form is characterized by an endothermic event with onset at approximately 98° C. as measured by DSC. In one embodiment, the amorphous form is characterized by a DSC thermogram substantially similar to that set forth in FIG. 2.

In one embodiment, the present application provides crystalline forms of Compound A. In one embodiment, the present application provides polymorphs of Compound A.

In one embodiment, the present application provides a Form A polymorph of Compound A characterized by an X-ray powder diffraction pattern comprising peaks at approximately 12.0, 14.8, and 20.8 °2θ using Cu Kα radiation. In one embodiment, the Form A polymorph is characterized by an X-ray powder diffraction pattern substantially similar to that set forth in FIG. 4A, 4B, or 4C.

In one embodiment, the present application provides a Form A polymorph of Compound A characterized by endothermic events with onset at between approximately 40° C. and approximately 49° C., between approximately 72° C. and approximately 74° C., and between approximately 143° C. and approximately 149° C. as measured by DTA or DSC.

In one embodiment, the Form A polymorph is characterized by a DTA thermogram substantially similar to that set forth in FIG. 6A or a DSC thermogram substantially similar to that set forth in FIG. 6B.

In one embodiment, the present application provides a Form E polymorph of Compound A characterized by an X-ray powder diffraction pattern comprising peaks at approximately 10.4, 12.4, and 23.7 °2θ using Cu Kα radiation. In one embodiment, the Form E polymorph is characterized by an X-ray powder diffraction pattern substantially similar to that set forth in FIG. 8.

In one embodiment, the present application provides a Form C polymorph of Compound A characterized by an X-ray powder diffraction pattern comprising peaks at approximately 8.9, 20.2, and 20.9 °2θ using Cu Kα radiation. In one embodiment, the Form C polymorph is characterized by an X-ray powder diffraction pattern substantially similar to that set forth in FIG. 10.

In one embodiment, the present application provides a Form C polymorph of Compound A characterized by an endothermic event with onset at approximately 152° C. as measured by DSC. In one embodiment, the Form C polymorph is characterized by a DSC thermogram substantially similar to that set forth in FIG. 11.

In one embodiment, the present application provides a Form D polymorph of Compound A characterized by an X-ray powder diffraction pattern comprising peaks at approximately 14.9, 23.1, and 23.8 °2θ using Cu Kα radiation. In one embodiment, the Form D polymorph is characterized by an X-ray powder diffraction pattern substantially similar to that set forth in FIG. 13A, 13B, or 13C.

In one embodiment, the present application provides a Form D polymorph of Compound A characterized by an endothermic event with onset between approximately 110° C. and approximately 123° C. as measured by DTA or DSC. In one embodiment, the Form D polymorph is characterized by a DTA thermogram substantially similar to that set forth in any one of FIGS. 16A, 16B, 16C, and 16D.

In one embodiment, the present application provides a Form F polymorph of Compound A characterized by an X-ray powder diffraction pattern comprising peaks at approximately 11.1, 17.9, and 28.2 °2θ using Cu Kα radiation. In one embodiment, the Form F polymorph is characterized by an X-ray powder diffraction pattern substantially similar to that set forth in FIG. 17A or 17B.

In one embodiment, the present application provides a Form F polymorph of Compound A characterized by endothermic events with onset at approximately 51° C. and approximately 133° C. as measured by DTA or DSC. In one embodiment, the Form F polymorph is characterized by a DTA thermogram substantially similar to that set forth in FIG. 18.

In one embodiment, the present application provides a Form G polymorph of Compound A characterized by an X-ray powder diffraction pattern comprising peaks at approximately 9.0, 9.6, and 24.2 °2θ using Cu Kα radiation. In one embodiment, the Form G polymorph is characterized by an X-ray powder diffraction pattern substantially similar to that set forth in FIG. 20A, 20B, or 20C.

In one embodiment, the present application provides a Form G polymorph of Compound A characterized by an endothermic event with onset between approximately 108° C. and approximately 125° C. as measured by DTA. In one embodiment, the Form G polymorph is characterized by a DTA thermogram substantially similar to that set forth in any one of FIGS. 21A, 21B, 21C, and 21D.

In one embodiment, the present application provides a Form B solid form of Compound A characterized by an X-ray powder diffraction pattern comprising peaks at approximately 5.2, 9.3, and 10.6 °2θ using Cu Kα radiation. In one embodiment, the Form B solid form is characterized by an X-ray powder diffraction pattern substantially similar to that set forth in FIG. 25. In one embodiment, the Form B solid form is partially crystalline and partially amorphous.

In one embodiment, the present application provides a Form B solid form of Compound A characterized by an endothermic event with onset at approximately 158° C. as measured by DSC. In one embodiment, the Form B solid form is characterized by a DSC thermogram substantially similar to that set forth in FIG. 26.

The present application also provides a pharmaceutical composition comprising any one of the solid forms of Compound A (e.g., any of Forms A, C, D, E, F, and G, solid Form B, and the amorphous form) as described herein, and a pharmaceutically acceptable carrier or excipient.

The present application also provides a method of treating a cell proliferative disorder, comprising administering, to a subject in need thereof, a therapeutically effective amount of a composition comprising any one of the solid forms of Compound A as described herein.

The present application also provides a solid form of Compound A as described herein for use in the manufacture of a medicament for treating a cell proliferative disorder in a subject in need thereof.

The present application also provides use of a solid form of Compound A as described herein in treating a cell proliferative disorder in a subject in need thereof.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the present application. In the case of conflict, the present specification, including definitions, will control. In addition, the materials, methods, and examples are illustrative only and are not intended to be limiting.

Other features and advantages of the disclosure will be apparent from the following detailed description and claims.

BRIEF DESCRIPTION OF THE FIGURES

FIG. 4B sets forth X-ray powder diffraction patterns of Form A before and after storage at 40° C. and 75% RH.

FIG. 4C sets forth X-ray powder diffraction patterns of Form A before and after storage at 25° C. and 96% RH.

DETAILED DESCRIPTION

Figure 1:
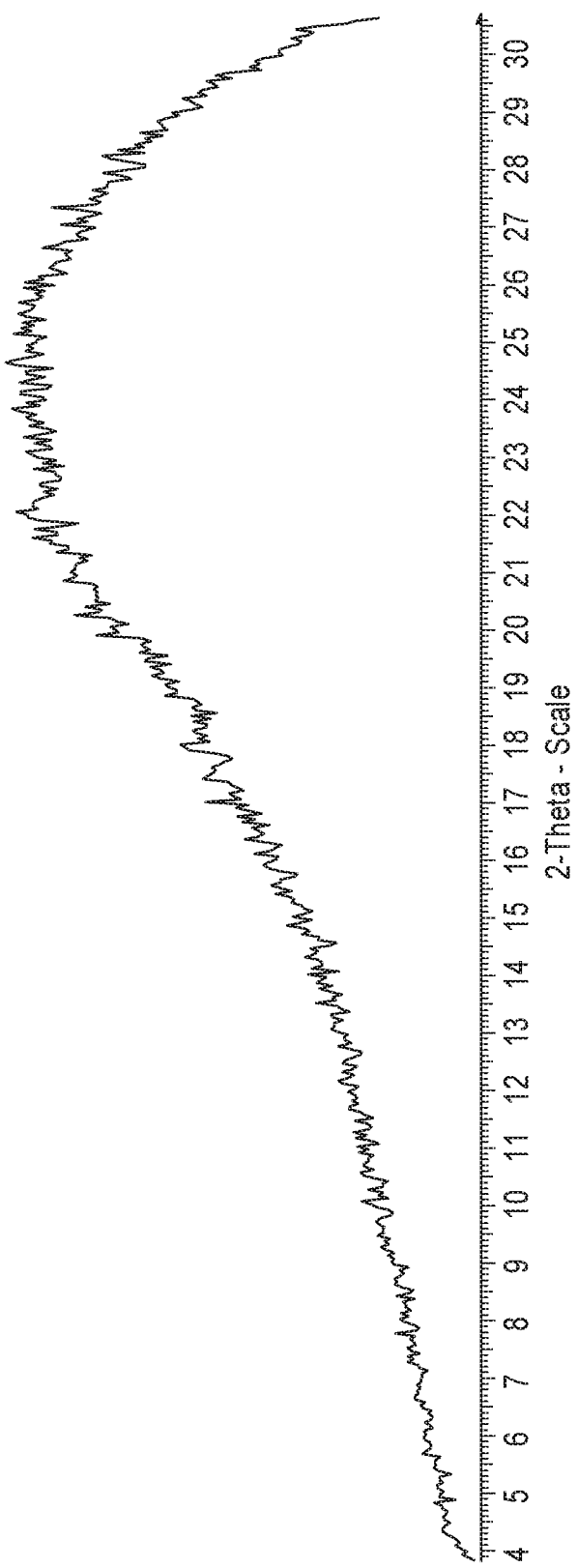
FIG. 1 sets forth an X-ray powder diffraction pattern of an amorphous form of Compound A.

Solid Forms
Amorphous Form

The present application provides solid forms of (R)-6-(2-fluorophenyl)-N-(3-(2-(2-methoxyethylamino)ethyl)phenyl)-5,6-dihydrobenzo[h]quinazolin-2-amine dihydrochloride (Compound A) of the following structure:

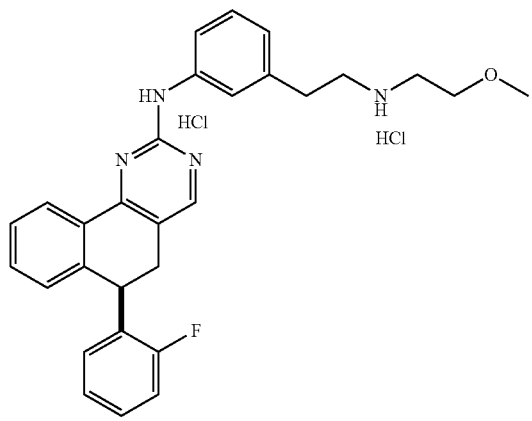 [SMILES: COCCNCCc1cccc(Nc2ncc3c(n2)-c2ccccc2[C@H](c2ccccc2F)C3)c1 ; Cl ; Cl]

In one embodiment, the present application provides an amorphous form of Compound A. In one embodiment, the amorphous form is characterized an X-ray powder diffraction pattern substantially similar to that set forth in FIG. 1. In one embodiment, the amorphous form is characterized by a glass transition temperature at approximately 102° C. In one embodiment, the amorphous form is characterized by an endothermic event with onset at approximately 98° C. as measured by DSC. In one embodiment, the amorphous form is characterized by a DSC thermogram substantially similar to that set forth in FIG. 2.

In one embodiment, the amorphous form is converted to the Form F polymorph of Compound A when stored at 40° C./75% RH.

Crystalline Forms

In one embodiment, the present application provides crystalline forms of Compound A. In one embodiment, the present application provides polymorphs of Compound A. In one embodiment, the crystalline form of Compound A is a solvate. In one embodiment, the crystalline form of Compound A is a hydrate. In one embodiment, the crystalline form of Compound A is a mono-hydrate. In one embodiment, the crystalline form of Compound A is a hemi-hydrate. In one embodiment, the crystalline form of Compound A is a DMSO solvate. In one embodiment, the crystalline form of Compound A is a mono-DMSO solvate. In one embodiment, the crystalline form of Compound A is a hemi-DMSO solvate.

Form A

In one embodiment, the present application provides a Form A polymorph of Compound A ("Form A") characterized by an X-ray powder diffraction pattern comprising peaks at approximately 12.0, 14.8, and 20.8 °2θ using Cu Kα radiation. In one embodiment, Form A is characterized by an X-ray powder diffraction pattern comprising peaks at approximately 7.0, 12.0, 14.8, 20.8, and 22.3 °2θ using Cu Kα radiation. In one embodiment, Form A is characterized by an X-ray powder diffraction pattern comprising peaks at approximately 3.9, 7.0, 7.3, 9.6, 12.0, 12.7, 14.8, 15.3, 20.8, 21.1, and 22.3 °2θ using Cu Kα radiation. In one embodiment, Form A is characterized by an X-ray powder diffraction pattern comprising peaks at approximately 3.9, 7.0, 7.3, 8.7, 9.6, 12.0, 12.7, 13.8, 14.8, 15.3, 20.2, 20.8, 21.1, 22.3, and 27.9 °2θ using Cu Kα radiation. In one embodiment, Form A is characterized by an X-ray powder diffraction pattern comprising peaks at approximately the positions shown in the table below:

| Peak List | | |
|---|---|---|
| Pos. [° 2θ] | Height [cts] | Rel. Int. [%] |
| 3.9412 | 200.55 | 28.31 |
| 6.9663 | 523.96 | 73.96 |
| 7.3452 | 478.55 | 67.55 |
| 8.6586 | 173.68 | 24.51 |
| 9.5546 | 508.46 | 71.77 |
| 11.9659 | 551.78 | 77.88 |
| 12.6976 | 383.86 | 54.18 |
| 13.8146 | 126.60 | 17.87 |
| 14.7909 | 684.31 | 96.59 |
| 15.2987 | 397.01 | 56.04 |
| 16.2613 | 102.84 | 14.52 |
| 16.6588 | 63.21 | 8.92 |
| 17.4470 | 23.20 | 3.28 |
| 20.1585 | 180.78 | 25.52 |
| 20.7539 | 708.46 | 100 |
| 21.1397 | 201.39 | 28.43 |
| 22.2583 | 532.01 | 75.09 |
| 24.0525 | 19.48 | 2.75 |
| 25.6131 | 46.96 | 6.63 |
| 27.8614 | 103.31 | 14.58 |
| 28.6483 | 86.71 | 12.24 |

Figure 4A:
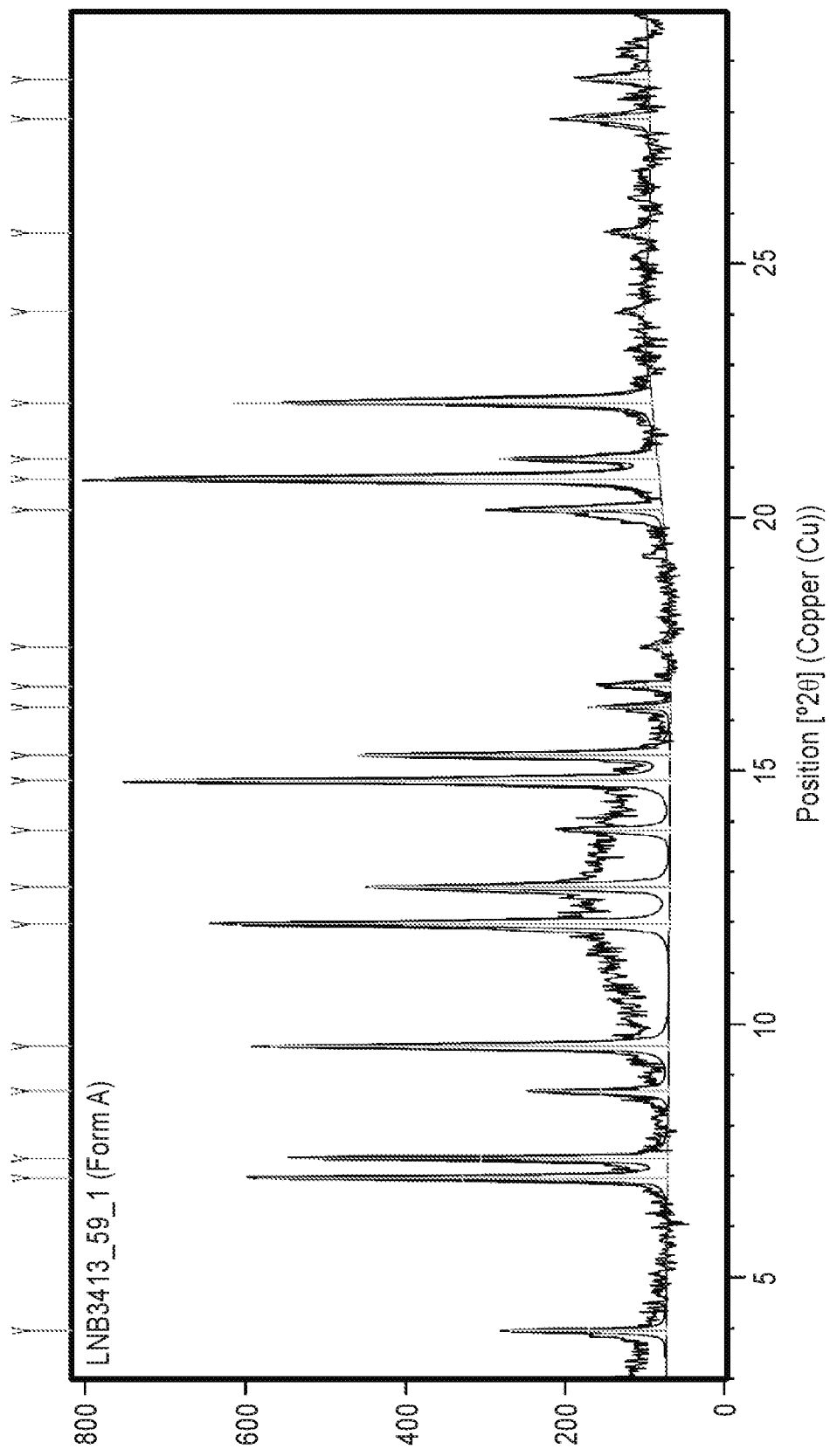
FIG. 4A sets forth an X-ray powder diffraction pattern of Form A.

In one embodiment, Form A is characterized by an X-ray powder diffraction pattern substantially similar to that set forth in FIG. 4A, 4B, or 4C. In one embodiment, Form A is characterized by an X-ray powder diffraction pattern substantially similar to that set forth in FIG. 4A.

Figure 6A:
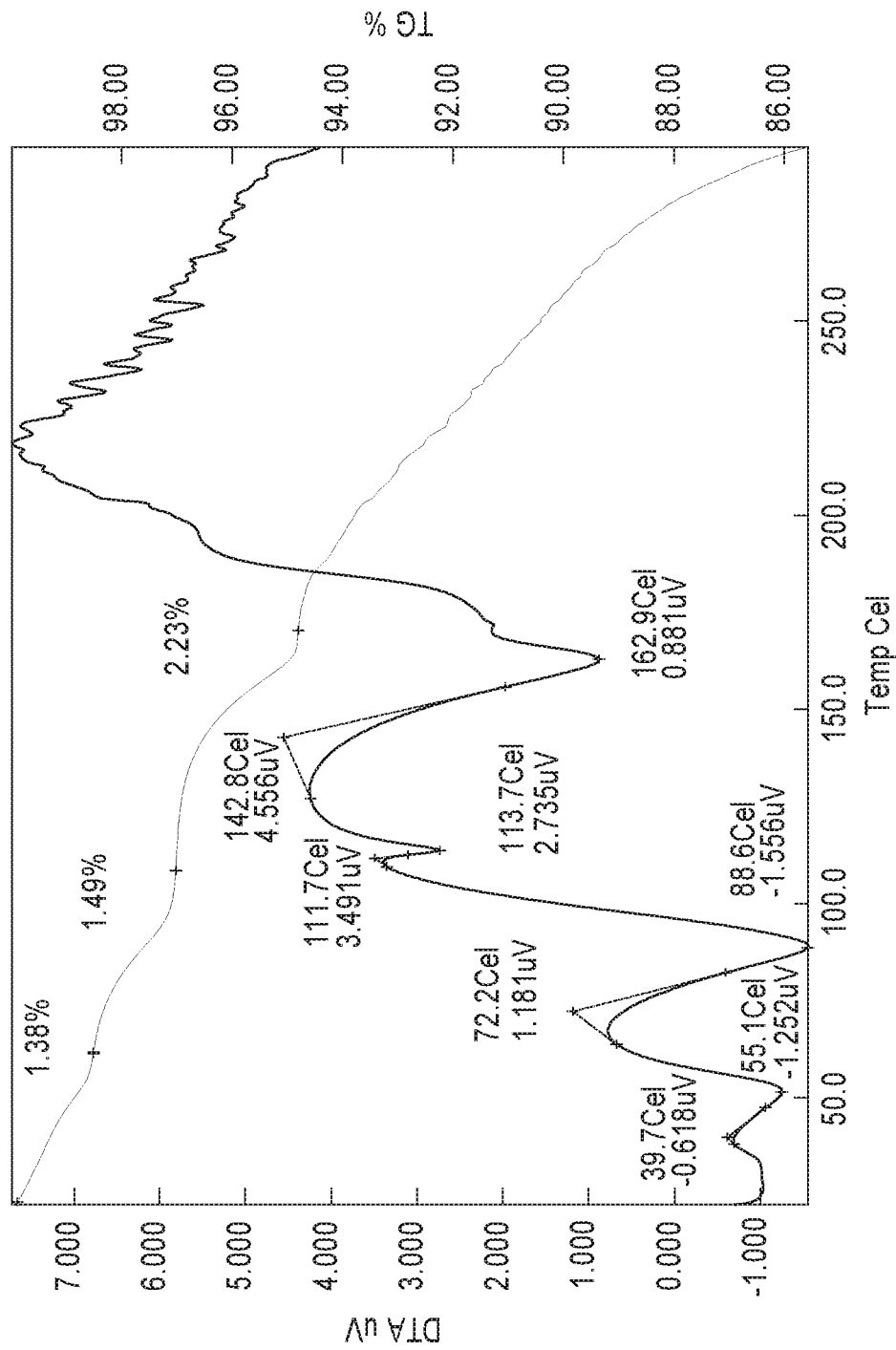
FIG. 6A sets forth thermal analysis by DTA and TG of Form A.

In one embodiment, Form A is characterized by endothermic events with onset at between approximately 40° C. and approximately 49° C., between approximately 72° C. and approximately 74° C., and between approximately 143° C. and approximately 149° C. as measured by DTA or DSC. In one embodiment, Form A is characterized by a further endothermic event with onset at approximately 112° C. as measured by DTA or DSC. In one embodiment, Form A is characterized by endothermic events with onset at approximately 40° C., approximately 72° C., and approximately 143° C. as measured by DTA or DSC. In one embodiment, Form A is characterized by a further endothermic event with onset at approximately 112° C. as measured by DTA or DSC. In one embodiment, Form A is characterized by endothermic events with onset at approximately 49° C., approximately 74° C., and approximately 149° C. as measured by DTA or DSC. In one embodiment, Form A is characterized by a DTA thermogram substantially similar to that set forth in FIG. 6A or a DSC thermogram substantially similar to that set forth in FIG. 6B.

In one embodiment, Form A shows weight losses of approximately 1.4% between about 25° C. and about 60° C., approximately 1.5% between about 60° C. and about 110° C., and approximately 2.2% between about 110° C. and about 170° C., as measured by TGA.

In one embodiment, Form A is hygroscopic. In one embodiment, Form A displays moderate hygroscopicity between 0 and 70% RH at 25° C. (e.g., about 2.5% w/w water uptake). In one embodiment, Form A displays significant hygroscopicity between 70 and 90% RH at 25° C. (e.g., about 5% w/w water uptake).

In one embodiment, Form A is stable under various storage conditions. In one embodiment, Form A is stable at between approximately 20° C. and approximately 50° C. (e.g., 25° C. or 40° C.) for at least one week, two weeks, three weeks, one month, two months, three months, four months, six months, or one year. In one embodiment, Form A is stable at between approximately 60% RH and approximately 98% RH (e.g., 75% RH or 96% RH) for at least one week, two weeks, three weeks, one month, two months, three months, four months, six months, or one year. In one embodiment, Form A is stable under 40° C./75% RH for at least one week, two weeks, three weeks, one month, two months, three months, four months, six months, or one year. In one embodiment, Form A is stable under 25° C./96% RH for at least one week, two weeks, three weeks, one month, two months, three months, four months, six months, or one year.

In one embodiment, Form A is soluble in an aqueous solution. In one embodiment, Form A is dissolved completely in an aqueous solution (e.g., water) at room temperature (>20 mg/ml). In one embodiment, Form A has a low thermodynamic aqueous solubility (e.g., below 1.5 mg/ml). In one embodiment, Form A forms a gel after being dissolved.

In one embodiment, Form A is a hydrate. In one embodiment, Form A is a mono-hydrate.

In one embodiment, Form A is prepared by slurrying an amorphous form of Compound A in a solvent. In one embodiment, the amorphous form of Compound A is slurried in acetone, 1,4-dioxane, or ethanol, or a mixture thereof. In one embodiment, the slurrying is conducted at approximately 50° C. In one embodiment, the slurrying is conducted with continuous agitation. In one embodiment, the slurry is temperature cycled. In one embodiment, the slurry is temperature cycled from about 15° C. to about 50° C. In another embodiment, the slurry is temperature cycled from about 20° C. to about 50° C., from about 25° C. to about 50° C., from about 30° C. to about 50° C., from about 35° C. to about 50° C., from about 40° C. to about 50° C., from about 15° C. to about 45° C., from about 15° C. to about 40° C., from about 15° C. to about 35° C., from about 15° C. to about 30° C., from about 15° C. to about 25° C., from about 20° C. to about 45° C., from about 20° C. to about 40° C., from about 20° C. to about 35° C., from about 20° C. to about 30° C., from about 25° C. to about 45° C., from about 25° C. to about 40° C., from about 25° C. to about 35° C., from about 30° C. to about 45° C., from about 30° C. to about 40° C., or from about 35° C. to about 45° C.

In one embodiment, Form A is converted to the Form E polymorph of Compound A upon heating. In one embodiment, Form A is converted to the Form E polymorph of Compound A upon heating above 100° C. In one embodiment, Form A is converted to the Form E polymorph of Compound A upon heating to or above 120° C.

Form E

In one embodiment, the present application provides a Form E polymorph of Compound A ("Form E") characterized by an X-ray powder diffraction pattern comprising peaks at approximately 10.4, 12.4, and 23.7 °2θ using Cu Kα radiation. In one embodiment, Form E is characterized by an X-ray powder diffraction pattern comprising peaks at approximately 10.4, 12.4, 17.4, 23.7, 25.5, and 27.4 °2θ using Cu Kα radiation. In one embodiment, Form E is characterized by an X-ray powder diffraction pattern comprising peaks at approximately 10.4, 12.4, 13.7, 15.4, 15.8, 17.4, 19.9, 20.7, 21.2, 23.7, 25.5, and 27.4 °2θ using Cu Kα radiation. In one embodiment, Form E is characterized by an X-ray powder diffraction pattern comprising peaks at approximately 4.0, 7.1, 7.8, 10.4, 12.4, 13.7, 14.3, 15.4, 15.8, 17.4, 19.9, 20.7, 21.2, 22.2, 23.7, 25.5, and 27.4 °2θ using Cu Kα radiation. In one embodiment, Form E is characterized by an X-ray powder diffraction pattern comprising peaks at approximately the positions shown in the table below:

| Peak List |
| --- |
| Pos. [° 2θ] |
| 4.0 |
| 7.1 |
| 7.8 |
| 10.4 |
| 12.4 |
| 13.7 |
| 14.3 |
| 15.4 |
| 15.8 |
| 17.4 |
| 19.9 |
| 20.7 |
| 21.2 |
| 21.7 |
| 22.2 |
| 23.7 |
| 24.8 |
| 25.5 |
| 26.5 |
| 27.4 |

Figure 8:
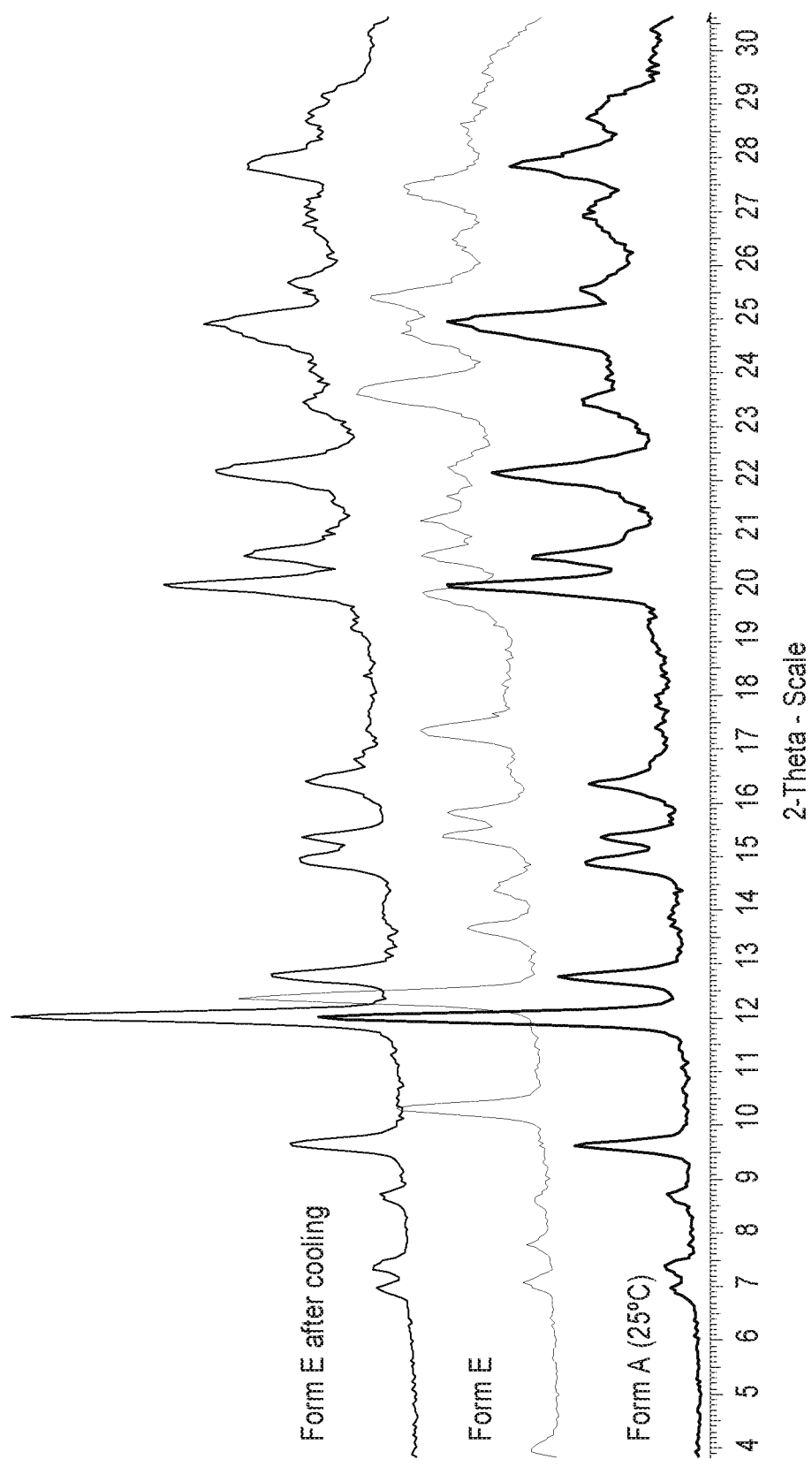
FIG. 8 is X-ray powder diffraction pattern showing the transition from the Form E to Form A.

In one embodiment, Form E is characterized by an X-ray powder diffraction pattern substantially similar to that set forth in FIG. 8.

In one embodiment, Form E is prepared by heating Form A. In one embodiment, Form E is prepared by heating Form A above 100° C. In one embodiment, Form E is prepared by heating Form A to or above 120° C.

In one embodiment, Form E is converted to Form A after cooling. In one embodiment, Form E is converted to Form A after cooling to below 100° C. In one embodiment, Form E is converted to Form A after cooling to the ambient temperature (e.g., about 25° C.).

Form C

In one embodiment, the present application provides a Form C polymorph of Compound A ("Form C") characterized by an X-ray powder diffraction pattern comprising peaks at approximately 8.9, 20.2, and 20.9 °2θ using Cu Kα radiation. In one embodiment, Form C is characterized by an X-ray powder diffraction pattern comprising peaks at approximately 6.9, 8.9, 11.5, 15.6, 20.2, and 20.9 °2θ using Cu Kα radiation. In one embodiment, Form C is characterized by an X-ray powder diffraction pattern comprising peaks at approximately 6.9, 8.9, 11.5, 14.0, 15.6, 18.7, 20.2, 20.9, 22.2, 24.6, 26.2, and 27.0 °2θ using Cu Kα radiation. In one embodiment, Form C is characterized by an X-ray powder diffraction pattern comprising peaks at approximately the positions shown in the table below:

| 2-Theta | d(Å) | BG | Height | H % | Area | A % | FWHM |
| --- | --- | --- | --- | --- | --- | --- | --- |
| 4.256 | 20.7429 | 17 | 45 | 4.3 | 672 | 11.8 | 0.635 |
| 6.862 | 12.8706 | 95 | 470 | 45.0 | 2675 | 46.8 | 0.242 |
| 8.883 | 9.9466 | 122 | 1044 | 100.00 | 5083 | 89.0 | 0.207 |
| 11.545 | 7.6583 | 163 | 466 | 44.6 | 3126 | 54.7 | 0.285 |
| 14.031 | 6.3067 | 206 | 201 | 19.2 | 1281 | 22.4 | 0.271 |
| 15.602 | 5.6750 | 262 | 680 | 65.1 | 3701 | 64.8 | 0.232 |
| 17.787 | 4.9827 | 376 | 142 | 13.6 | 722 | 12.7 | 0.217 |
| 18.698 | 4.7418 | 417 | 518 | 49.6 | 2665 | 46.7 | 0.219 |
| 20.157 | 4.4018 | 511 | 532 | 51.0 | 5710 | 100.0 | 0.456 |
| 20.891 | 4.2488 | 519 | 269 | 25.8 | 3977 | 69.7 | 0.627 |
| 22.152 | 4.0096 | 515 | 234 | 22.4 | 1836 | 32.2 | 0.333 |
| 23.099 | 3.8474 | 516 | 164 | 15.7 | 732 | 12.8 | 0.189 |
| 24.550 | 3.6231 | 523 | 186 | 17.8 | 1454 | 25.5 | 0.332 |
| 26.150 | 3.4050 | 585 | 147 | 14.1 | 1290 | 22.6 | 0.373 |
| 27.048 | 3.2940 | 590 | 112 | 10.7 | 1196 | 20.9 | 0.453 |
| 29.596 | 3.0158 | 385 | 145 | 13.9 | 1141 | 20.0 | 0.334 |

Figure 10:
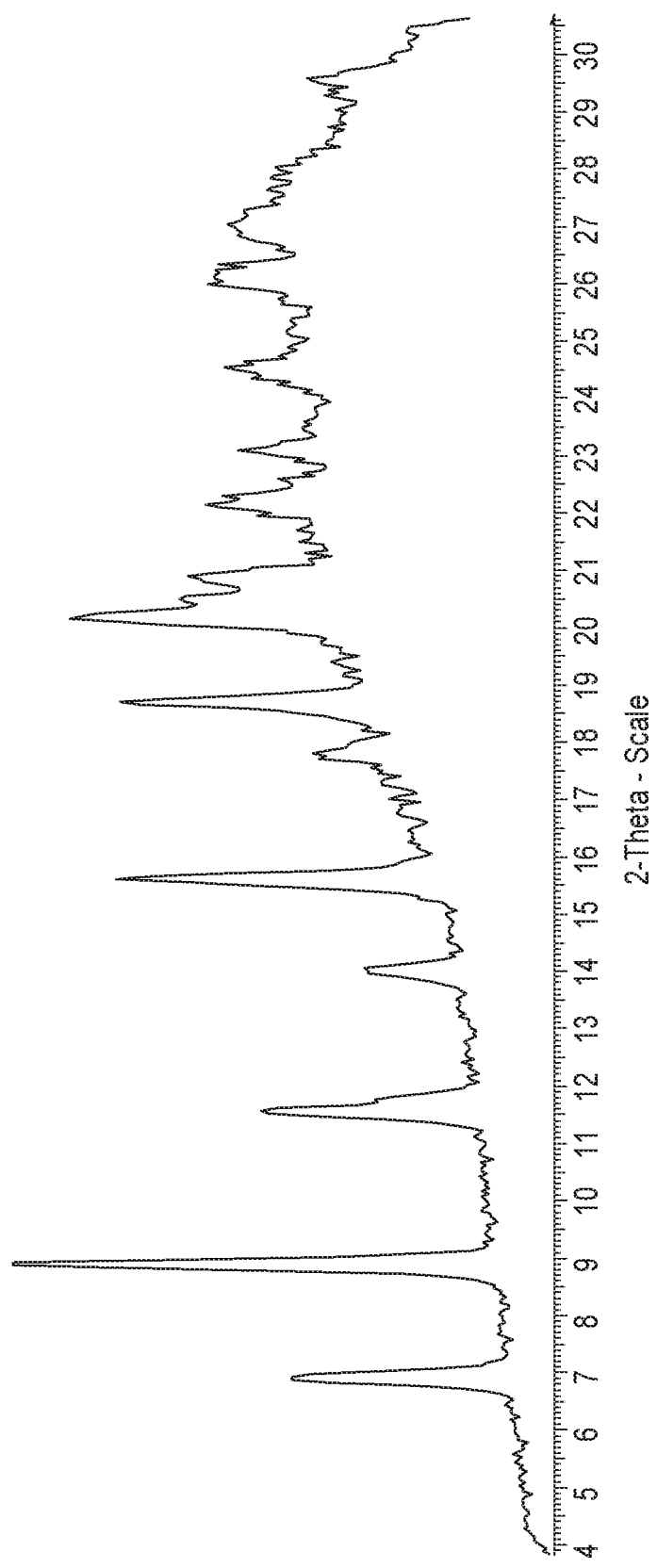
FIG. 10 sets forth an X-ray powder diffraction pattern of Form C.

In one embodiment, Form C is characterized by an X-ray powder diffraction pattern substantially similar to that set forth in FIG. 10.

In one embodiment, Form C is characterized by an endothermic event with onset at approximately 152° C. as measured by DSC. In one embodiment, Form C is characterized by a DSC thermogram substantially similar to that set forth in FIG. 11.

In one embodiment, Form C is prepared by dissolving Compound A (e.g., an amorphous form of Compound A) in DMSO, followed by slow evaporation of DMSO from the solution. In one embodiment, preparation of Form C further comprises heating the sample. In one embodiment, the sample is heated to or above about 75° C.

In one embodiment, Form C is a DMSO solvate. In one embodiment, Form C is a DMSO hemi-solvate.

Form D

In one embodiment, the present application provides a Form D polymorph of Compound A ("Form D") characterized by an X-ray powder diffraction pattern comprising peaks at approximately 14.9, 23.1, and 23.8 °2θ using Cu Kα radiation. In one embodiment, Form D is characterized by an X-ray powder diffraction pattern comprising peaks at approximately 10.6, 14.9, 23.1, 23.8, and 24.8 °2θ using Cu Kα radiation. In one embodiment, Form D is characterized by an X-ray powder diffraction pattern comprising peaks at approximately 10.6, 13.9, 14.9, 21.8, 22.3, 23.1, 23.8, 24.8, 28.1, and 28.7 °2θ using Cu Kα radiation. In one embodiment, Form D is characterized by an X-ray powder diffraction pattern comprising peaks at approximately 10.6, 11.6, 13.9, 14.9, 19.0, 21.8, 22.3, 23.1, 23.8, 24.8, 25.3, 28.1, 28.2, and 28.7 °2θ using Cu Kα radiation. In one embodiment, Form D is characterized by an X-ray powder diffraction pattern comprising peaks at approximately the positions shown in the table below:

| Pos. [° 2θ] | Peak List Height [cts] | Rel. Int. [%] |
|---|---|---|
| 5.1265 | 98.52 | 23.49 |
| 7.3462 | 79.00 | 18.83 |
| 10.5714 | 357.98 | 85.34 |
| 11.5597 | 113.60 | 27.08 |
| 11.7765 | 106.11 | 25.30 |
| 13.9022 | 203.73 | 48.57 |
| 14.9257 | 419.49 | 100.00 |
| 16.3721 | 26.24 | 6.25 |
| 16.7358 | 93.63 | 22.32 |
| 17.2192 | 68.07 | 16.23 |
| 17.5019 | 11.50 | 2.74 |
| 18.3150 | 60.24 | 14.36 |
| 18.9619 | 124.08 | 29.58 |
| 19.7197 | 86.49 | 20.62 |
| 20.7378 | 101.40 | 24.17 |
| 21.0683 | 83.45 | 19.89 |
| 21.7689 | 203.41 | 48.49 |
| 22.8690 | 201.75 | 48.09 |
| 23.1463 | 371.74 | 88.62 |
| 23.7756 | 410.38 | 97.83 |
| 24.8390 | 314.95 | 75.08 |
| 25.2694 | 132.02 | 31.47 |
| 26.2399 | 32.20 | 7.68 |
| 27.2203 | 51.08 | 12.18 |
| 28.0526 | 181.81 | 43.34 |
| 28.1895 | 123.55 | 29.45 |
| 28.7259 | 175.55 | 41.85 |

Figure 13A:
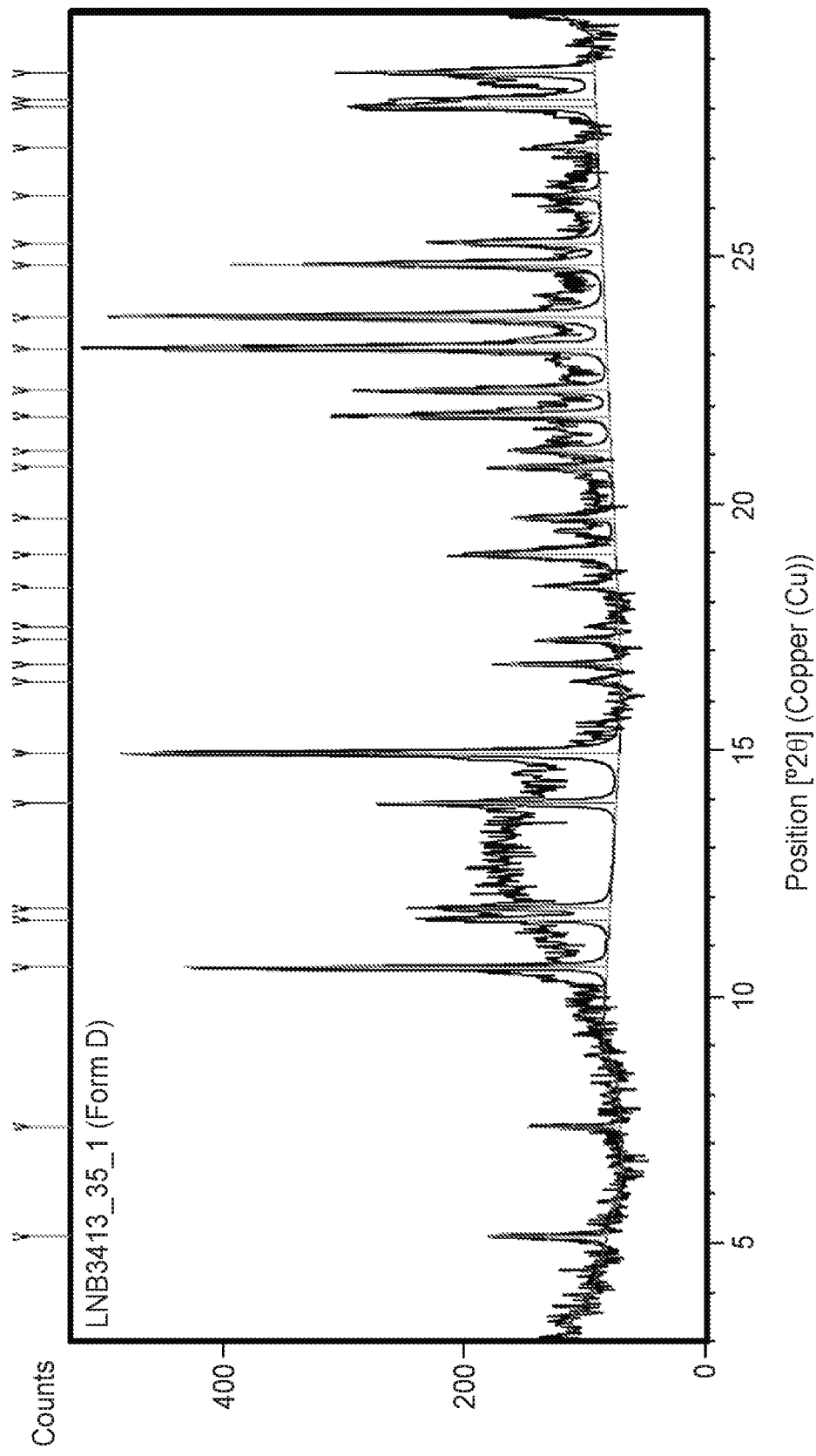
FIG. 13A sets forth an X-ray powder diffraction pattern of Form D.
Figure 13B:
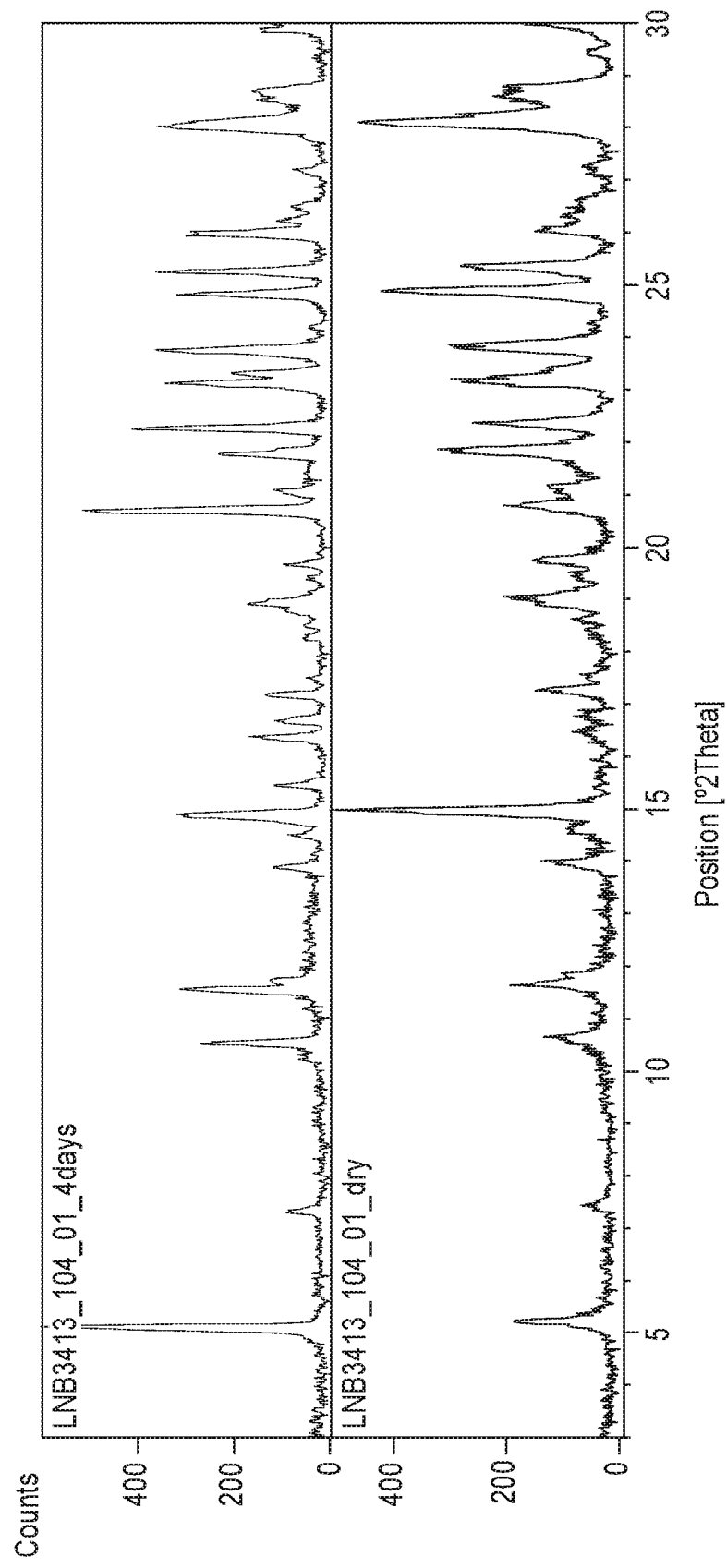
FIG. 13B sets forth X-ray powder diffraction patterns of Form D before drying (top panel) and after drying (bottom panel).
Figure 13C:
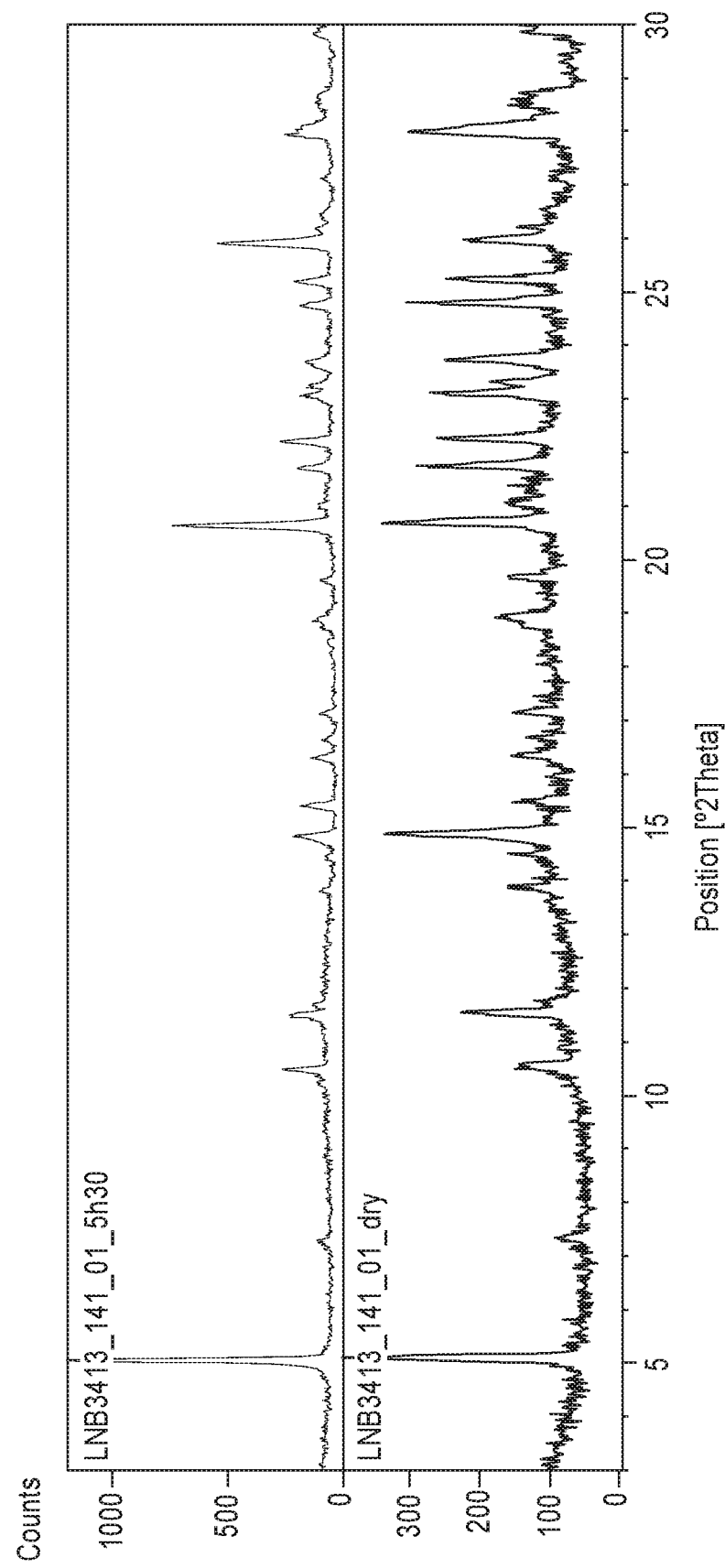
FIG. 13C sets forth X-ray powder diffraction patterns of Form D before drying (top panel) and after drying (bottom panel).

In one embodiment, Form D is characterized by an X-ray powder diffraction pattern substantially similar to that set forth in FIG. 13A, 13B, or 13C. In one embodiment, Form D is characterized by an X-ray powder diffraction pattern substantially similar to that set forth in FIG. 13A.

In one embodiment, Form D is characterized by an endothermic event with onset between approximately 110° C. and approximately 123° C. as measured by DTA or DSC. In one embodiment, Form D is characterized by an endothermic event with onset at approximately 110° C., 112° C., 114° C., 115° C., or 123° C. as measured by DTA or DSC. In one embodiment, Form D is characterized by a DTA thermogram substantially similar to that set forth in any one of FIGS. 16A, 16B, 16C, and 16D.

In one embodiment, Form D shows a weight loss of between approximately 3.5% and approximately 4.6% between about 80° C.-about 90° C. and about 130° C.-about 160° C., as measured by TGA. In one embodiment, Form D shows a weight loss of approximately 3.6% (i.e., 1 mole equivalent water) between about 80° C. and about 130° C., as measured by TGA. In one embodiment, Form D shows a weight loss of approximately 4.6% between about 90° C. and about 160° C., as measured by TGA.

In one embodiment, Form D displays water uptake of less than 0.1% w/w between 40 and 70% RH. In one embodiment, Form D displays significant water uptake between 70 and 90% RH at 25° C. (e.g., about 1.6% w/w water uptake).

In one embodiment, Form D is stable under various storage conditions. In one embodiment, Form D is stable at between approximately 20° C. and approximately 50° C. (e.g., 25° C. or 40° C.) for at least one week, two weeks, three weeks, one month, two months, three months, four months, six months, or one year. In one embodiment, Form D is stable at between approximately 60% RH and approximately 98% RH (e.g., 75% RH or 96% RH) for at least one week, two weeks, three weeks, one month, two months, three months, four months, six months, or one year. In one embodiment, Form D is stable under 40° C./75% RH for at least one week, two weeks, three weeks, one month, two months, three months, four months, six months, or one year. In one embodiment, Form D is stable under 25° C./96% RH for at least one week, two weeks, three weeks, one month, two months, three months, four months, six months, or one year.

In one embodiment, Form D is a hydrate. In one embodiment, Form D is a mono-hydrate.

In one embodiment, Form D is prepared by slurrying an amorphous form of Compound A in a solvent. In one embodiment, the amorphous form of Compound A is slurried in a mixture of acetone, 2-propanol, or acetonitrile with water. In one embodiment, the amorphous form of Compound A is slurried in a mixture of acetone and water. In one embodiment, acetone and water is mixed at a WA of approximately 0.4. In one embodiment, the slurrying is conducted at ambient temperature (e.g., approximately 20° C. to approximately 25° C.). In one embodiment, the slurrying is conducted with continuous agitation.

In one embodiment, Form D is prepared by a method comprising: dissolving Compound A in a first solvent to form a solution; adding an anti-solvent to the solution to form a slurry; and cooling the slurry; and optionally isolating Form D.

In one embodiment, the first solvent is a mixture of acetone, 2-propanol, or acetonitrile and water. In one embodiment, the first solvent is a mixture of acetone and water. In one embodiment, the mixture comprises acetone:water at approximately 85:15. In one embodiment, Compound A is dissolved in the first solvent at a temperature of at least 50° C. In one embodiment, Compound A is dissolved in the first solvent at a temperature of approximately 50° C.

In one embodiment, the anti-solvent is acetone, 2-propanol, or acetonitrile. In one embodiment, the anti-solvent is acetone. In one embodiment, after the addition of the anti-solvent, the percentage of the water in the solution is decreased. In one embodiment, after the addition of the anti-solvent, the percentage of the water in the solution is approximately or less than 5%. In one embodiment, after the addition of the anti-solvent, the solution comprises acetone:water at approximately 95:5. In one embodiment, after the addition of the anti-solvent, a slurry is formed.

In one embodiment, after the addition of the anti-solvent, the slurry is cooled to a temperature of approximately or below 20° C.

In one embodiment, the method further comprises, after the addition of the anti-solvent and before cooling, adding a Form D seed. In one embodiment, the Form D seed is added when the percentage of water is decreased to between approximately 13% and approximately 10%.

In one embodiment, the method further comprises, after the addition of the Form D seed and before cooling, adding the anti-solvent. In one embodiment, the anti-solvent is added to decrease the percentage of water to between approximately 10% and approximately 5%. In one embodiment, the anti-solvent is added to decrease the percentage of water to approximately 5%. In one embodiment, after the addition of the Form D seed and further anti-solvent, the slurry is cooled to a temperature of approximately or below 20° C.

In one embodiment, the method further comprises, after the cooling, filtering Form D.

In one embodiment, Form D is prepared by slurrying the Form G polymorph of Compound A in a solvent. In one embodiment, the Form G polymorph of Compound A is slurried in a mixture of acetone, 2-propanol, or acetonitrile with water. In one embodiment, the Form G polymorph of Compound A is slurried in a mixture of acetone and water. In one embodiment, the mixture of acetone and water has a low water content (e.g., less than 8%, 7%, 6%, 5%, 4%, 3%, or 2% water). In one embodiment, acetone and water is mixed at a acetone:water ratio of approximately 98:2 or 99:1. In one embodiment, the slurrying is conducted at a temperature of at least 50° C. In one embodiment, the slurrying is conducted at approximately 50° C. In one embodiment, the slurrying is conducted with continuous agitation. In one embodiment, the slurrying is conducted for at least 3 days, 4 days, or longer. In one embodiment, a Form D seed is added to the slurry. In one embodiment, a Form D seed is added to the slurry, and the slurrying is conducted for less than 10 hours, 8 hours, or 6 hours.

Form F

In one embodiment, the present application provides a Form F polymorph of Compound A ("Form F") characterized by an X-ray powder diffraction pattern comprising peaks at approximately 11.1, 17.9, and 28.2 °2θ using Cu Kα radiation. In one embodiment, Form F is characterized by an X-ray powder diffraction pattern comprising peaks at approximately 4.7, 8.8, 11.1, 12.4, 17.9, and 28.2 °2θ using Cu Kα radiation. In one embodiment, Form F is characterized by an X-ray powder diffraction pattern comprising peaks at approximately 4.7, 8.8, 11.1, 12.4, 15.1, 16.8, 17.9, 20.1, 22.5, 24.0, 25.6, and 28.2 °2θ using Cu Kα radiation. In one embodiment, Form F is characterized by an X-ray powder diffraction pattern comprising peaks at approximately the positions shown in the table below:

Peak List

| Pos. [° 2θ] | Height [cts] | Rel. Int. [%] |
| --- | --- | --- |
| 4.6967 | 217.20 | 21.45 |
| 5.8669 | 41.85 | 4.13 |
| 6.1319 | 99.29 | 9.81 |
| 8.7707 | 162.54 | 16.05 |
| 11.1418 | 1012.52 | 100.00 |
| 12.3508 | 224.55 | 22.18 |
| 15.0859 | 110.79 | 10.94 |
| 16.8086 | 162.01 | 16.00 |
| 17.9051 | 439.61 | 43.42 |
| 19.8378 | 35.06 | 3.46 |
| 20.0998 | 118.15 | 11.67 |
| 20.6692 | 42.06 | 4.15 |
| 21.6600 | 73.36 | 7.25 |
| 22.0457 | 67.06 | 6.62 |
| 22.4765 | 108.09 | 10.68 |
| 23.4088 | 80.34 | 7.94 |
| 23.9847 | 108.97 | 10.76 |
| 25.2417 | 52.06 | 5.14 |
| 25.5571 | 142.99 | 14.12 |
| 26.1400 | 69.38 | 6.85 |
| 27.4225 | 41.06 | 4.05 |
| 28.2101 | 261.53 | 25.83 |
| 28.8661 | 71.14 | 7.03 |

Figure 17A:
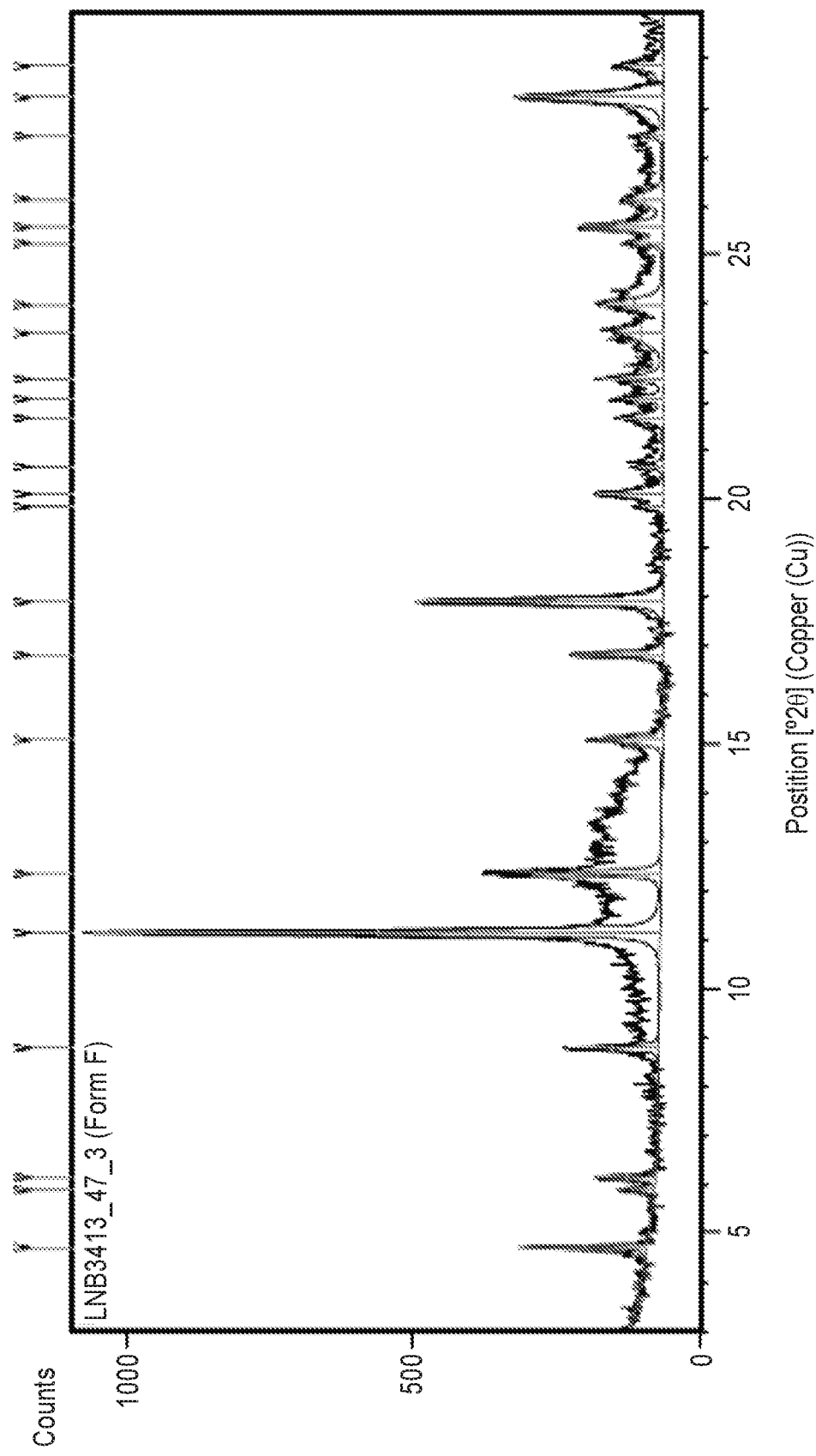
FIG. 17A sets forth an X-ray powder diffraction pattern of Form F.
Figure 17B:
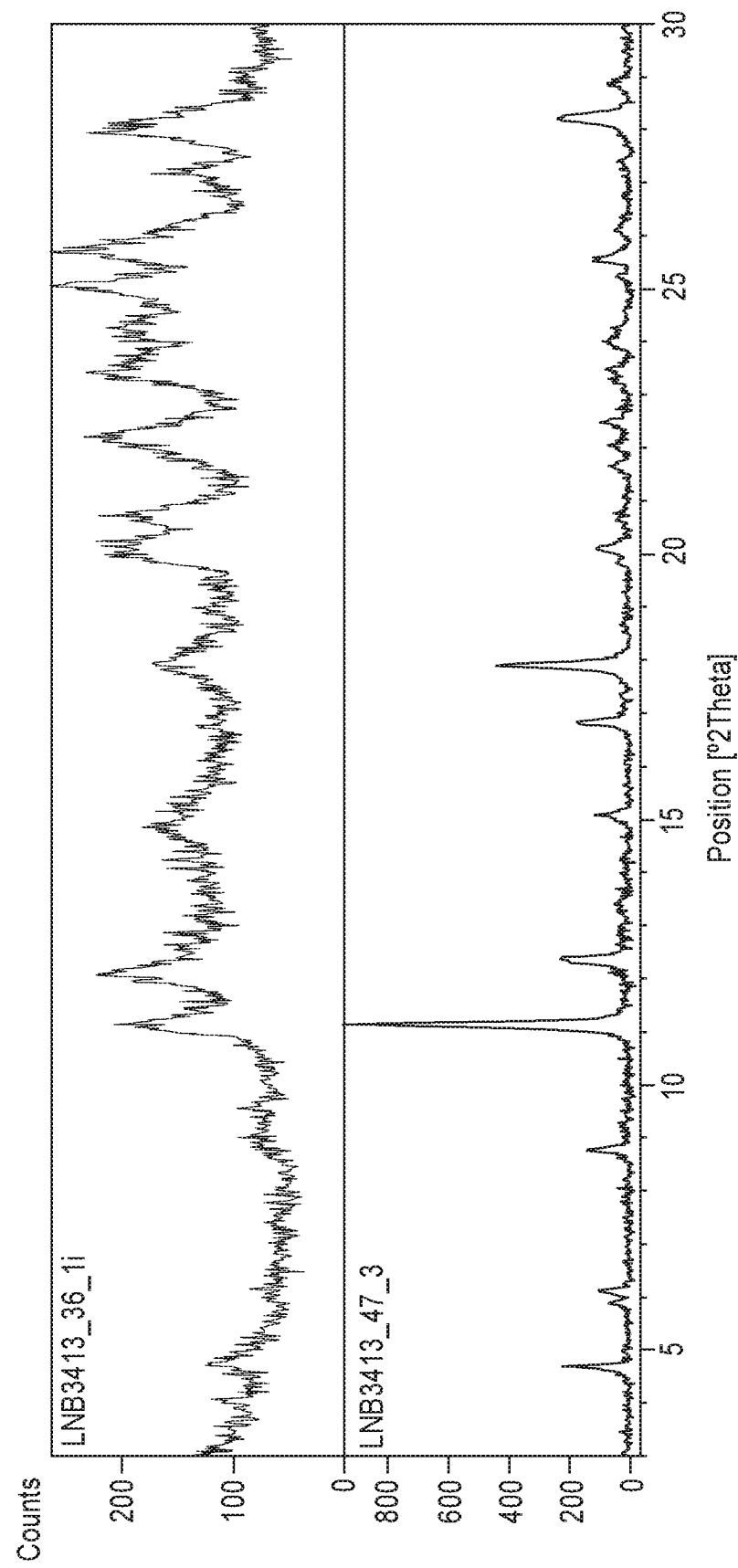
FIG. 17B sets forth X-ray powder diffraction patterns of Form F: sample prepared by storing an amorphous form of Compound A in 40° C./75% RH (top panel) and sample prepared through slurrying an amorphous form of Compound A in acetonitrile (bottom panel).

In one embodiment, Form F is characterized by an X-ray powder diffraction pattern substantially similar to that set forth in FIG. 17A or 17B. In one embodiment, Form F is characterized by an X-ray powder diffraction pattern substantially similar to that set forth in FIG. 17A.

Figure 18:
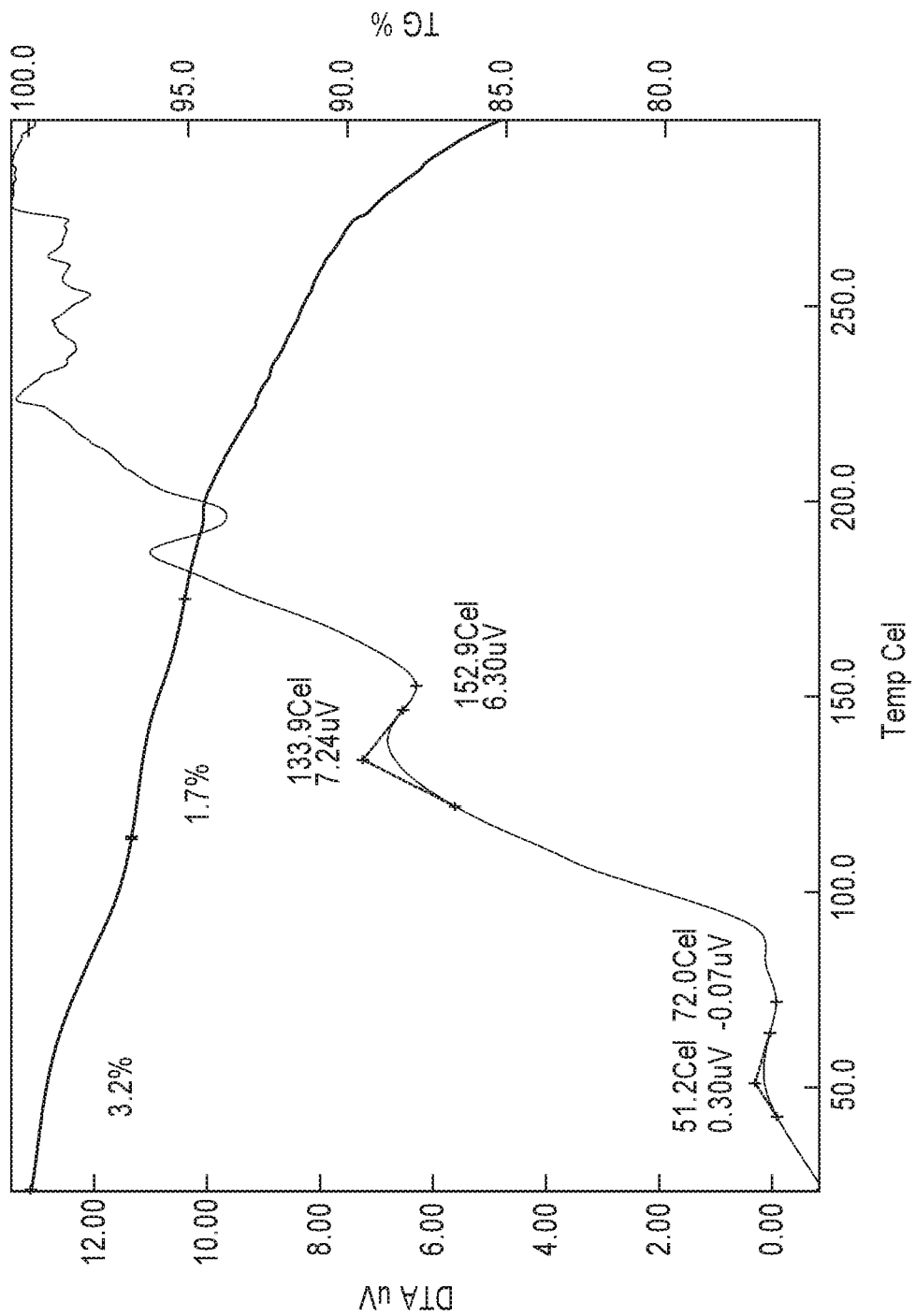
FIG. 18 sets forth thermal analysis by DTA and TG of Form F.

In one embodiment, Form F is characterized by endothermic events with onset at approximately 51° C. and approximately 133° C. as measured by DTA. In one embodiment, Form F is characterized by a DTA thermogram substantially similar to that set forth in FIG. 18.

In one embodiment, Form F shows weight losses of approximately 3.2% (i.e., 1 mole equivalent water) between about 25° C. and about 110° C., and approximately 1.7% between about 110° C. and about 170° C., as measured by TGA.

In one embodiment, Form F is a hydrate.

In one embodiment, Form F is prepared by storing the amorphous form of Compound A at 40° C./75% RH. In one embodiment, the amorphous form of Compound A is stored at 40° C./75% RH for at least 6 days. In one embodiment, the amorphous form of Compound A is stored at 40° C./75% RH for additional 4 days.

In one embodiment, Form F is prepared by slurrying an amorphous form of Compound A in a solvent. In one embodiment, the amorphous form of Compound A is slurried in acetonitrile. In one embodiment, the slurrying is conducted at approximately 50° C. In one embodiment, the slurrying is conducted with continuous agitation. In one embodiment, the slurry is temperature cycled. In one embodiment, the slurry is temperature cycled from about 15° C. to about 50° C. In another embodiment, the slurry is temperature cycled from about 20° C. to about 50° C., from about 25° C. to about 50° C., from about 30° C. to about 50° C., from about 35° C. to about 50° C., from about 40° C. to about 50° C., from about 15° C. to about 45° C., from about 15° C. to about 40° C., from about 15° C. to about 35° C., from about 15° C. to about 30° C., from about 15° C. to about 25° C., from about 20° C. to about 45° C., from about 20° C. to about 40° C., from about 20° C. to about 35° C., from about 20° C. to about 30° C., from about 25° C. to about 45° C., from about 25° C. to about 40° C., from about 25° C. to about 35° C., from about 30° C. to about 45° C., from about 30° C. to about 40° C., or from about 35° C. to about 45° C.

Form G

In one embodiment, the present application provides a Form G polymorph of Compound A ("Form G") characterized by an X-ray powder diffraction pattern comprising peaks at approximately 9.0, 9.6, and 24.2 °2θ using Cu Kα radiation. In one embodiment, Form G is characterized by an X-ray powder diffraction pattern comprising peaks at approximately 9.0, 9.6, 13.1, 18.3, 19.1, and 24.2 °2θ using Cu Kα radiation. In one embodiment, Form G is characterized by an X-ray powder diffraction pattern comprising peaks at approximately 6.4, 9.0, 9.6, 13.1, 18.1, 18.3, 18.6, 19.1, 22.9, 24.2, 26.4, and 27.3 °2θ using Cu Kα radiation. In one embodiment, Form G is characterized by an X-ray powder diffraction pattern comprising peaks at approximately 6.4, 7.8, 9.0, 9.6, 12.7, 13.1, 16.6, 18.1, 18.3, 18.6, 19.1, 22.9, 23.5, 24.2, 25.5, 26.0, 26.4, 26.9, 27.3, and 29.0 °2θ using Cu Kα radiation. In one embodiment, Form G is characterized by an X-ray powder diffraction pattern comprising peaks at approximately the positions shown in the table below:

Peak List

| Pos. [° 2θ] | Height [cts] | Rel. Int. [%] |
| --- | --- | --- |
| 6.3578 | 156.96 | 46.19 |
| 7.8238 | 70.87 | 20.85 |
| 9.0274 | 339.84 | 100.00 |
| 9.5822 | 270.63 | 79.63 |
| 12.7095 | 127.49 | 37.51 |
| 13.0939 | 181.65 | 53.45 |
| 14.9647 | 52.72 | 15.51 |
| 16.5707 | 113.56 | 33.41 |
| 18.1237 | 136.31 | 40.11 |
| 18.2833 | 228.31 | 67.18 |
| 18.6386 | 180.55 | 53.13 |

-continued

Peak List

| Pos. [° 2θ] | Height [cts] | Rel. Int. [%] |
|---|---|---|
| 19.0947 | 219.37 | 64.55 |
| 20.9564 | 24.31 | 7.15 |
| 21.5439 | 46.74 | 13.75 |
| 22.8567 | 134.31 | 39.52 |
| 23.5313 | 85.03 | 25.02 |
| 24.1745 | 240.93 | 70.90 |
| 24.7712 | 52.31 | 15.39 |
| 25.4666 | 106.01 | 31.19 |
| 26.0242 | 103.31 | 30.40 |
| 26.3932 | 142.31 | 41.88 |
| 26.9217 | 75.31 | 22.16 |
| 27.2750 | 156.50 | 46.05 |
| 27.8390 | 37.31 | 10.98 |
| 28.4667 | 46.38 | 13.65 |
| 28.9559 | 94.31 | 27.75 |
| 29.5172 | 32.31 | 9.51 |
| 29.7879 | 35.31 | 10.39 |

Figure 20A:
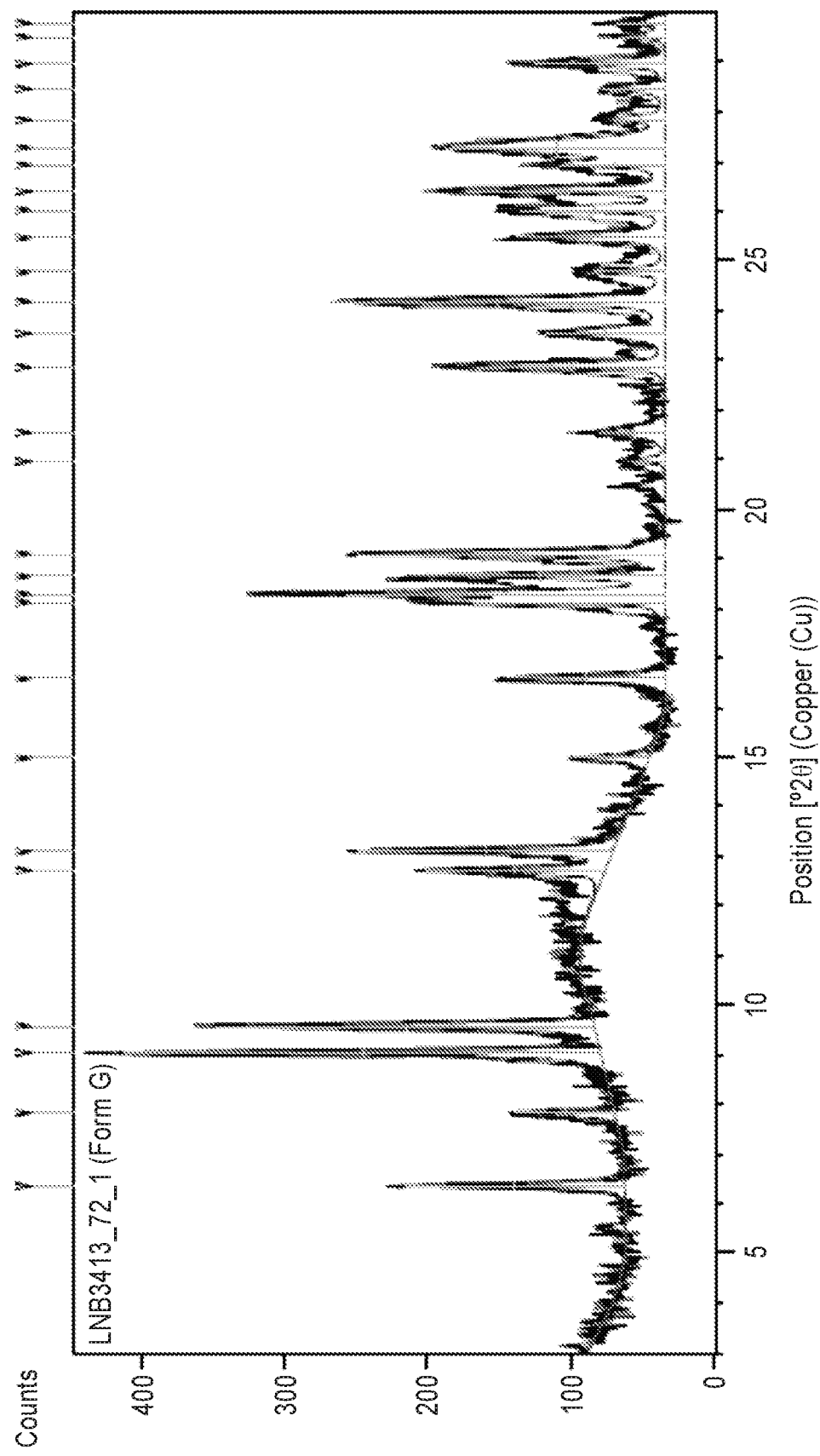
FIG. 20A sets forth an X-ray powder diffraction pattern of Form G.
Figure 20B:
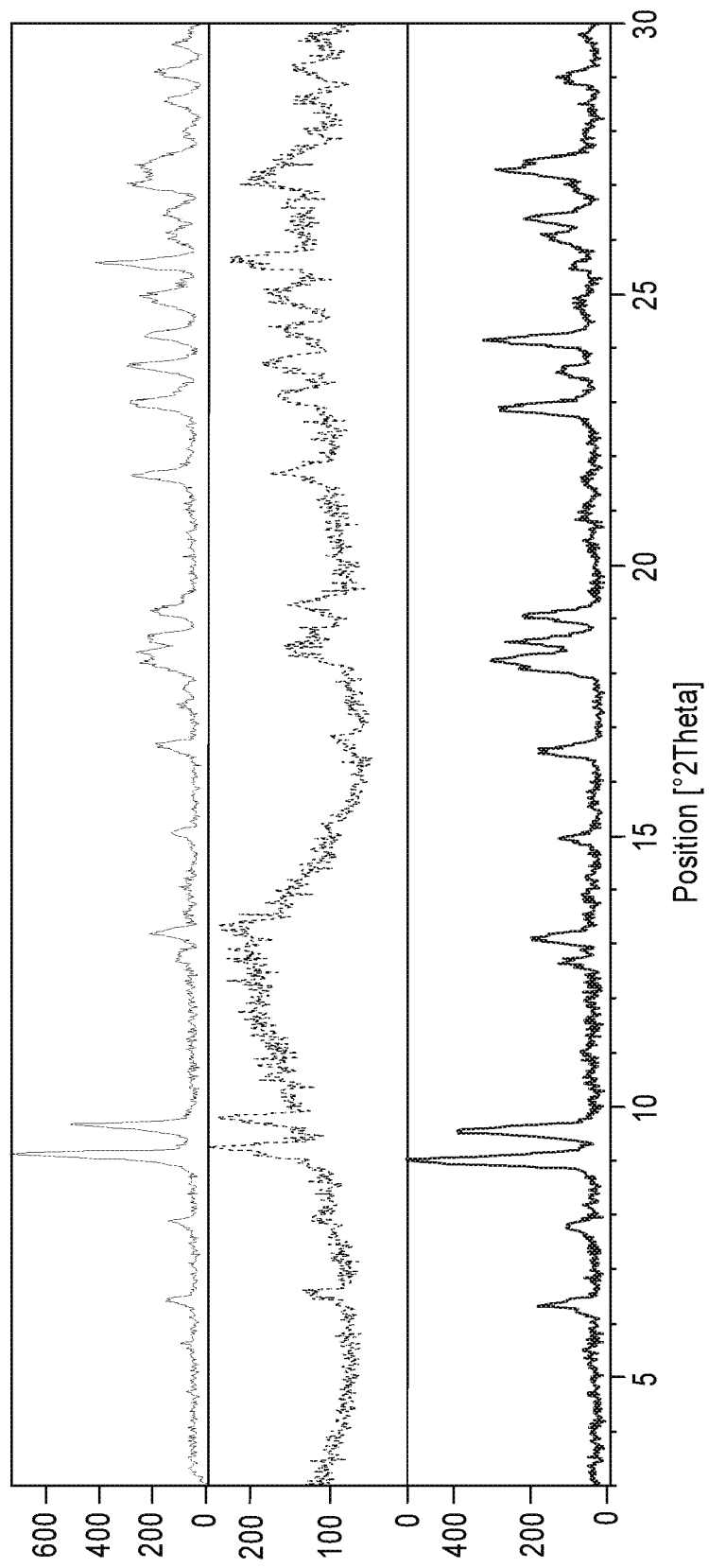
FIG. 20B sets forth X-ray powder diffraction patterns of Form G (top panel), after addition of solvent at 50° C. for 96 hours (middle panel), and after a further 48 hours at 50° C. (bottom panel).
Figure 20C:
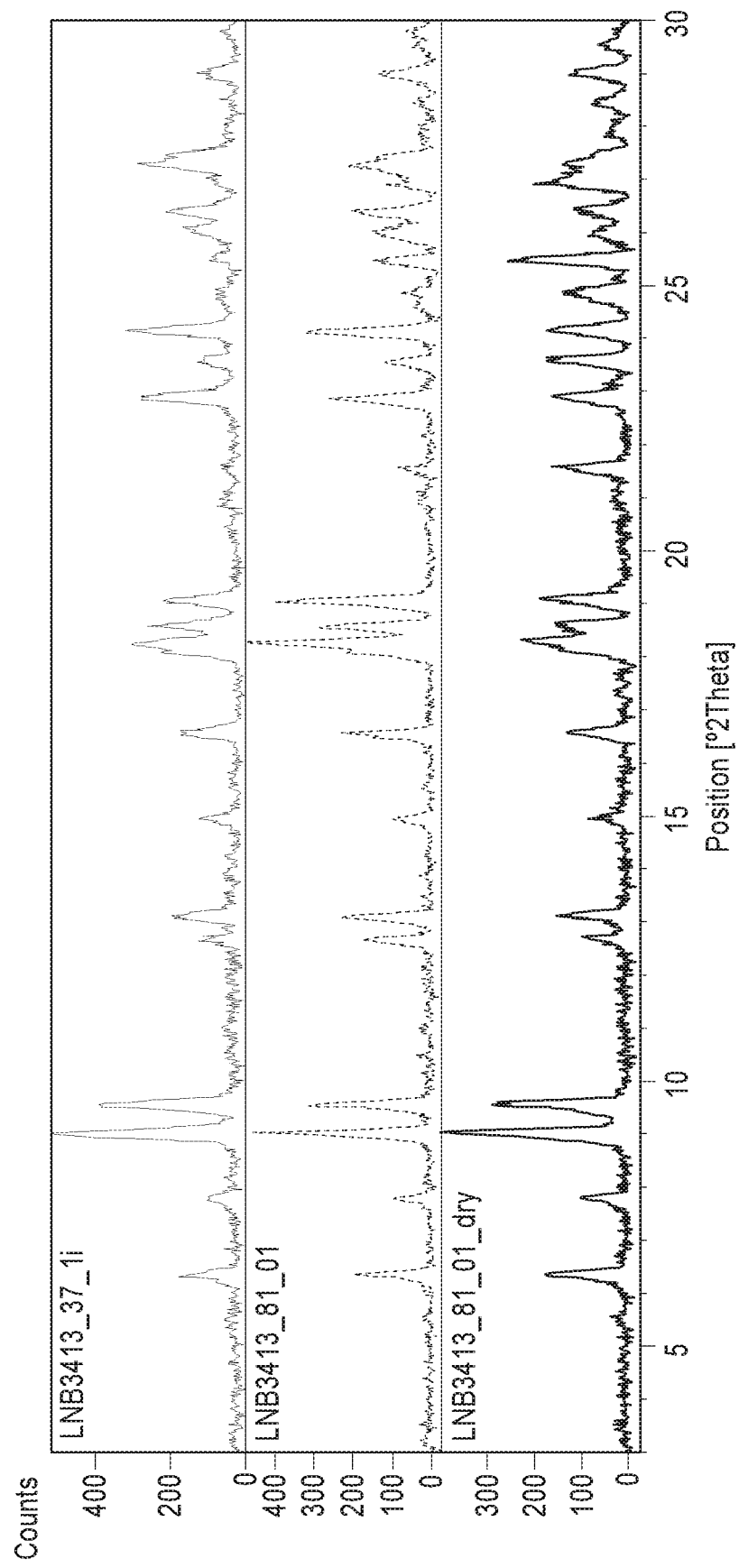
FIG. 20C sets forth X-ray powder diffraction patterns of Form G: reference sample (top panel), and 15 g scale sample before drying (middle panel) and after drying (bottom panel).

In one embodiment, Form G is characterized by an X-ray powder diffraction pattern substantially similar to that set forth in FIG. 20A, 20B, or 20C. In one embodiment, Form G is characterized by an X-ray powder diffraction pattern substantially similar to that set forth in FIG. 20A.

In one embodiment, Form G is characterized by an endothermic event with onset between approximately 108° C. and approximately 125° C. as measured by DTA. In one embodiment, Form G is characterized by an endothermic event with onset at approximately 108° C., 110° C., 111° C., 112° C., 113° C., 114° C., or 125° C. as measured by DTA. In one embodiment, Form G is characterized by a DTA thermogram substantially similar to that set forth in any one of FIGS. 21A, 21B, 21C, and 21D.

In one embodiment, Form G shows a weight loss of between approximately 5.1% and approximately 5.7% between about 25° C.-about 40° C. and about 130° C.-about 150° C., as measured by TGA. In one embodiment, Form G shows a weight loss of approximately 5.1% between about 25° C. and about 130° C., as measured by TGA. In one embodiment, Form G shows a weight loss of approximately 5.7% between about 40° C. and about 150° C., as measured by TGA.

In one embodiment, Form G displays water uptake of approximately 1.1% w/w between 20 and 70% RH. In one embodiment, Form G displays water uptake of approximately 1.3% w/w between 70 and 90% RH.

In one embodiment, Form G is stable under various storage conditions. In one embodiment, Form G is stable at between approximately 20° C. and approximately 70° C. (e.g., 25° C., 40° C., or 60° C.) for at least one week, two weeks, three weeks, one month, two months, three months, four months, six months, or one year. In one embodiment, Form G is stable at between approximately 60% RH and approximately 90% RH (e.g., 75% RH) for at least one week, two weeks, three weeks, one month, two months, three months, four months, six months, or one year. In one embodiment, Form G is stable under 40° C. or 60° C. for at least one week, two weeks, three weeks, one month, two months, three months, four months, six months, or one year. In one embodiment, Form G is stable under 40° C./75% RH for at least one week, two weeks, three weeks, one month, two months, three months, four months, six months, or one year.

In one embodiment, Form G is a hydrate.

In one embodiment, Form G is prepared by slurrying an amorphous form of Compound A in a solvent. In one embodiment, the amorphous form of Compound A is slurried in a mixture of acetone, 2-propanol, or acetonitrile with water. In one embodiment, the amorphous form of Compound A is slurried in a mixture of 2-propanol and water. In one embodiment, 2-propanol and water is mixed at a WA of approximately 0.9. In one embodiment, the slurrying is conducted at a temperature of at least 50° C. In one embodiment, the slurrying is conducted at approximately 50° C. In one embodiment, the slurrying is conducted with continuous agitation.

In one embodiment, Form G is prepared by a method comprising: dissolving Compound A in a first solvent to form a solution; and cooling the solution; and optionally adding an anti-solvent to the solution to form a slurry; and optionally isolating Form G.

In one embodiment, the first solvent is a mixture of acetone, 2-propanol, or acetonitrile and water. In one embodiment, the first solvent is a mixture of acetone and water. In one embodiment, the mixture comprises acetone: water at approximately 85:15. In one embodiment, the first solvent is a mixture of 2-propanol and water. In one embodiment, the mixture comprises 2-propanol:water at approximately 25:75. In one embodiment, Compound A is dissolved in the first solvent at a temperature of at least 40° C. In one embodiment, Compound A is dissolved in the first solvent at a temperature of approximately 40° C. In one embodiment, Compound A is dissolved in the first solvent at a temperature of approximately 50° C. In one embodiment, dissolving Compound A comprises increasing the temperature (e.g., to approximately 60° C.), and/or adding additional amount of the first solvent, to facilitate the dissolution of Compound A. In one embodiment, dissolving Compound A comprises stirring the solution.

In one embodiment, the solution is cooled to a temperature of approximately or below 25° C. In one embodiment, the solution is cooled to approximately 22° C. In one embodiment, the cooling comprises multiple steps of cooling. In one embodiment, the cooling comprises cooling to a first temperature, followed by cooling to a second temperature. In one embodiment, the cooling comprises cooling to approximately 40° C. or approximately 30° C., then cooling to approximately 22° C. In one embodiment, the cooling comprises a third step of cooling to a third temperature. In one embodiment, the third step comprises cooling to approximately 5° C.

In one embodiment, the anti-solvent is acetone, 2-propanol, or acetonitrile. In one embodiment, the anti-solvent is acetone. In one embodiment, after the addition of the anti-solvent, the percentage of the water in the solution is decreased. In one embodiment, after the addition of the anti-solvent, the percentage of the water in the solution is approximately or less than 5%. In one embodiment, after the addition of the anti-solvent, the solution comprises acetone: water at approximately 95:5. In one embodiment, after the addition of the anti-solvent, a slurry is formed.

Form B

In one embodiment, the present application provides a Form B solid form of Compound A ("Form B") characterized by an X-ray powder diffraction pattern comprising peaks at approximately 5.2, 9.3, and 10.6 °2θ using Cu Kα radiation. In one embodiment, Form B is characterized by an X-ray powder diffraction pattern comprising peaks at approximately 5.2, 9.3, 10.6, 12.3, 16.2, 19.4, and 20.0 °2θ using Cu Kα radiation. In one embodiment, Form B is characterized by an X-ray powder diffraction pattern comprising peaks at approximately the positions shown in the table below:

| 2-Theta | d(Å) | BG | Height | H % | Area | A % | FWHM |
|---------|------|----|--------|-----|------|-----|------|
| 4.399 | 20.0697 | 27 | 73 | 11.3 | 654 | 10.7 | 0.382 |
| 5.245 | 16.8357 | 104 | 644 | 100.0 | 6126 | 100.0 | 0.404 |
| 7.004 | 12.6109 | 125 | 112 | 17.3 | 852 | 13.9 | 0.325 |
| 9.302 | 9.4994 | 181 | 260 | 40.3 | 1574 | 25.7 | 0.258 |
| 10.096 | 8.7544 | 210 | 56 | 8.8 | 281 | 4.6 | 0.212 |
| 10.613 | 8.3287 | 199 | 210 | 32.5 | 1974 | 32.2 | 0.400 |
| 12.257 | 7.2153 | 224 | 196 | 30.5 | 1552 | 25.3 | 0.336 |
| 14.150 | 6.2539 | 251 | 73 | 11.4 | 618 | 10.1 | 0.359 |
| 14.686 | 6.0268 | 259 | 147 | 22.7 | 1250 | 20.4 | 0.363 |
| 16.201 | 5.4667 | 309 | 145 | 22.5 | 1338 | 21.8 | 0.393 |
| 17.797 | 4.9797 | 392 | 85 | 13.3 | 571 | 9.3 | 0.284 |
| 19.353 | 4.5828 | 565 | 111 | 17.2 | 105 | 1.7 | 0.050 |
| 19.992 | 4.4378 | 504 | 196 | 30.4 | 3277 | 53.5 | 0.712 |
| 23.103 | 3.8467 | 656 | 113 | 17.6 | 1687 | 27.5 | 0.633 |
| 23.688 | 3.7530 | 680 | 108 | 16.7 | 1418 | 23.2 | 0.559 |
| 29.648 | 3.0108 | 206 | 247 | 38.3 | 3612 | 59.0 | 0.621 |

Figure 25:
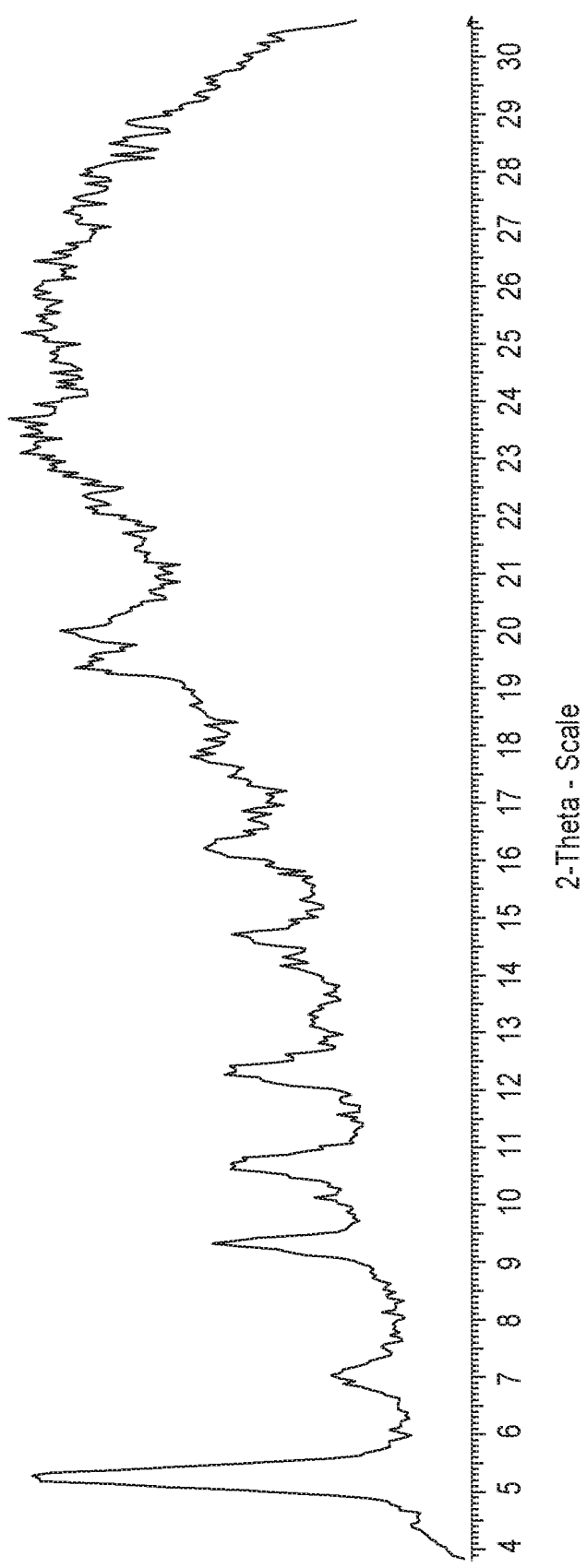
FIG. 25 sets forth an X-ray powder diffraction pattern of the Form B solid form of Compound A.

In one embodiment, Form B is characterized by an X-ray powder diffraction pattern substantially similar to that set forth in FIG. 25. In one embodiment, Form B is partially crystalline and partially amorphous.

In one embodiment, Form B is characterized by an endothermic event with onset at approximately 158° C. as measured by DSC. In one embodiment, Form B is characterized by a DSC thermogram substantially similar to that set forth in FIG. 26.

In one embodiment, Form B shows weight losses of approximately 0.7% at approximately 55° C., and approximately 3.6% between about 80° C. and about 110° C., as measured by TGA.

In one embodiment, Form B is a hydrate. In one embodiment, the Form B polymorph of Compound A is a monohydrate.

In one embodiment, Form B is prepared by mixing an amorphous form or the Form A polymorph of Compound A in a solvent to form a solution or slurry; and isolating Form B from the solution. In one embodiment, the solvent is EtOAc.

The terms "crystalline polymorphs", "crystal polymorphs", "crystal forms", "polymorphs", or "polymorphic forms" means crystal structures in which a compound (e.g., free base, salts, or solvates thereof) can crystallize in different crystal packing arrangements, all of which have the same elemental composition. Different crystal forms usually have different X-ray diffraction patterns, infrared spectra, melting points, density, crystal shape, optical and electrical properties, stability, and solubility. Crystallization solvent, rate of crystallization, storage temperature, and other factors may cause one crystal form to dominate. Crystal polymorphs of the compounds can be prepared by crystallization under different conditions. In addition, crystal polymorphism may be present but is not limiting, but any crystal form may be a single or a crystal form mixture, or an anhydrous or hydrated crystal form.

The term "amorphous form" refers to a noncrystalline solid state form of a substance.

Additionally, the compounds of the present application (e.g., free bases and salts, and amorphous forms, crystalline forms, and polymorphs thereof), can exist in either hydrated or unhydrated (the anhydrous) form or as solvates with other solvent molecules or in an unsolvated form. Nonlimiting examples of hydrates include hemihydrates, monohydrates, dihydrates, etc. Nonlimiting examples of solvates include DMSO solvates, DMSO hemisolvates, etc.

All forms of the compounds of the present application are contemplated, either in a mixture or in pure or substantially pure form, including crystalline forms of racemic mixtures and crystalline forms of individual isomers.

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion, and sublimation.

Techniques for characterizing solid forms of a compound, such as polymorphs, include, but are not limited to, differential scanning calorimetry (DSC), X-ray powder diffractometry (XRPD), single crystal X-ray diffractometry, vibrational spectroscopy (e.g., IR and Raman spectroscopy), TGA, DTA, DVS, solid state NMR, hot stage optical microscopy, scanning electron microscopy (SEM), electron crystallography and quantitative analysis, particle size analysis (PSA), surface area analysis, solubility studies, and dissolution studies.

As used herein, the term "solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. For example, the solvate may be a DMSO solvate, a dichloromethane (DCM) solvate, a methyl ethyl ketone (MEK solvate), or a tetrahydrofuran (THF) solvate.

As used herein, the terms "unsolvated" or "desolvated" refer to a solid state form (e.g., crystalline forms, amorphous forms, and polymorphs) of a substance which does not contain solvent.

As used herein, the term "pure" means about 90-100%, preferably 95-100%, more preferably 98-100% (wt./wt.), or 99-100% (wt./wt.) pure compound; e.g., less than about 10%, less than about 5%, less than about 2%, or less than about 1% impurity is present. Such impurities include, e.g., degradation products, oxidized products, solvents, and/or other undesirable impurities.

As used herein, a compound is "stable" where significant amount of degradation products are not observed under constant conditions of humidity (e.g., 10%, 20%, 30%, 40%, 50%, 60%, 70%, 75%, 80%, 85%, 90%, and 95% RH), light exposure and temperatures (e.g., higher than 0° C., e.g., 20° C., 25° C., 30° C., 35° C., 40° C., 45° C., 50° C., 55° C., 60° C., 65° C., and 70° C.) over a certain period (e.g., one week, two weeks, three weeks, and four weeks). A compound is not considered to be stable at a certain condition when degradation impurities appear or an area percentage (e.g., AUC as characterized by HPLC) of existing impurities begins to grow. The amount of degradation growth as a function of time is important in determining compound stability.

As used herein, the term "mixing" means combining, blending, stirring, shaking, swirling, or agitating. The term "stirring" means mixing, shaking, agitating, or swirling. The term "agitating" means mixing, shaking, stirring, or swirling.

Unless explicitly indicated otherwise, the terms "approximately" and "about" are synonymous. In one embodiment, "approximately" and "about" refer to recited amount, value, or duration±10%, ±8%, ±6%, ±5%, ±4%, ±2%, ±1%, or ±0.5%. In another embodiment, "approximately" and "about" refer to listed amount, value, or duration±10%, ±8%, ±6%, ±5%, ±4%, or ±2%. In yet another embodiment, "approximately" and "about" refer to listed amount, value, or duration±5%. In yet another embodiment, "approximately" and "about" refer to listed amount, value, or duration±2% or ±1%.

When the terms "approximately" and "about" are used when reciting XRPD peaks, these terms refer to the recited X-ray powder diffraction peak±0.3 °2θ, ±0.2 °2θ, or ±0.1 °2θ. In another embodiment, the terms "approximately" and "about" refer to the listed X-ray powder diffraction peak±0.2 °2θ. In another embodiment, the terms "approximately" and "about" refer to the listed X-ray powder diffraction peak±0.1 °2θ.

When the terms "approximately" and "about" are used when reciting temperature or temperature range, these terms refer to the recited temperature or temperature range±5° C., ±2° C., or ±1° C. In another embodiment, the terms "approximately" and "about" refer to the recited temperature or temperature range±2° C.

Methods and Assays
Synthesis of Compound a

Standard synthetic methods and procedures for the preparation of organic molecules and functional group transformations and manipulations, including the use of protective groups, can be obtained from the relevant scientific literature or from standard reference textbooks in the field. Although not limited to any one or several sources, recognized reference textbooks of organic synthesis include: Smith, M. B.; March, J. March's Advanced Organic Chemistry: Reactions, Mechanisms, and Structure, 5$^{th}$ ed.; John Wiley & Sons: New York, 2001; and Greene, T. W.; Wuts, P. G. M. Protective Groups in Organic Synthesis, 3$^{rd}$; John Wiley & Sons: New York, 1999.

Methods for preparing the free base of Compound A is described in U.S. Pat. No. 8,357,694, the entire contents of which are incorporated herein by reference.

Biological Assays

The present application provides methods to assess biological activities of the compounds of the application. In one method, an assay based on enzymatic activity can be utilized. In one specific enzymatic activity assay, the enzymatic activity is from a kinase (e.g., FGFR). As used herein, "kinase" refers to enzymes which catalyze the transfer of the γ-phosphate from ATP to the hydroxyl group on the side chain of Ser/Thr or Tyr in proteins and peptides and are intimately involved in the control of various important cell functions, such as signal transduction, differentiation, and proliferation. Preferably, the kinase assayed is a tyrosine kinase (e.g., FGFR).

A change in enzymatic activity caused by compounds of the present application can be measured in the disclosed assays. The change in enzymatic activity can be characterized by the change in the extent of phosphorylation of certain substrates. As used herein, "phosphorylation" refers to the addition of phosphate groups to a substrate, including proteins and organic molecules, and plays an important role in regulating the biological activities of proteins. Preferably, the phosphorylation assayed and measured involves the addition of phosphate groups to tyrosine residues. The substrate can be a peptide or protein.

In some assays, immunological reagents, e.g., antibodies and antigens, are employed. Fluorescence can be utilized in the measurement of enzymatic activity in some assays. Specific methods for assessing the biological activity of the disclosed compounds are described in the examples.

One skilled in the art may refer to general reference texts for detailed descriptions of known techniques discussed herein or equivalent techniques. These texts include Ausubel et al., Current Protocols in Molecular Biology, John Wiley and Sons, Inc. (2005); Sambrook et al., Molecular Cloning, A Laboratory Manual (3$^{rd}$ edition), Cold Spring Harbor Press, Cold Spring Harbor, N.Y. (2000); Coligan et al., Current Protocols in Immunology, John Wiley & Sons, N.Y.; Enna et al., Current Protocols in Pharmacology, John Wiley & Sons, N.Y.; Fingl et al., The Pharmacological Basis of Therapeutics (1975), Remington's Pharmaceutical Sciences, Mack Publishing Co., Easton, Pa., 18$^{th}$ edition (1990). These texts can, of course, also be referred to in making or using an aspect of the disclosure X-Ray Powder Diffraction (XRPD)
Flat Plate Mode Flat plate mode XRPD analysis was carried out on a Siemens D5000, scanning the samples between 3 and 30 °2-theta. Material was gently compressed on a glass disc inserted into a sample holder. The sample was then loaded into a Siemens D5000 diffractometer running in reflection mode and analyzed, using the following experimental conditions.

| Raw Data Origin | Siemens-binary V2 (.RAW) |
|---|---|
| Start Position [° 2Th.] | 3.0000 |
| End Position [° 2Th.] | 30.0000 |
| Step Size [° 2Th.] | 0.0200 |
| Scan Step Time [s] | 1 |
| Scan Type | Continuous |
| Offset [° 2Th.] | 0.0000 |
| Divergence Slit Type | Fixed |
| Divergence Slit Size [mm] | 2.0000 |
| Specimen Length [mm] | various |
| Receiving Slit Size [mm] | 0.2000 |
| Measurement Temperature [° C.] | 20.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 (nominal) |
| Generator Settings | 40 mA, 40 kV |
| Diffractometer Type | d5000 |
| Diffractometer Number | 0 |
| Goniometer Radius [mm] | 217.50 |
| Incident Beam Monochromator | No |
| Diffracted Beam Monochromator | (Graphite) |
| Spinning | No |

Capillary Mode

Capillary mode XRPD analysis was carried out on a Bruker D8 Advance, scanning the samples between 2 and 50 °2-theta. Material was packed into a 0.7 mm capillary and analyzed in transmission mode using the following experimental conditions.

| Raw Data Origin | BRUKER-binary V3 (.RAW) |
|---|---|
| Scan Axis | Gonio |
| Start Position [° 2Th.] | 2.0000 |
| End Position [° 2Th.] | 50.0000 |
| Step Size [° 2Th.] | 0.0800 |
| Scan Step Time [s] | 5 |
| Scan Type | Continuous |

-continued

| Raw Data Origin | BRUKER-binary V3 (.RAW) |
|---|---|
| Offset [° 2Th.] | 0.0000 |
| Divergence Slit Type | Fixed |
| Divergence Slit Size [°] | 1.0000 |
| Specimen Length [mm] | 10.00 |
| Receiving Slit Size [mm] | 0.1000 |
| Measurement Temperature [° C.] | 25.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 |
| Generator Settings | 40 mA, 40 kV |
| Diffractometer Type | D8 |
| Diffractometer Number | 0 |
| Goniometer Radius [mm] | 280.00 |
| Dist. Focus-Diverg. Slit [mm] | 91.00 |
| Incident Beam Monochromator | No |
| Spinning | Yes |

Bruker AXS C2 GADDS

X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. A weekly performance check is carried out using a certified standard NIST 1976 Corundum (flat plate).

The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample would be exposed to the X-ray beam for 120 seconds. The software used for data collection was GADDS for WNT 4.1.16 and the data were analyzed and presented using Diffrac Plus EVA v 9.0.0.2 or v 13.0.0.2.

Ambient Conditions

Samples run under ambient conditions were prepared as flat plate specimens using powder as received without grinding. Approximately 3-5 mg of the sample was lightly pressed on a glass slide to obtain a flat surface.

Non-Ambient Conditions

Samples run under non-ambient conditions were mounted on a silicon wafer with heat-conducting compound. The sample was then heated to the appropriate temperature at ca. $10°$ C.·min$^{-1}$ and subsequently held isothermally for ca 1 minute before data collection was initiated.

Polarized Light Microscopy (PLM)

The presence of birefringence was determined using an Olympus BX50 polarizing microscope, equipped with a Motic camera and image capture software (Motic Images Plus 2.0). All images were recorded using a 10× or 20× objective, unless otherwise stated.

Alternatively, samples were studied on a Leica LM/DM polarized light microscope with a digital video camera for image capture. A small amount of each sample was placed on a glass slide, mounted in immersion oil and covered with a glass slip, the individual particles being separated as well as possible. The sample was viewed with appropriate magnification and partially polarized light, coupled to a λ false-color filter.

Hot Stage Microscopy (HSM)

The sample was placed in a THM Linkam hot-stage and heated at a rate of 10° C./min from room temperature (ca. 22° C.) to 250° C. Thermal events were monitored visually using an Olympus BX50 microscope, equipped with a Motic camera and image capture software (Motic Images Plus 2.0). All images were recorded using a 10× objective, unless otherwise stated.

Alternatively, Hot Stage Microscopy was carried out using a Leica LM/DM polarized light microscope combined with a Mettler-Toledo MTFP82HT hot-stage and a digital video camera for image capture. A small amount of each sample was placed onto a glass slide with individual particles separated as well as possible. The sample was viewed with appropriate magnification and partially polarized light, coupled to a λ false-color filter, whilst being heated from ambient temperature typically at 10-20° C.·min−1 for 1 minute).

Thermogravimetric/Differential Thermal Analysis (TG/DTA)

Approximately, 5 mg of material was weighed into an open aluminum pan and loaded into a simultaneous thermogravimetric/differential thermal analyzer (TG/DTA) and held at room temperature. The sample was then heated at a rate of 10° C./min from 25° C. to 300° C. during which time the change in sample weight was recorded along with any differential thermal events (DTA). Nitrogen was used as the purge gas, at a flow rate of 100 cm$^3$/min.

Alternatively, TGA data were collected on a Mettler TGA/SDTA 851e equipped with a 34 position auto-sampler. The instrument was temperature calibrated using certified indium. Typically 5-10 mg of each sample was loaded onto a pre-weighed aluminum crucible and was heated at 10° C.·min−1 from ambient temperature to 350° C. A nitrogen purge at 50 ml·min−1 was maintained over the sample.

Differential Scanning calorimetry (DSC)

Approximately, 5 mg of material was weighed into an aluminum DSC pan and sealed non-hermetically with a pierced aluminum lid. The sample pan was then loaded into a Seiko DSC6200 (equipped with a cooler) cooled and held at 25° C. Once a stable heat-flow response was obtained, the sample and reference were heated to 280° C. at scan rate of 10° C./min and the resulting heat flow response monitored.

Alternatively, DSC data were collected on a Mettler DSC 823e equipped with a 34 position auto-sampler. The instrument was calibrated for energy and temperature using certified indium. Typically 0.5-2 mg of each sample, in a pin-holed aluminum pan, was heated at 10° C.·min−1 from 25° C. to 350° C. A nitrogen purge at 50 ml·min$^{-1}$ was maintained over the sample.

Alternatively, modulated DSC data were collected on a TA Instruments Q2000 equipped with a 50 position auto-sampler. The calibration for thermal capacity was carried out using sapphire and the calibration for energy and temperature was carried out using certified indium. Modulated temperature DSC was carried out using an underlying heating rate of 2° C.·min$^{-1}$ and temperature modulation parameters of ±1.27° C.·min$^{-1}$ and 60 seconds.

Karl Fischer Coulometric Titration (KF)

Initially a blank sample containing methanol only was analyzed by KF (Mettler Toledo C30 Compact Titrator) to determine the blank water content before sample analysis. Approximately 10-15 mg of solid material was accurately weighed into a vial. The material was then dissolved in methanol and the amount added was recorded. The resultant was then manually introduced into the titration cell of a Mettler Toledo C30 Compact Titrator. The water content was calculated as a percentage and the data printed.

Dynamic Vapor Sorption (DVS)

Approximately 10 mg of sample was placed into a mesh vapor sorption balance pan and loaded into a DVS-1 dynamic vapor sorption balance by Surface Measurement Systems. The sample was subjected to a ramping profile from 20-90% relative humidity (RH) at 10% increments, maintaining the sample at each step until a stable weight had been achieved (99.5% step completion). After completion of the sorption cycle, the sample was dried using the same procedure from 90-0% RH, and was finally taken back to the starting point of 20% RH. The weight change during the sorption/desorption cycles were plotted, allowing for the hygroscopic nature of the sample to be determined.

Gravimetric Vapor Sorption (GVS)

Sorption isotherms were obtained using a SMS DVS Intrinsic moisture sorption analyzer, controlled by DVS Intrinsic Control software v1.0.0.30. The sample temperature was maintained at 25° C. by the instrument controls. The humidity was controlled by mixing streams of dry and wet nitrogen, with a total flow rate of 200 ml·min$^{-1}$ The relative humidity was measured by a calibrated Rotronic probe (dynamic range of 1.0-100% RH), located near the sample. The weight change, (mass relaxation) of the sample as a function of % RH was constantly monitored by the microbalance (accuracy±0.005 mg). Typically 5-20 mg of sample was placed in a tared mesh stainless steel basket under ambient conditions. The sample was loaded and unloaded at 40% RH and 25° C. (typical room conditions). A moisture sorption isotherm was performed as outlined below (2 scans giving 1 complete cycle). The standard isotherm was performed at 25° C. at 10% RH intervals over a 0-90% RH range. Data analysis was undertaken in Microsoft Excel using DVS Analysis Suite v6.0.0.7.

TABLE 1

Method Parameters for SMS DVS Intrinsic Experiments

| Parameters | Values |
|---|---|
| Adsorption-Scan 1 | 40-90 |
| Desorption/Adsorption-Scan 2 | 90-0, 0-40 |
| Intervals (% RH) | 10 |
| Number of Scans | 2 |
| Flow rate (ml · min$^{-1}$) | 200 |
| Temperature (° C.) | 25 |
| Stability (° C. · min$^{-1}$) | 0.2 |
| Sorption Time (hours) | 6 hour time out |

$^1$H Nuclear Magnetic Resonance ($^1$H NMR)

$^1$H-NMR experiments were performed on a Bruker AV400 (frequency: 400 MHz). Experiments were performed in an appropriate solvent and each sample was prepared to ca. 10 mM concentration.

Focused Beam Reflectance Measurements (FBRM)

Focused beam reflectance measurements were carried out using a Mettler Toledo D600 probe. For each crystallization, the probe was placed into the appropriate reaction vessel at the start of the crystallization and the nucleation and crystal growth was monitored. The chord length distributions and various count statistics were monitored throughout.

Infrared Spectroscopy (IR)

Infrared spectroscopy was carried out on a Bruker ALPHA P spectrometer. Sufficient material was placed onto the center of the plate of the spectrometer and the spectra were obtained using the following parameters:
Resolution: 4 cm$^{-1}$
Background Scan Time: 16 scans
Sample Scan Time: 16 scans
Data Collection: 4000 to 400 cm$^{-1}$
Result Spectrum: Transmittance
Software: OPUS version 6

Ion Chromatography 10 mg samples were weighed, diluted in 5 mL water (or water:methanol {4%}) and then analyzed for chloride content using the following experimental conditions:
Instrument: Dionex Chromatography System
Column: Dionex IonPac AS14A-5 µm, 3×150 mm
Guard Column: Dionex IonPac AG14A-5 µm, 3×30 mm
Mobile Phase: 15 mM Potassium Hydroxide
Flow Rate: 0.6 mL/min
Runtime: 25 minutes
Detector suppression: 50 mA, water regenerant as required
Column Temperature: 30° C.
Injection Volume: 25 µL High Performance Liquid Chromatography-Ultraviolet Detection (HPLC-UV)

Purity was determined by first diluting samples in acetonitrile:water (50%) to 100 mg/mL; solubility was determined by diluting 100 µL saturated solution in 900 µL acetonitrile:water (50%). Samples were then analyzed using the following experimental conditions:

Setting 1:
Instrument: Agilent 1100
Column: Phenomenex Luna C18 5µ 150×4.6 mm LC/031
Column Temperature: 25° C.
Autosampler Temperature: 20° C.
UV wavelength: 255 nm
Injection Volume: 5 µL
Flow Rate: 1 mL/min
Mobile Phase A: 0.1% TFA
Mobile Phase B: 0.085% TFA in Acetonitrile

| Gradient program: | |
|---|---|
| Time (minutes) | Solvent B [%] |
| 0 | 5 |
| 45 | 95 |
| 55 | 95 |
| 55.1 | 5 |
| 60 | 5 |

Setting 2:
Instrument: Agilent 1100
Column: Phenomenex Luna C18 5µ 150×4.6 mm LC/031
Column Temperature: 25° C.
Autosampler Temperature: Ambient
UV wavelength: 280 nm
Injection Volume: 5 µL
Flow Rate: 1 mL/min
Mobile Phase A: 95:5:01% v/v/v/H$_2$O:Methanol:TFA
Mobile Phase B: 95:5:01% v/v/v/Methanol:H$_2$O:TFA

| Gradient program: | | |
|---|---|---|
| Time (minutes) | Solvent A [%] | Solvent B [%] |
| 0.0 | 90 | 10 |
| 8.0 | 65 | 35 |
| 10.0 | 30 | 70 |
| 24.0 | 20 | 80 |
| 30.0 | 5 | 95 |
| 35.0 | 0 | 100 |
| 35.1 | 90 | 10 |
| 40.0 | 90 | 10 |

Single Crystal X-Ray Diffraction (SCXRD)

Data were collected on an Oxford Diffraction Supernova Dual Source, Cu at Zero, Atlas CCD diffractometer equipped with an Oxford Cryosystems Cobra cooling device. The data was collected using CuKα radiation. Structures were typically solved using either the SHELXS or SHELXD programs and refined with the SHELXL program as part of the Bruker AXS SHELXTL suite. Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Thermodynamic Aqueous Solubility

Aqueous solubility was determined by suspending sufficient compound in water to give a maximum final concentration of ≥10 mg·ml$^{-1}$ of the parent free-form of the compound. The suspension was equilibrated at 25° C. for 24 hours then the pH was measured. The suspension was then filtered through a glass fiber C filter into a 96 well plate. The filtrate was then diluted by a factor of 101. Quantitation was by HPLC with reference to a standard solution of approximately 0.1 mg·ml$^{-1}$ in DMSO. Different volumes of the standard, diluted and undiluted sample solutions were injected. The solubility was calculated using the peak areas determined by integration of the peak found at the same retention time as the principal peak in the standard injection.

Pharmaceutical Compositions

The present application also provides pharmaceutical compositions comprising one or more compounds of the present application (e.g., solid forms, amorphous forms, crystalline forms, and polymorphs of Compound A) in combination with at least one pharmaceutically acceptable excipient or carrier.

A "pharmaceutical composition" is a formulation containing the compounds of the present application in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the one or more of the disclosed compounds) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical compositions of the present application is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the present application can be administered to a subject in many of the well-known methods currently used for chemotherapeutic treatment. For example, for treatment of cancers, a compound of the present application may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved.

In therapeutic applications, the dosages of the pharmaceutical compositions used in accordance with the disclosure vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present application are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound employed. An ordinarily skilled physician or veterinarian can readily determine and prescribe the effective amount of the drug required to prevent, counter or arrest the progress of the condition.

Techniques for formulation and administration of the disclosed compounds of the disclosure can be found in *Remington: the Science and Practice of Pharmacy*, 19th edition, Mack Publishing Co., Easton, Pa. (1995). In an embodiment, the compounds described herein, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present application are apparent from the different examples. The provided examples illustrate different components and methodology useful in practicing the present application. The examples do not limit the present application. Based on the present application the skilled artisan can identify and employ other components and methodology useful for practicing the present application.

Methods of Treatment

The present application provides methods for the treatment of a cell proliferative disorder in a subject in need thereof by administering to the subject a therapeutically effective amount of one or more compounds of the present application (e.g., solid forms, amorphous forms, crystalline forms, or polymorphs). The present application also provides methods of protecting against a cell proliferative disorder in a subject in need thereof by administering to the subject a therapeutically effective amount of one or more compounds of the present application (e.g., solid forms, amorphous forms, crystalline forms, or polymorphs). The cell proliferative disorder can be cancer or a precancerous condition. The present application further provides the use of one or more compounds of the present application for the preparation of a medicament useful for the treatment or prevention of a cell proliferative disorder.

As used herein, a "subject in need thereof" is a subject having a cell proliferative disorder, or a subject having an increased risk of developing a cell proliferative disorder relative to the population at large. A subject in need thereof can have a precancerous condition. Preferably, a subject in need thereof has cancer. A "subject" includes a mammal. The mammal can be any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue.

A cell proliferative disorder includes a precancer or a precancerous condition. A cell proliferative disorder includes cancer. Preferably, the methods provided herein are used to treat or alleviate a symptom of cancer.

The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

As used herein, "treating" or "treat" describes the management and care of a patient for the purpose of combating a disease, condition, or disorder, and includes the administration of a compound of the present application to alleviate the symptoms or complications of a disease, condition or disorder, or to eliminate the disease, condition or disorder.

As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of a compound of the present application leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "symptom" is defined as an indication of disease, illness, injury, or that something is not right in the body. Symptoms are felt or noticed by the individual experiencing the symptom, but may not easily be noticed by others.

As used herein, the term "sign" is also defined as an indication that something is not right in the body. However, signs are defined as things that can be seen by a doctor, nurse, or other health care professional.

EXAMPLES

Example 1: Hydration Screening of the Solid Forms of the Present Application

The hydration screen was carried out using a temperature range which emulated the temperature conditions employed during the crystallization process. The solvent used, and the results are summarised in Table 2.

TABLE 2

Summary of hydration screen carried out in acetone, 2-propanol and acetonitrile at 10° C., 25° C. and 50° C.

| Temp. (° C.) | Water activity | Acetone | |
|---|---|---|---|
| | | Thin slurry | Thick slurry |
| 10 | 0.10 | Form D | Form D |
| | 0.20 | Form D | Form D |
| | 0.30 | Form D | Form D |
| | 0.50 | Form D | Form D |
| | 0.70 | Form D | Form D |
| | 0.90 | Form G    Form D | Form D |
| 25 | 0.10 | Form D | Form D |
| | 0.20 | Form D | Form D |
| | 0.30 | Form D | Form D |
| | 0.50 | Form D | Form D |
| | 0.70 | Form D | Form D |
| | 0.90 | Form G | Form D |

TABLE 2-continued

Summary of hydration screen carried out in acetone,
2-propanol and acetonitrile at 10° C., 25° C. and 50° C.

| 50 | 0.10 | Form D | Form D |
| | 0.20 | Form D | Form D |
| | 0.30 | Form D | Form D |
| | 0.50 | Form D | Form D |
| | 0.70 | Form D | Form D |
| | 0.90 | Form D | Form D |

2-Propanol

| Temp. (° C.) | Water activity | Thin slurry | Thick slurry |
|---|---|---|---|
| 10 | 0.20 | Form D | Form D |
| | 0.40 | Form D | Form D |
| | 0.52 | Form D | Form D |
| | 0.60 | Form D | Form D |
| | 0.70 | Form D | Form D |
| | 0.91 | Form D | Form D |
| 25 | 0.20 | Form D | Form D |
| | 0.35 | Form D | Form D |
| | 0.53 | Form D | Form D |
| | 0.60 | Form D | Form D |
| | 0.70 | Form D | Form D |
| | 0.91 | Form G | Form G |
| 50 | 0.20 | Form A   Form D | Form G   Form G |
| | 0.29 | Form A   Form D | Form D |
| | 0.51 | Form D | Form D |
| | 0.60 | Form D | Form D |
| | 0.71 | Form G | Form G |
| | 0.91 | Form G | Form G |

Acetonitrite

| Temp. (° C.) | Water activity | Thin slurry | Thick slurry |
|---|---|---|---|
| 10 | 0.11 | Form D | Form D |
| | 0.24 | Form D | Form D |
| | 0.40 | Form D | Form D |
| | 0.59 | Form D | Form D |
| | 0.69 | Form D | Form D |
| | 0.89 | Form G   Form D | Form D |
| 25 | 0.11 | Form D | Form D |
| | 0.23 | Form D | Form D |
| | 0.39 | Form D | Amorphous |
| | 0.57 | Form D | Amorphous |
| | 0.72 | Form D | Form D |
| | 0.90 | Form G   Form D | Form D |
| 50 | 0.10 | Form A | Form D |
| | 0.21 | Form D | Form D |
| | 0.36 | Form D | Form D |
| | 0.53 | Form D | Form D |
| | 0.73 | Form D | Form D |
| | 0.90 | Form D | Form D |

Example 2: Preparation and Characterization of an Amorphous Form of Compound A

Figure 2:
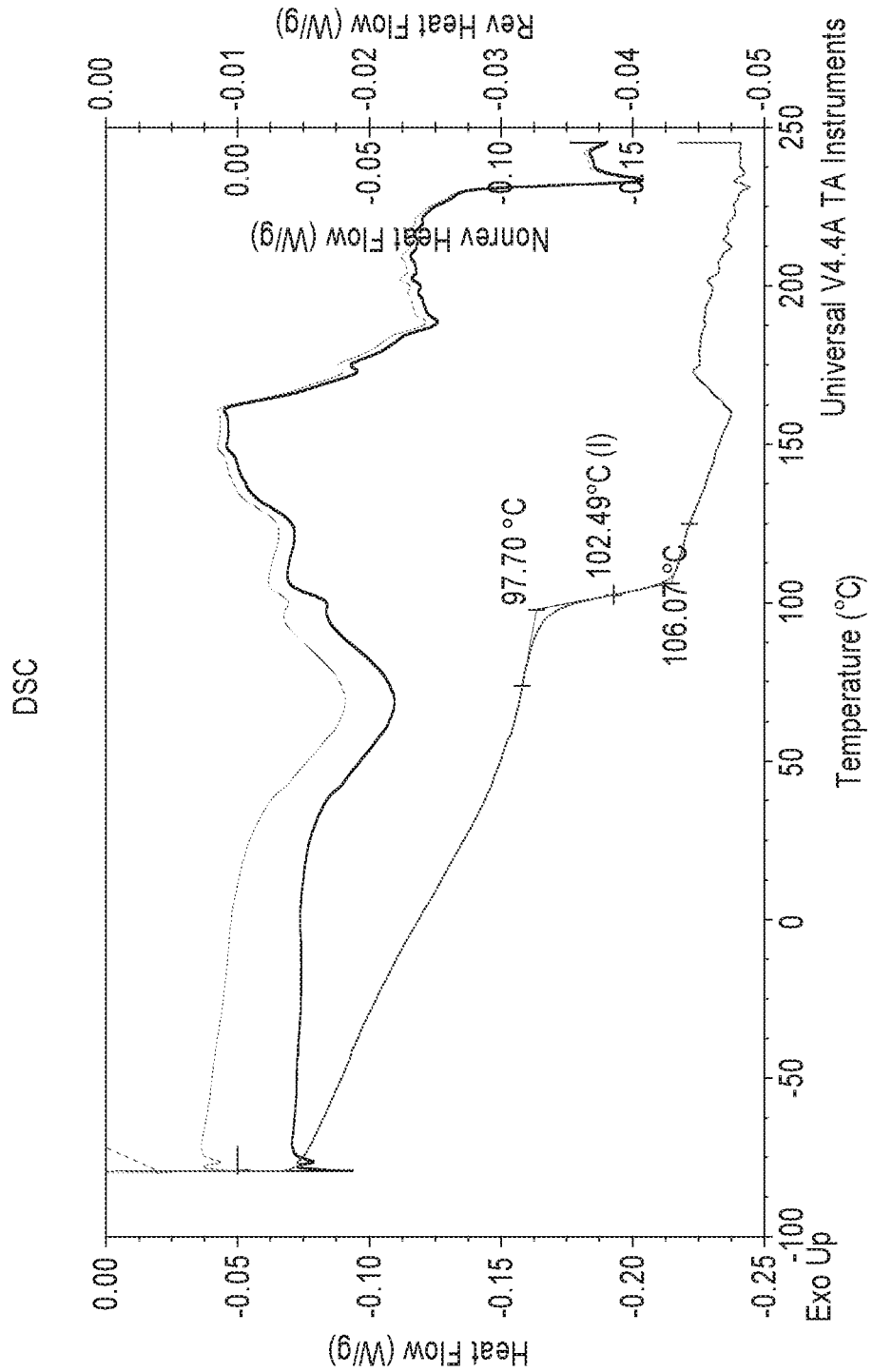
FIG. 2 sets forth thermal analysis by DSC of an amorphous form of Compound A.

Approximately 4 g of Compound A was weighed into a vessel and was dissolved in ca. 50 mL deionised water. The resultant solution was placed at ca. −20° C. until completely frozen and was then removed to a freeze dryer for a minimum of 24 h. The resultant solid material was analyzed by PLM and XRPD. The XRPD of the amorphous form is shown in FIG. 1.

Modulated DSC analysis of the amorphous form was carried out to determine the glass transition ($T_g$). The glass transition temperature of an amorphous material is the temperature at which the molecules and atoms of this material relax and acquire a degree of mobility which will allow them to crystallize. Below this glass transition temperature, the material will remain amorphous and crystallization will not occur. The glass transition was observed as a step in the reversible heat flow thermogram due to a change in the heat capacity of the material (shown in FIG. 2). For Compound A, the glass transition temperature was established at 102° C.

Figure 3:
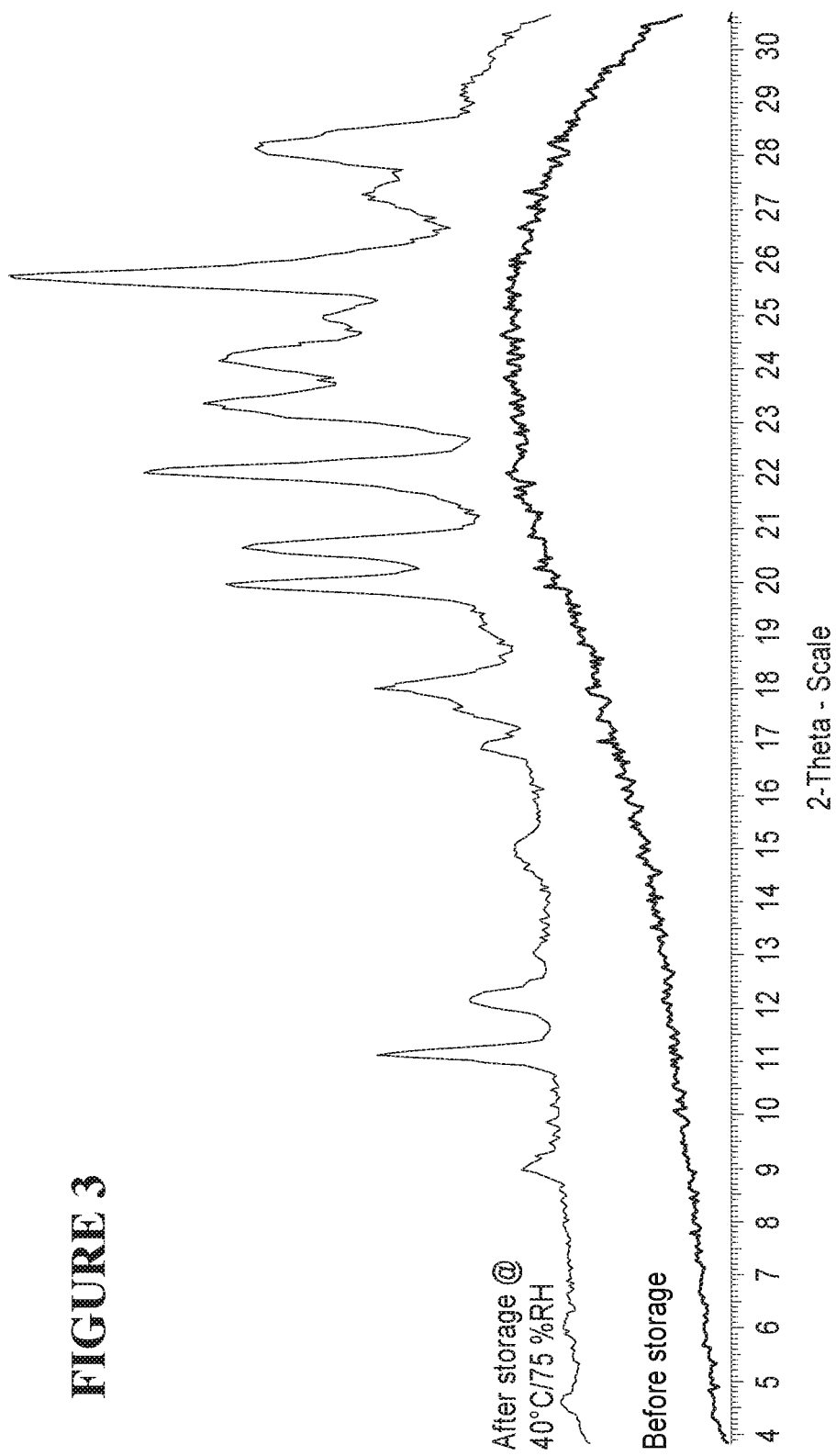
FIG. 3 sets forth X-ray powder diffraction patterns of an amorphous form of Compound A before and after storage at 40° C. and 75% RH.

The amorphous form was stored in the humidity chamber at 40° C. and 75% RH. As shown in the XRPD in FIG. 3, after 6 days the amorphous form was converted to a crystalline form having an XRPD pattern similar to that of Form F.

Example 3: Preparation and Characterization of Form A 100 mg Scale Preparation

Approximately 100 mg of amorphous Compound A was slurried at 50° C. in 1.66 mL of each of the solvent systems listed in Table 3. The slurries were then temperature cycled with continuous agitation in 4 hour cycles for a period of ca. 72 hours (slurries were held at 50° C. for 4 hours followed by a hold at ambient for 4 hours, the cooling/heating rates after the 4 hour hold periods was ca. 1° C./min). Solid material was then recovered and allowed to dry at ambient conditions prior to analysis by XRPD.

TABLE 3

Form A Scale-up solvents

| Solvent | Solvent Class |
|---|---|
| Acetone | 3 |
| 1,4-Dioxane | 2 |
| Ethanol | 3 |

500 mg Scale Preparation

Approximately 500 mg of amorphous Compound A was slurried at 50° C. in 8.4 mL ethanol and then temperature cycled, with continuous agitation, in 4 hour cycles for a period of ca. 72 hours (slurries were held at 50° C. for 4 hours followed by a hold at ambient for 4 hours, the cooling/heating rates after the 4 hour hold periods was ca. 1° C./min). Solid material was then recovered by filtration and allowed to dry at ambient conditions prior to analysis by XRPD, KF, TG/DTA and IC.

Characterization

Figure 5:
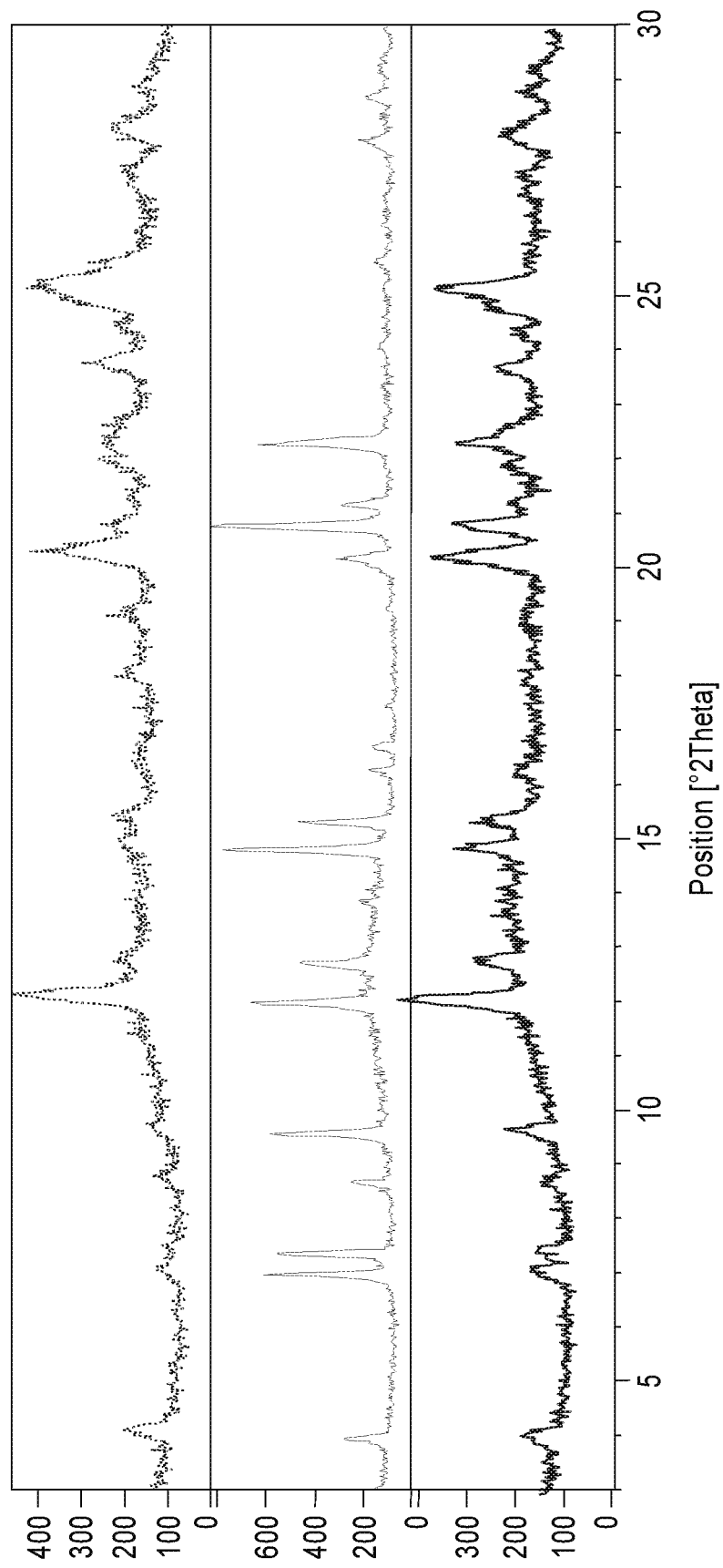
FIG. 5 sets forth X-ray powder diffraction patterns of Form A from an initial hydration screen sample (top panel), and a scale up sample before drying (middle panel) and after drying (bottom panel).

The XRPD of Form A is shown in FIG. 5. Thermal analysis by TGA (FIG. 6A) showed three weight losses of 1.38% between ca. 25° C. and ca. 60° C., 1.49% between ca. 60° C. and 110° C. and 2.23% between 110° C. and 170° C., possibly due to several hydration steps and unbound solvent, as 1 mole equivalent of water is approximately 3.3%. Thermal analysis by DTA (FIG. 6A) showed three endotherms corresponding to the weight losses with onset 39.6° C. (peak ca. 52° C.), 72.2° C. (peak ca. 87° C.) and 142.8° C. (peak ca. 163° C.). A fourth smaller and sharper endotherm is observed with onset 111.7° C. (peak 114° C.). KF coulometric titration measured the water content as approximately 9% (±0.5%), which is higher than the 5.2% weight loss observed by TG/DTA and suggests that Form A may be hygroscopic. Ion chromatography indicated that the ratio of HCl to free base was approximately 1.8:1.

Form A was stored at 40° C./75% RH and 25° C./96% RH for one week and analyzed by XRPD. In both cases, the crystalline pattern remained unchanged, as shown in FIG. 4A or 4B.

Figure 6B:
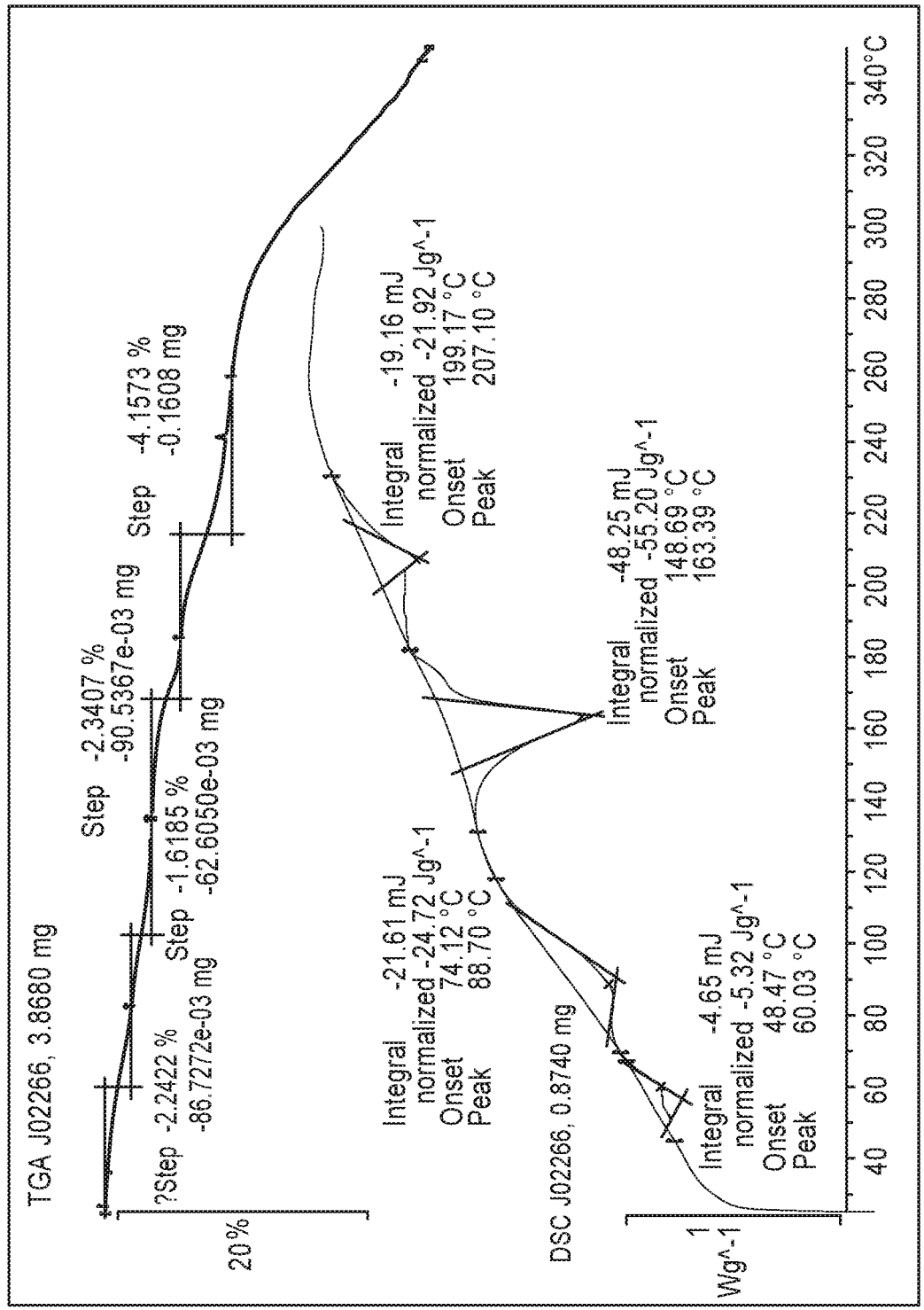
FIG. 6B sets forth thermal analysis by DSC and TG of Form A.

Additional TGA and DSC analysis of Form A confirmed that Form A exhibited complex thermal behavior. Four weight losses were observed in the TGA thermogram between room temperature and 240° C. Each one of these weight losses was associated with at least one endothermic event in the DSC thermogram. The shape of some of these events suggested more than one transformation occurring simultaneously (FIG. 6B).

Figure 7:
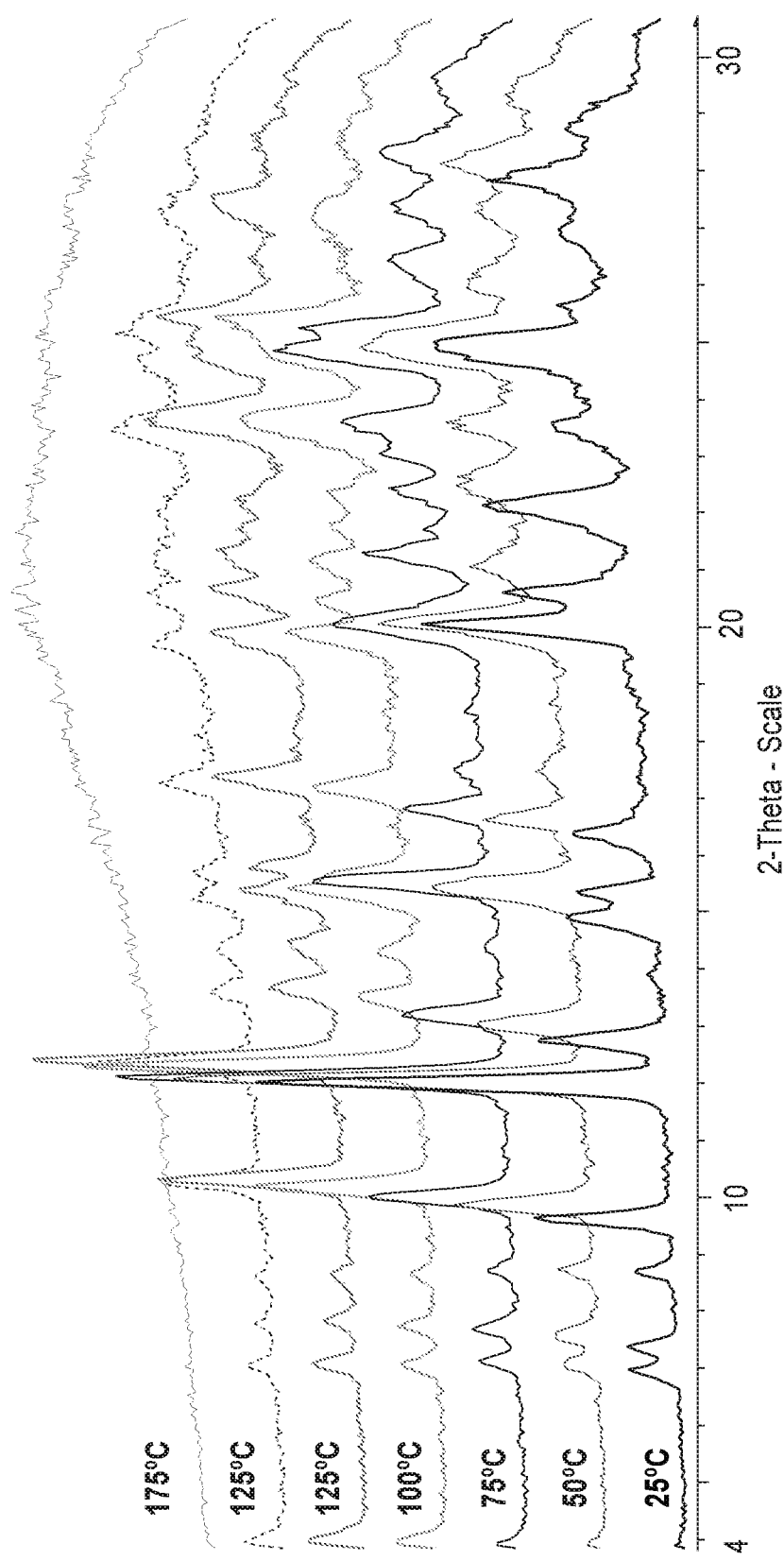
FIG. 7 sets forth X-ray powder diffraction patterns of Form A under different temperatures.

When treated under increasing temperature, Form A is converted to Form E, as demonstrated by variable temperature (VT) XRPD experiments (FIG. 7). Form E reverted to the Form A at ambient conditions (FIG. 8). The presence of water in the crystalline structure of Form A was confirmed by Karl-Fischer water determination (4.03% w/w-average over three measurements).

Figure 9:
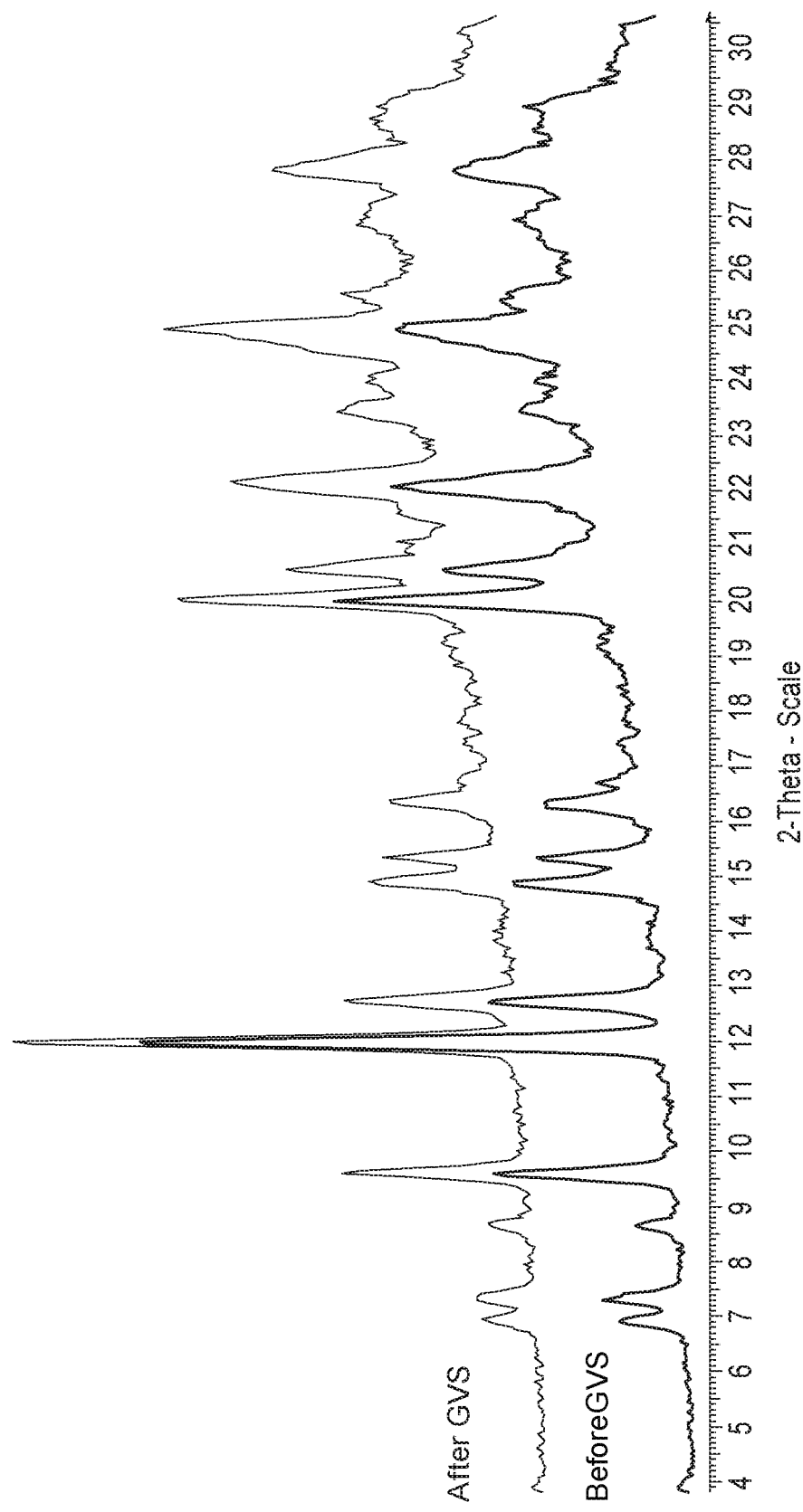
FIG. 9 sets forth X-ray powder diffraction patterns of Form A before and after GVS.

As shown in a GVS experiment, Form A displayed moderate hygroscopicity between 0 and 70% RH at 25° C. (~2.5% w/w), but a significant increase in water uptake was observed between 70 and 90% RH at 25° C. (~5% w/w). The water uptake observed was reversible with hysteresis evident on desorption. This phenomenon is commonly associated with the presence of meosporisity. Also, no significant changes were observed in the crystalline pattern of the sample after the GVS experiment (FIG. 9). However, the high water uptake at 90% RH suggested the existence of a metastable hydrated form which could not be isolated at ambient conditions.

Thermodynamic aqueous solubility was also measured. The sample dissolved completely in water at room temperature (>20 mg/ml) but formed a gel which was very difficult to handle, yielding an unexpectedly low thermodynamic aqueous solubility value (1.09 mg/ml).

Example 4: Preparation and Characterization of Form C

Figure 11:
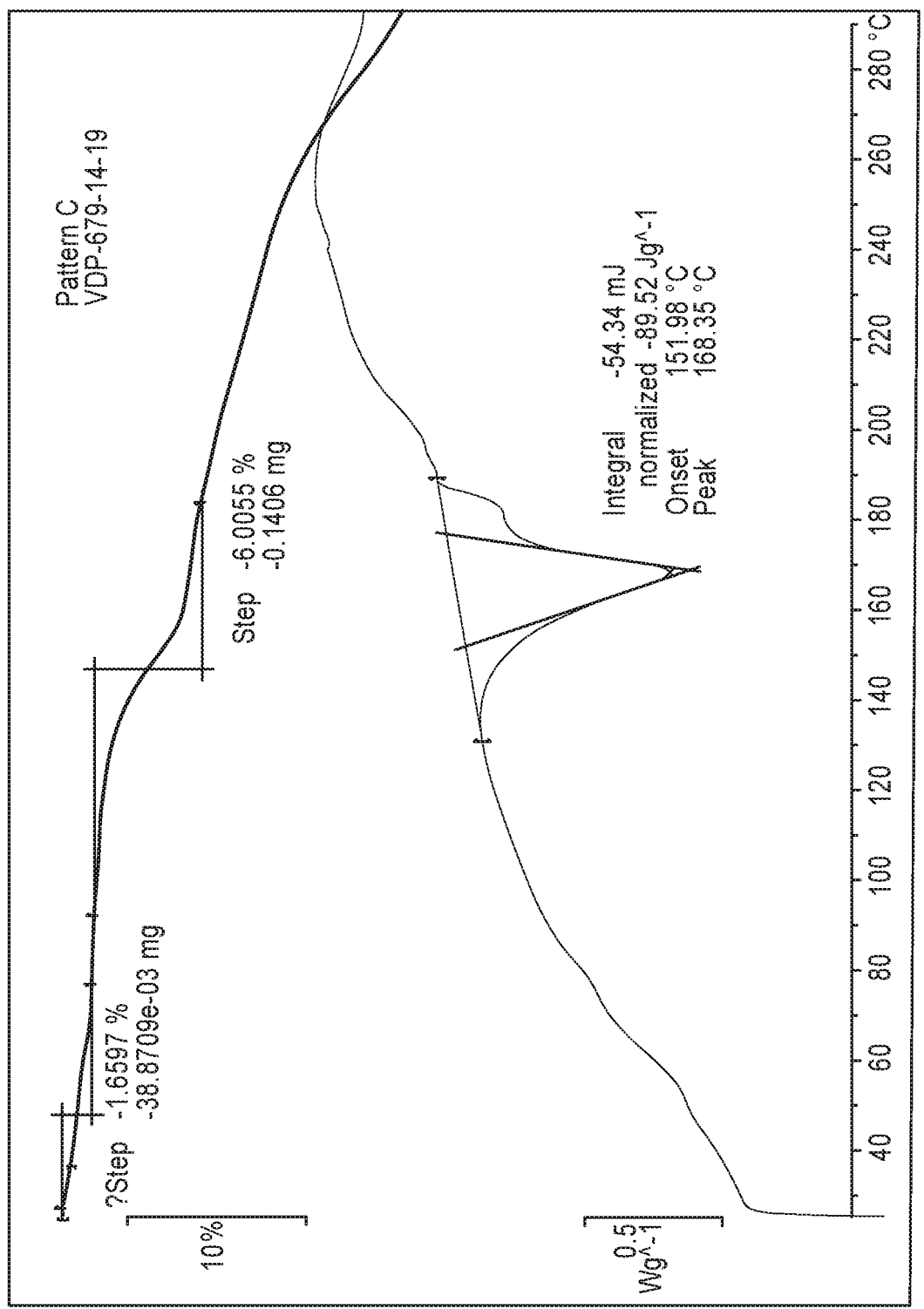
FIG. 11 sets forth a DSC thermogram and a TG analysis of Form C.

Form C was obtained by slow evaporation/crystallization from DMSO. The XRPD analysis of Form C was shown in FIG. 10. TGA thermogram of Form C showed an initial weight loss probably due to residual, unbound DSMO (FIG. 11). The second weight loss, which is associated to a large endotherm in the DSC experiment and occurred just before degradation started, was possible due to solvent in the crystalline structure (FIG. 11). $^1$H-NMR spectrum of Form C heated to 100° C. confirmed that the solvent was DMSO (0.5 mole of DMSO per mole of API).

Figure 12:
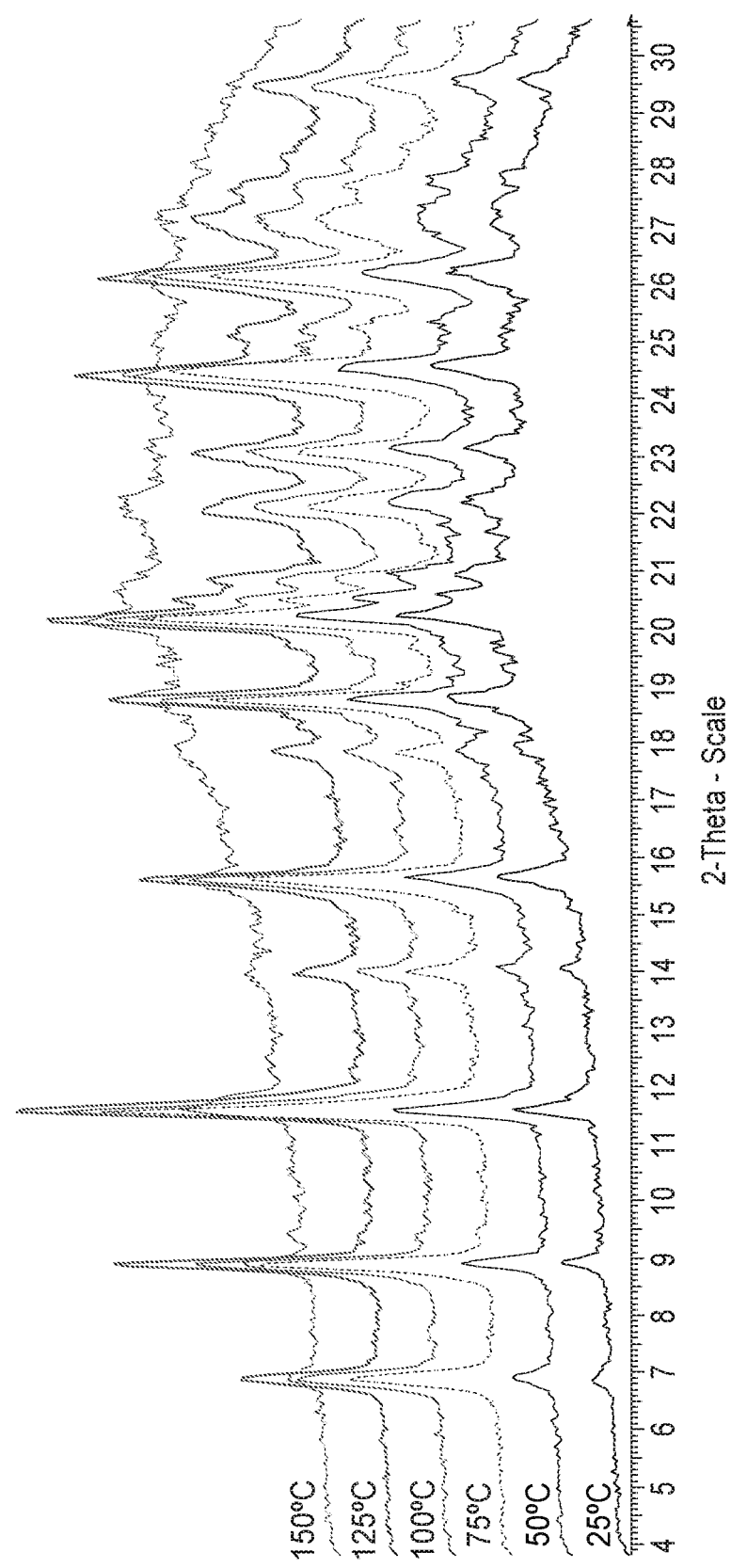
FIG. 12 sets forth X-ray powder diffraction patterns of Form C under different temperatures.

VT-XRPD analysis was carried out on Form C. As shown in FIG. 12, an increase in crystallinity was observed as the sample was heated from room temperature to 75° C. and above. This was thought to be owing to the removal of unbound, residual DMSO occurring upon heating. At 150° C., the material became amorphous (possibly desolvation followed by degradation).

Example 5: Preparation and Characterization of Form D 600 mg Scale Preparation and Characterization Approximately 600 mg of amorphous Compound A was slurried at room temperature, ca. 22° C. in 7.14 mL acetone:water ($W_A$=0.4) with continuous agitation for a period of ca. 6 days. Solid material was then recovered and allowed to dry at ambient conditions prior to analysis.

Figure 16A:
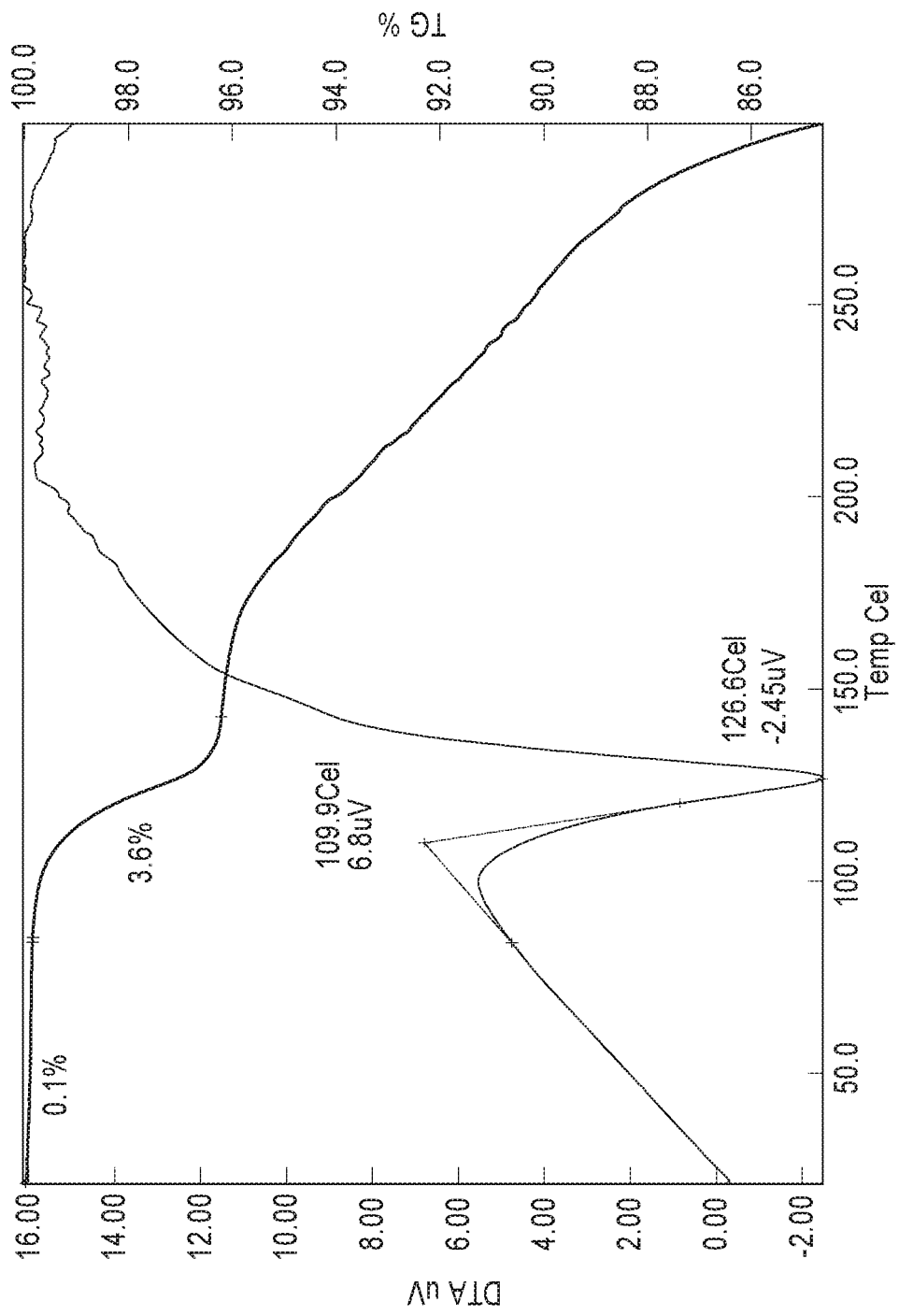
FIG. 16A sets forth thermal analysis by DTA and TG of Form D.

XRPD of Form D is shown in FIG. 13A or 13B. Thermal analysis by TGA showed a single weight loss of 3.6% between ca. 80° C. and ca. 130° C., corresponding approximately to 1 mole equivalent water (3.3%) (FIG. 16A). Thermal analysis by DTA showed a single endotherm with onset 109.9° C. (peak ca. 127° C.), corresponding to the observed weight loss (FIG. 16A). KF coulometric titration measured the water content as approximately 3.9% (±0.5%), which corresponds approximately to the weight loss observed by TG/DTA. Ion chromatography indicated that the ratio of HCl to free base was approximately 1.8:1.

Preparation of Form D and Characterization

Alternatively, approximately 139.5 mg Compound A was dissolved in 2 mL of acetone:water (85:15%) at 50° C. Approximately 4 mL of acetone was added slowly at 50° C. to achieve an acetone:water composition of 95:5%. A small portion of the slurry was filtered at 50° C. and concentration was determined by HPLC analysis; the isolated solid material was characterized by XRPD and PLM. The reaction mixture was then cooled to 20° C. over 1 hour. A small portion of the slurry was filtered at 20° C. and concentration was again determined by HPLC analysis; the isolated solid material was characterized by XRPD and PLM.

TABLE 4

Solubility and polymorphic form results

| Solvent System & Temperature | Solubility | Solid Form | Morphology |
|---|---|---|---|
| Acetone:water (95:5%) at 50° C. | 2.5 mg/mL | Form D | Rod-like |
| Acetone:water (95:5%) at 20° C. | 1.7 mg/mL | Form D | Rod-like |

Preparation with Form D Seed (Crystallization 1) and Characterization

Approximately 8.0 g of Compound A was placed into a 1 L controlled laboratory reactor (CLR) and 114.70 mL of acetone:water (85:15%) was added to the reactor. The reaction mixture was agitated at 270-275 rpm, and heated to 50° C. to dissolve the material. At 50° C., anti-solvent (acetone) was initially added at a rate of 6.25 vol./hour (50 mL/hour). At an acetone: water (88.5:11.5%) composition, the process was seeded with 1% seed (Form D, un-micronized). After the addition of the seed, the anti-solvent addition was stopped and the process was aged for ca. 30 minutes. Further anti-solvent was then added at a rate of 3.75 vol./hour (30 mL/hour) in order to allow for crystal growth. Finally, after reaching an acetone:water (92.9:7.08%) composition, anti-solvent was added at a rate of 7.5 vol./hour (60 mL/hour) until an acetone: water composition of 95:5% was reached. The crystallization was then cooled down from 50° C. to 20° C. at a rate of 0.25° C./min. After reaching 20° C., the slurry was aged for 15 minutes prior to filtration. The filtration was carried out on Buchner funnel having a plate diameter of 80 mm and perforated area diameter of 55 mm using Whatman filter paper 1. The filtration was very fast, taking ca. 1 minute 20 seconds to filter ca. 344 mL of reaction mixture. The wet cake was slurry washed on the filter using 50 mL (6.25 vol) of acetone. The filtered material was then dried on the filter, after which it was dried under vacuum at ambient temperature (ca. 22° C.) for ca. 40 hours, with intermittent mixing.

Figure 16B:
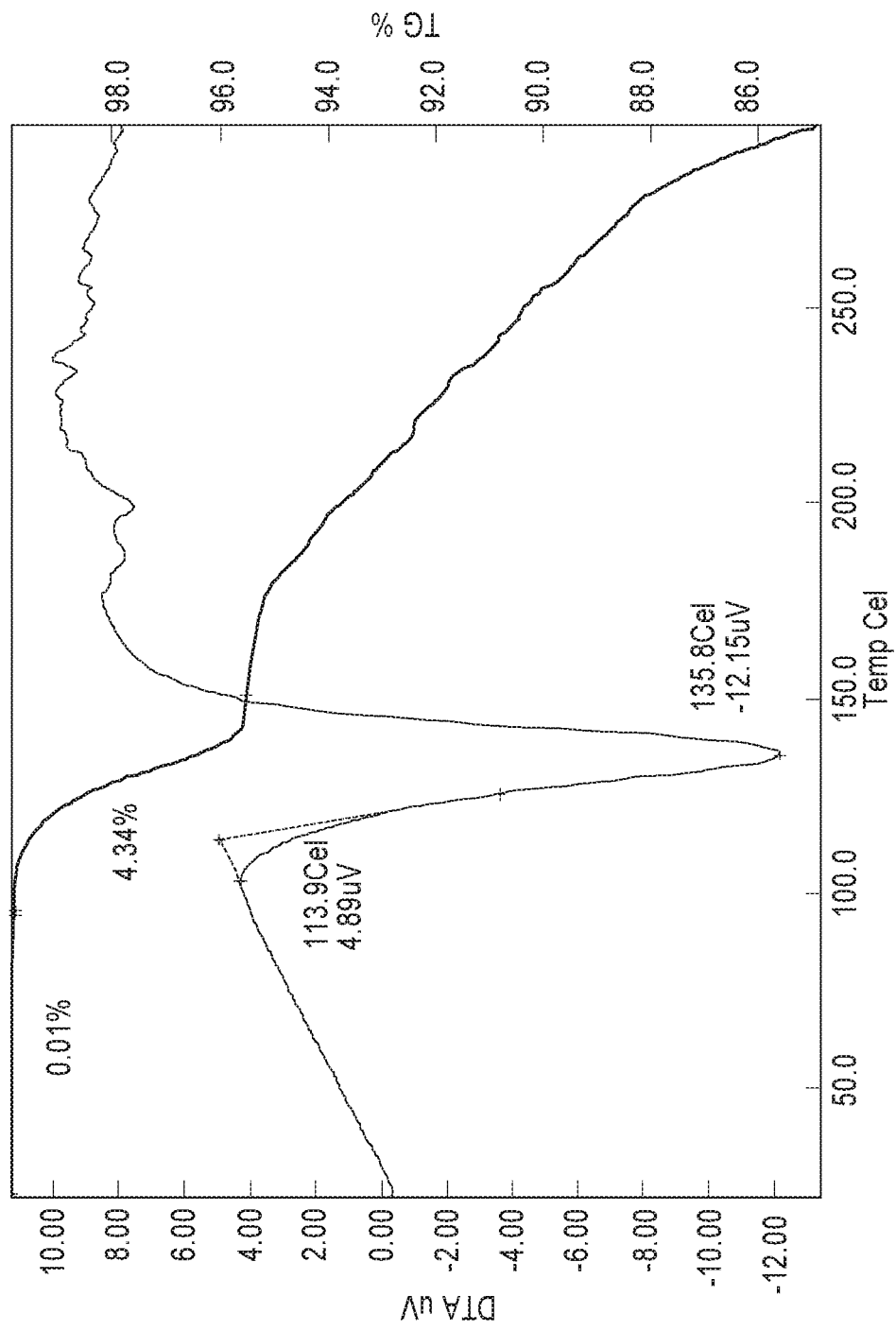
FIG. 16B sets forth thermal analysis by DTA and TG of Form D.

PLM analysis was carried out at various points throughout the crystallization and indicated significant growth on the crystals from the point of seeding. At the end of the crystallization, larger rod-like crystals were obtained with lengths greater than 150 XRPD analysis carried out at various points during the crystallization indicated that Form D was observed throughout the crystallization process. Thermal analysis by TG after drying showed a single weight loss of 4.3% between ca. 90° C. and 160° C. (1 mole equivalent water: 3.3%) (FIG. 16B), confirming the formation of Form D. Thermal analysis by DTA showed a broad endotherm, with onset 113.9° C. (peak ca. 135.8° C.), corresponding to the weight loss (FIG. 16B). HPLC purity analysis indicated a purity of 99.87%. The isolated yield was observed to be 86%, with the HPLC yield being 91%. Karl Fischer analysis indicated a 3.97 (±0.5) % water content.

Preparation with Form D Seed (Crystallization 2) and Characterization

Approximately 8.0 g of Compound A was placed into a 1 L controlled laboratory reactor and 114.70 mL of acetone:water (85:15%) was added to the reactor. The reaction mixture was agitated at 270-275 rpm. The reaction mixture was heated to 50° C. to dissolve the material. At 50° C., anti-solvent (acetone) was added at a rate of 12.5 vol./hour (100 mL/hour) throughout the crystallization. At an acetone:water (88.5:11.5%) composition, the process was seeded with 1% seed (Form D, un-micronized). After the addition of the seed, the anti-solvent addition was stopped and the process was aged for ca. 60 minutes. Further anti-solvent was then added at a rate of 12.5 vol./hour (100 mL/hour) until reaching an acetone:water (95:5%) composition. The crystallization was then cooled down from 50° C. to 20° C. at a rate of 0.25° C./min. After reaching 20° C., the slurry was aged for 60 minutes prior to filtration. The filtration was carried out on Buchner funnel having plate diameter of 80 mm and perforated area diameter of 55 mm using Whatman filter paper 1. The filtration was very fast, taking ca. 1 minute 20 seconds to filter ca. 344 mL of reaction mixture. The wet cake was slurry washed on the filter using 50 mL (6.25 vol) of acetone. The filtered material was then dried on the filter, after which it was dried under vacuum at ambient temperature (ca. 22° C.) for ca. 40 hours, with intermittent mixing.

Figure 16C:
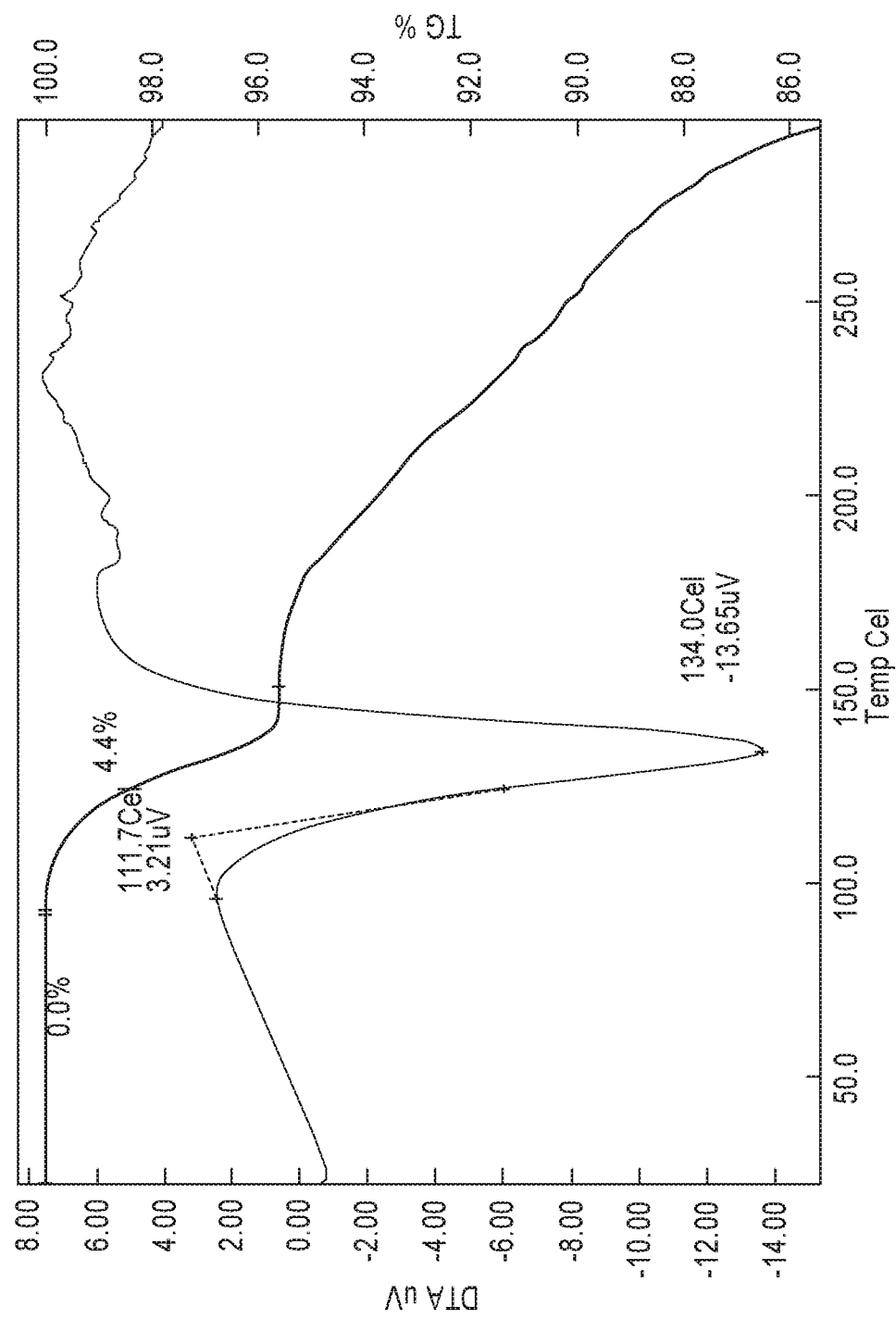
FIG. 16C sets forth thermal analysis by DTA and TG of Form D.

PLM analysis was carried out at various points throughout the crystallization and indicated significant growth on the crystals from the point of seeding. At the end of the crystallization, larger rod-like crystals were obtained with lengths greater than 150 XRPD analysis carried out at various points during the crystallization indicated that Form D was observed throughout the crystallization process. Thermal analysis by TG showed a single weight loss of 4.4% between ca. 90° C. and 160° C. (1 mole equivalent water: 3.3%) (FIG. 16C), confirming the formation of Form D. Thermal analysis by DTA showed a broad endotherm, with onset 111.7° C. (peak ca. 134.0° C.), corresponding to the weight loss (FIG. 16C). HPLC purity analysis indicated a purity of 99.86%. The isolated yield was observed to be 86%, with the HPLC yield being 92%. Karl Fischer analysis indicated a 4.73 (±0.5)% water content.

Preparation with Form D Seed (Crystallization 3) and Characterization

Approximately 8.0 g of Compound A was placed into a 1 L controlled laboratory reactor and 114.70 mL of acetone:water (85:15%) was added to the reactor. The reaction mixture was agitated at 270-275 rpm. The reaction mixture was heated to 50° C. to dissolve the material. At 50° C., anti-solvent (acetone) was added at a rate of 6.25 vol./hour (50 mL/hour) throughout the experiment. At an acetone:water (88.5:11.5%) composition, the process was seeded with 1% micronized seed (Form D). After the addition of the seed, the anti-solvent addition was stopped and the process was aged for ca. 60 minutes. The crystallization was then cooled down from 50° C. to 20° C. at a rate of 0.25° C./min. After reaching 20° C., the slurry was aged for 60 minutes prior to filtration. The filtration was carried out on Buchner funnel having plate diameter of 80 mm and perforated area diameter of 55 mm using Whatman filter paper 1. The filtration was very fast, taking ca. 2 minutes 2 seconds to filter ca. 344 mL of reaction mixture. The wet cake was slurry washed on the filter using 50 mL (6.25 vol) of acetone. Material was then dried on the filter, after which it was dried under vacuum at ambient temperature (ca. 22° C.) for ca. 40 hours, with intermittent mixing.

Figure 16D:
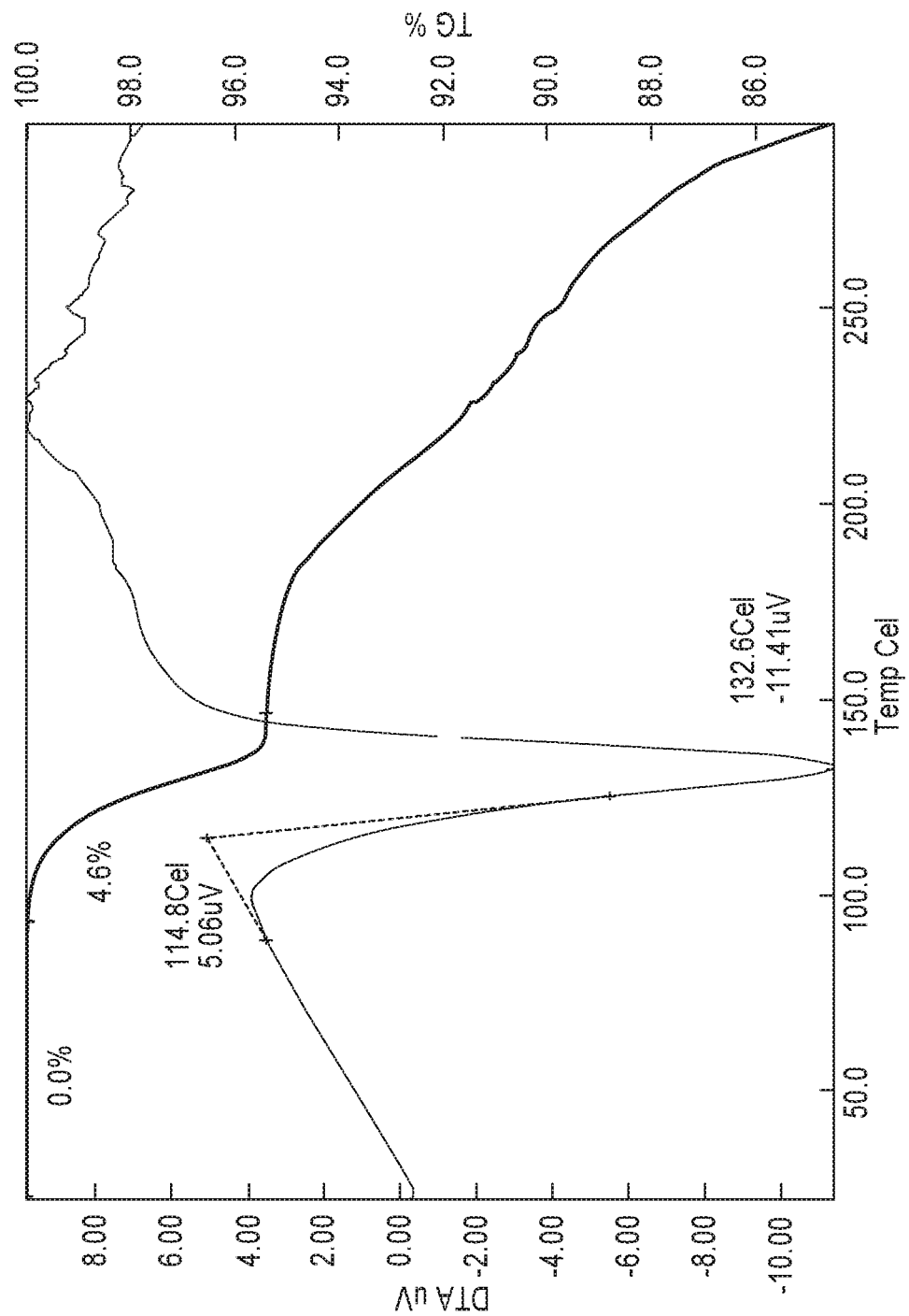
FIG. 16D sets forth thermal analysis by DTA and TG of Form D.

PLM analysis was carried out at various points throughout the crystallization and indicated significant growth from the point of seeding. At the end of the crystallization, rod-like crystals were obtained which were smaller than those obtained from Crystallization 1 and Crystallization 2. XRPD analysis carried out at various points during the crystallization indicated that Form D was observed throughout the crystallization process. Thermal analysis by TG showed a single weight loss of 4.6% between ca. 90° C. and 160° C. (1 mole equivalent water: 3.3%) (FIG. 16D), confirming the formation of Form D. Thermal analysis by DTA showed a broad endotherm, with onset 114.8° C. (peak ca. 132.6° C.), corresponding to the weight loss (FIG. 16D). HPLC purity analysis indicated a purity of 99.89%. The isolated yield was observed to be 89%, with the HPLC yield being 92%. Karl Fischer analysis indicated a 4.45 (±0.5)% water content.

Conversion of Form G to Form D and Characterization

Approximately 5 g of Form G material was slurried in 100 mL acetone:water (98:2%) at 50° C. for 4 days. The conversion of Form G to Form D was monitored by XRPD with samples removed for analysis at 1.5 hours, 3 hours, 19 hours, 1 day, 2 days, and 4 days. The resultant solid material was then filtered, washed with acetone and dried under vacuum. The yield was calculated from the resulting dry material. The dried Form D material was characterized by XRPD, PLM, TG/DTA and KF.

TABLE 5

Results of XRPD monitoring of Form G to Form D conversion

| Analysis Time Point | Form |
| --- | --- |
| 1.5 hours | Form G |
| 3 hours | Form G |
| 19 hours | Form G |
| 1 day | Form G |
| 2 days | Form G |
| 4 days | Form D |

The filtered, washed, and dried Form D material converted from Form G was observed to have undergone a colour change from pale yellow (Form G) to bright yellow (Form D). The isolated yield is 89.1%, and the HPLC calculated yield (from filtrate concentration) is 99.1%. XRPD, shown in FIG. 13A, showed no change in Form D and no loss in crystallinity. Analysis by PLM showed birefringent particles of rod-like morphology. Thermal analysis by TGA showed a single weight loss of 3.5% between ca. 90° C. and 145° C., corresponding approximately to 1 mole equivalent water (3.3%) and consistent with previous Form D material. Thermal analysis by DTA showed a broad endotherm, with onset ca.112.1° C. (peak ca. 133° C.), corresponding to the observed weight loss. A second endotherm was observed at peak ca. 160° C. KF coulometric titration measured the water content as approximately 3.6% (±0.5%), corresponding approximately to the weight loss observed by TG/DTA. Purity analysis by HPLC indicated a purity of 99.9%.

Conversion of Form G to Form D Using Form D Seed

2% Form D Seed

Approximately 5 g of Form G material was slurried in 200 mL acetone:water (99:1%) and approximately 100 mg Form D seed crystals (un-micronized) (2% by mass) were added to the slurry. The slurry was stirred at 50° C. for 5.5 hours and the conversion of Form G to Form D was monitored by XRPD with samples removed for analysis at the following time points: 1 hour, 2 hours, 2.5 hours, 3.5 hours, 4.5 hours, 5 hours, and 5.5 hours. The resultant solid material was then filtered and dried under vacuum. The yield was calculated from the resulting dry material.

TABLE 6

Results of XRPD monitoring of Form G to Form D conversion, using 2% Form D seed

| Analysis Time Point | Form |
|---|---|
| 1 hour | Form G |
| 2 hours | Form G |
| 2.5 hours | Form G |
| 3.5 hours | Form G |
| 4.5 hours | Form G |
| 5 hours | Form D with traces of Form G |
| 5.5 hours | Form D |

The filtered and dried Form D material converted from Form G was observed to have undergone a colour change from pale yellow (Form G) to bright yellow (Form D). The isolated yield is 95.2% (some losses of solid to vessel and during filtration), and the HPLC calculated yield (from filtrate concentration) is 98.9%. Analysis by XRPD (FIG. 13B) showed no change in form and no loss in crystallinity. Analysis by PLM showed birefringent particles of rod-like morphology. Thermal analysis by TGA showed a single weight loss of 3.8% between ca. 90° C. and 160° C., corresponding approximately to 1 mole equivalent water (3.3%) and consistent with previous Form D material. Thermal analysis by DTA showed a broad endotherm, with onset ca.113.5° C. (peak ca. 135° C.), corresponding to the observed weight loss. KF coulometric titration measured the water content as approximately 3.4% (±0.5%), corresponding approximately to the weight loss observed by TG/DTA. Purity analysis by HPLC indicated a purity of 99.9%.

10% Form D Seed

Approximately 5 g of Form G material was slurried in 200 mL acetone:water (99:1%) and approximately 500 mg Form D seed crystals (un-micronized) (10% by mass) were added to the slurry. The slurry was stirred at 50° C. for 3 hours and the conversion of Form G to Form D was monitored by XRPD with samples removed for analysis at the following time points: 1 hour, 2 hours, and 3 hours. The resultant solid material was then filtered and dried under vacuum. The yield was calculated from the resulting dry material.

TABLE 7

Results of XRPD monitoring of Form G to Form D conversion, using 10% Form D seed

| Analysis Time Point | Form |
|---|---|
| 1 hour | Form G |
| 2 hours | Form D with traces of Form G |
| 3 hours | Form D |

Stability of Form D

Figure 14:
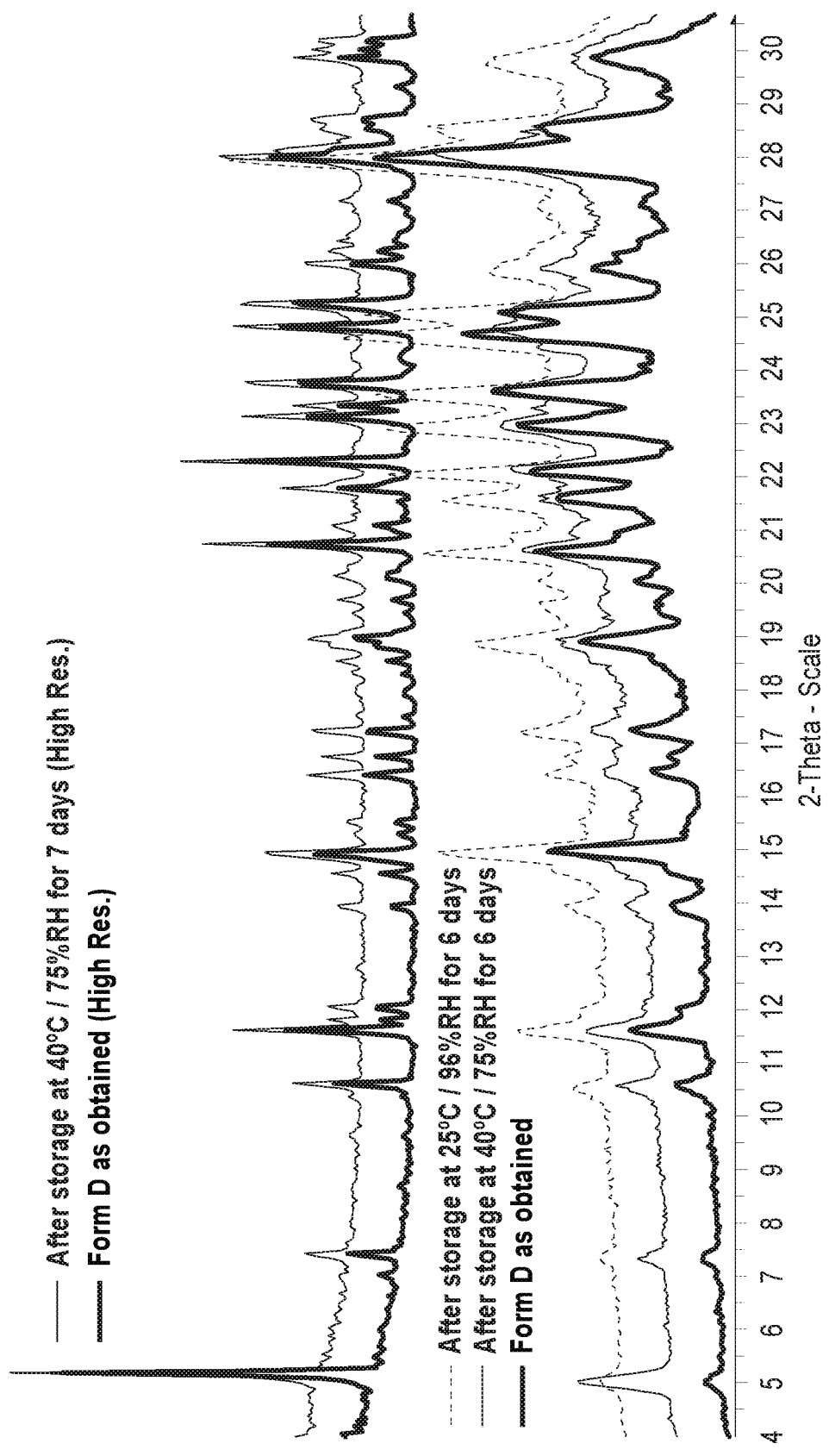
FIG. 14 sets forth X-ray powder diffraction patterns of Form D under various storage conditions as indicated.

Form D was stored in the humidity chamber at 40° C./75% RH and 25° C./96% RH for six days, and analyzed by XRPD (FIG. 14). No significant changes were observed in the crystalline pattern of either sample. Some amorphisation seemed to have occurred in the sample stored at 40° C./75% RH, but this was thought to be due to sample preparation rather than lack of stability in these conditions.

Hygroscopicity of Form D

Figure 15:
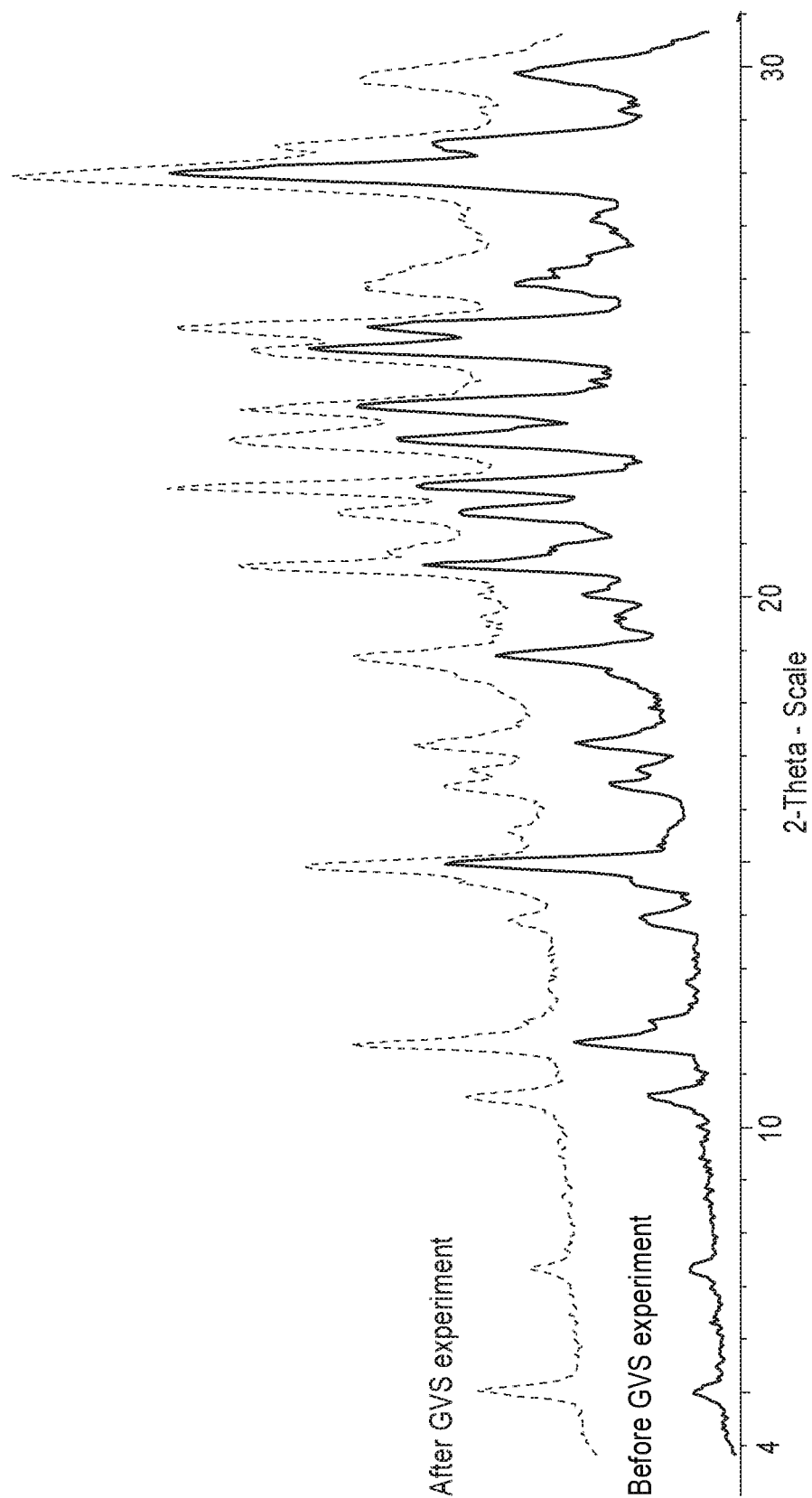
FIG. 15 sets forth X-ray powder diffraction patterns of Form D before and after GVS.

The hygroscopicity of Form D was assessed by GVS analysis. The experiment was started at 40% RH. The water uptake between 40% and 70% RH was lower than 0.1% w/w, while a significant increase in the water uptake was observed between 70% and 90% RH (1.6% w/w). However, during desorption cycle, the water content reversed back to the initial level. XRPD analysis before and after the GVS experiment showed that no significant changes had occurred in the crystalline pattern of the sample (FIG. 15).

Form D was successfully prepared on a 5 g scale using both 2% seed and 10% seed. The altered conditions enabled the time period required for conversion to be greatly reduced, as shown in Table 8. The Form D material converted from Form G in 4 days (original conditions) and Form D converted from Form G in 5.5 hours (altered conditions) were characterized as summarized in Table 9.

TABLE 8

Time period required for conversion of Form G to Form D under varying experimental conditions

| Experimental parameters | Seed Percent | Conversion Time |
|---|---|---|
| 50 mg/mL; acetone:water (98:2%); 50° C. | 0% | 4 days |
| 25 mg/mL; acetone:water (99:1%); 50° C. | 2% | 5.5 hours |
|  | 10% | 3 hours |

TABLE 9

Form D and Form G characterization summary

| Analysis | Form G (15 g) | Form D (5 g) 4 day | Form D (5 g) 5.5 hour |
|---|---|---|---|
| XRPD (crystallity) | High | High | High |
| PLM | Birefringent needles | Birefringent rods | Birefringent rods |
| TGA (weight loss) | (1.4%) 5.7% | 3.5% | 3.8% |
| DTA (endotherms) | 112.7° C. | 112.1° C. | 113.5° C. |
| KF (water content) | 5.7% | 3.6% | 3.4% |
| HPLC (Purity) | N/A | 99.9% | 99.9% |

Example 6: Preparation and Characterization of Form F 100 mg Scale Preparation

Approximately 100 mg of amorphous Compound A was slurried at 50° C. in 1.66 mL of acetonitrile and temperature cycled with continuous agitation in 4 hour cycles for a period of ca. 72 hours (slurries were held at 50° C. for 4 hours followed by a hold at ambient for 4 hours, the cooling/heating rates after the 4 hour hold periods was ca. 1° C./min). Solid material was then recovered and allowed to dry at ambient conditions prior to analysis.

600 mg Scale Preparation and Characterization

Approximately 600 mg of amorphous Compound A was kept in a 40° C./75% RH environment for 6 days. The material was found to have hardened to a solid lump, which was gently ground and analyzed by XRPD. It was then placed back into the 40° C./75% RH environment for a further 4 days in order to improve crystallinity.

XRPD of Form F was shown in FIG. 17: top panel (600 mg scale preparation) and bottom panel (100 mg scale preparation). Thermal analysis by TGA (FIG. 18) showed a weight loss of 3.2% between ca. 25° C. and ca. 110° C. corresponding approximately to 1 mole equivalent water (3.3%). A second loss of 1.7% was observed between 110° C. and 170° C. Thermal analysis by DTA (FIG. 18) showed an endotherm with onset 51.2° C. (peak ca. 72° C.), corresponding to the first weight loss. A second endotherm was observed with onset 133.9° C. (peak ca. 133° C.), corresponding to the second weight loss. KF coulometric titration measured the water content as approximately 4.6% (±0.5%), which corresponds approximately to the weight loss observed by TG/DTA. Ion chromatography indicated that the ratio of HCl to free base was approximately 1.7:1.

Figure 19:
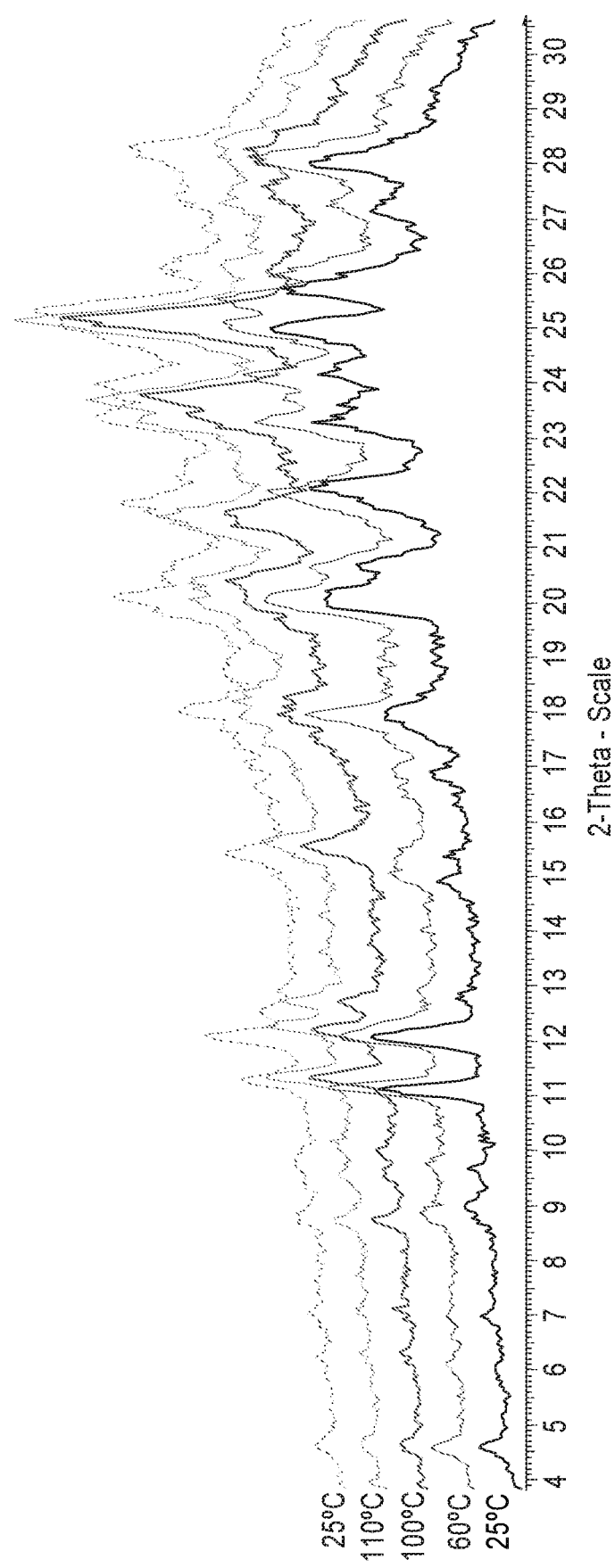
FIG. 19 sets forth X-ray powder diffraction patterns of Form F under different temperatures.

VT-XRPD experiments on Form F showed that the sample underwent changes in its crystalline structure upon heating. As shown in FIG. 19, the crystallinity of the sample decreased as it was heated from room temperature to 110° C. Some new diffraction peaks appeared. These changes were irreversible, and remained in the XRPD pattern after the sample was cooled back down to room temperature.

Example 7: Preparation and Characterization of Form G 600 mg Scale Preparation and Characterization Approximately 600 mg of amorphous Compound A was slurried at 50° C. in 7.14 mL 2-propanol:water ($W_A$=0.9) with continuous agitation for a period of ca. 72 hours, after which a further 800 µL solvent was added. The sample was replaced for slurrying at 50° C. with continuous agitation for a period of ca. 24 hours. Analysis by XRPD was carried out, and slurring at 50° C. was continued for another 48 hours. Solid material was then recovered and allowed to dry at ambient conditions prior to analysis by XRPD, KF, TG/DTA and IC.

As shown in FIG. 20A, Form G is highly crystalline after a total of 144 h (6 days) at 50° C. Thermal analysis by TGA (FIG. 21A) showed a gradual weight loss of 5.1% between ca. 25° C. and ca. 130° C., which is slightly greater than 1 mole equivalent of water (3.3%). Thermal analysis by DTA (FIG. 21A) showed a slight endotherm at 92° C., followed by a larger endotherm with onset 113.6° C. (peak ca. 126° C.), corresponding to the observed weight loss. Subsequent thermal analysis showed that the gradual loss in mass from room temperature was unaffected by drying, or that atmospheric water was taken up by the material when it was removed from drying conditions, suggesting that Form G may be hygroscopic at ambient humidity. KF coulometric titration measured the water content as approximately 5.0%% (±0.5%), which corresponds approximately to the weight loss observed by TG/DTA. Ion chromatography indicated that the ratio of HCl to free base was approximately 1.5:1.

Hot stage microscopy analysis between 25° C. and 250° C., where the material was observed to degrade by TG/DTA, showed no visible melting or dehydration events.

Additional thermal analysis by TGA of dried Form G material showed a gradual weight loss between ca. 25° C. and ca. 135° C., observed to be higher than 1 mole equivalent (3.3%).

material dried under ambient conditions (FIG. 21B): 5.29% material dried under vacuum (FIG. 21C): 5.41%

Additional thermal analysis by DTA showed a broad endotherm, corresponding to the weight loss:

material dried under ambient conditions (FIG. 21B): 112.4° C. (peak ca. 132° C.)

Material dried under vacuum (FIG. 21C): 110.8° C. (peak ca. 133° C.)

Figure 21A:
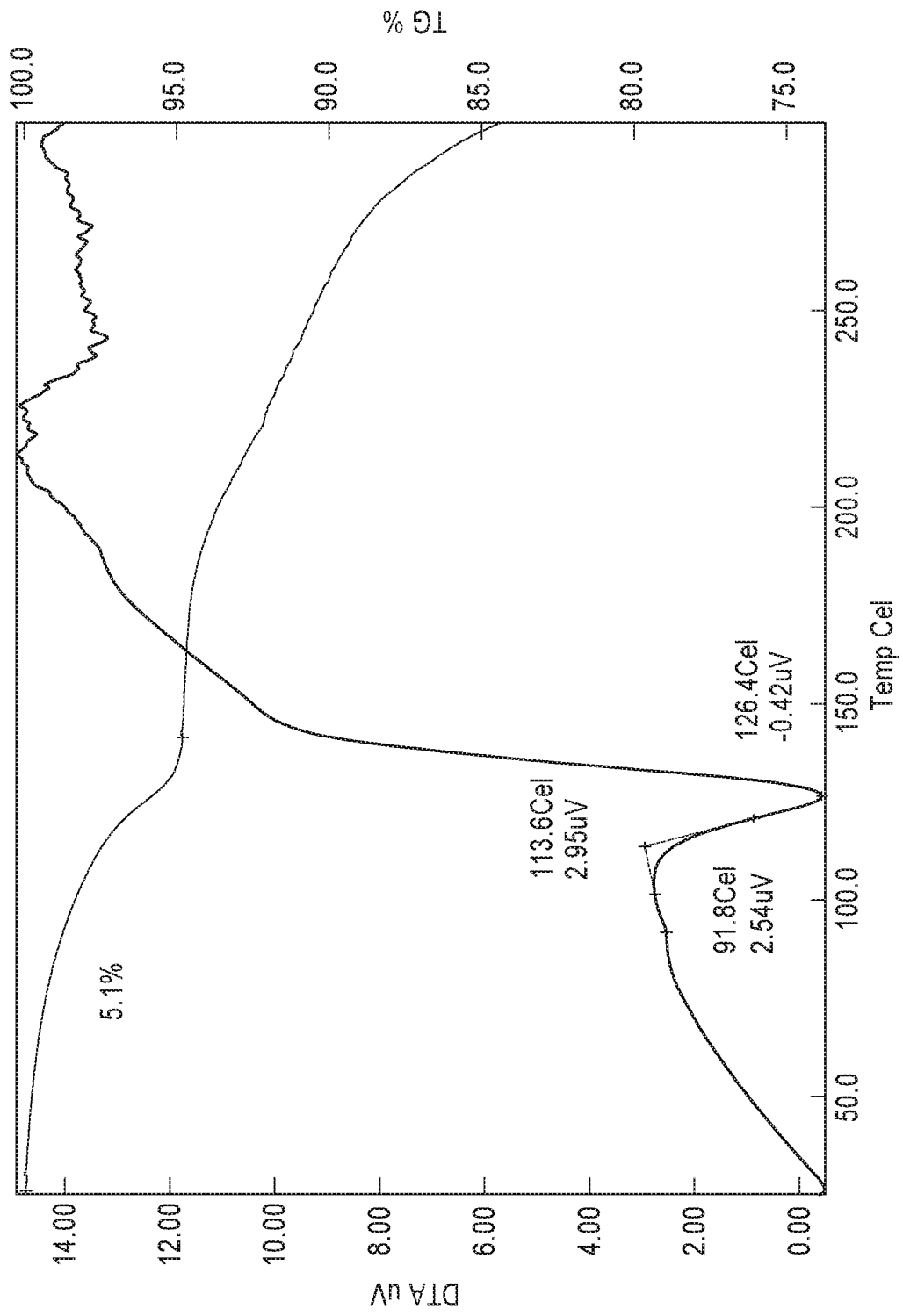
FIG. 21A sets forth thermal analysis by DTA and TG of Form G.
Figure 21B:
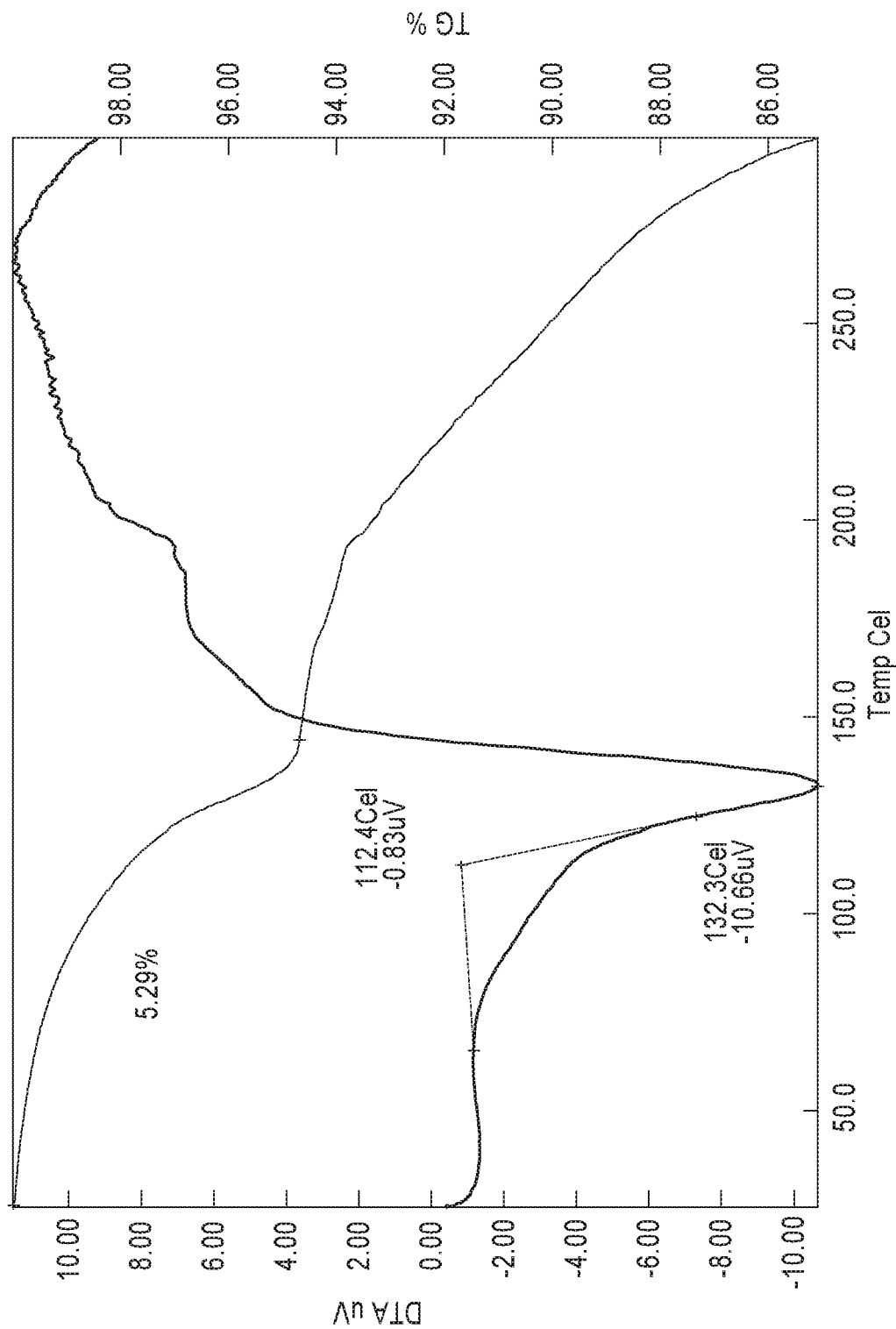
FIG. 21B sets forth thermal analysis by DTA and TG of Form G.
Figure 21C:
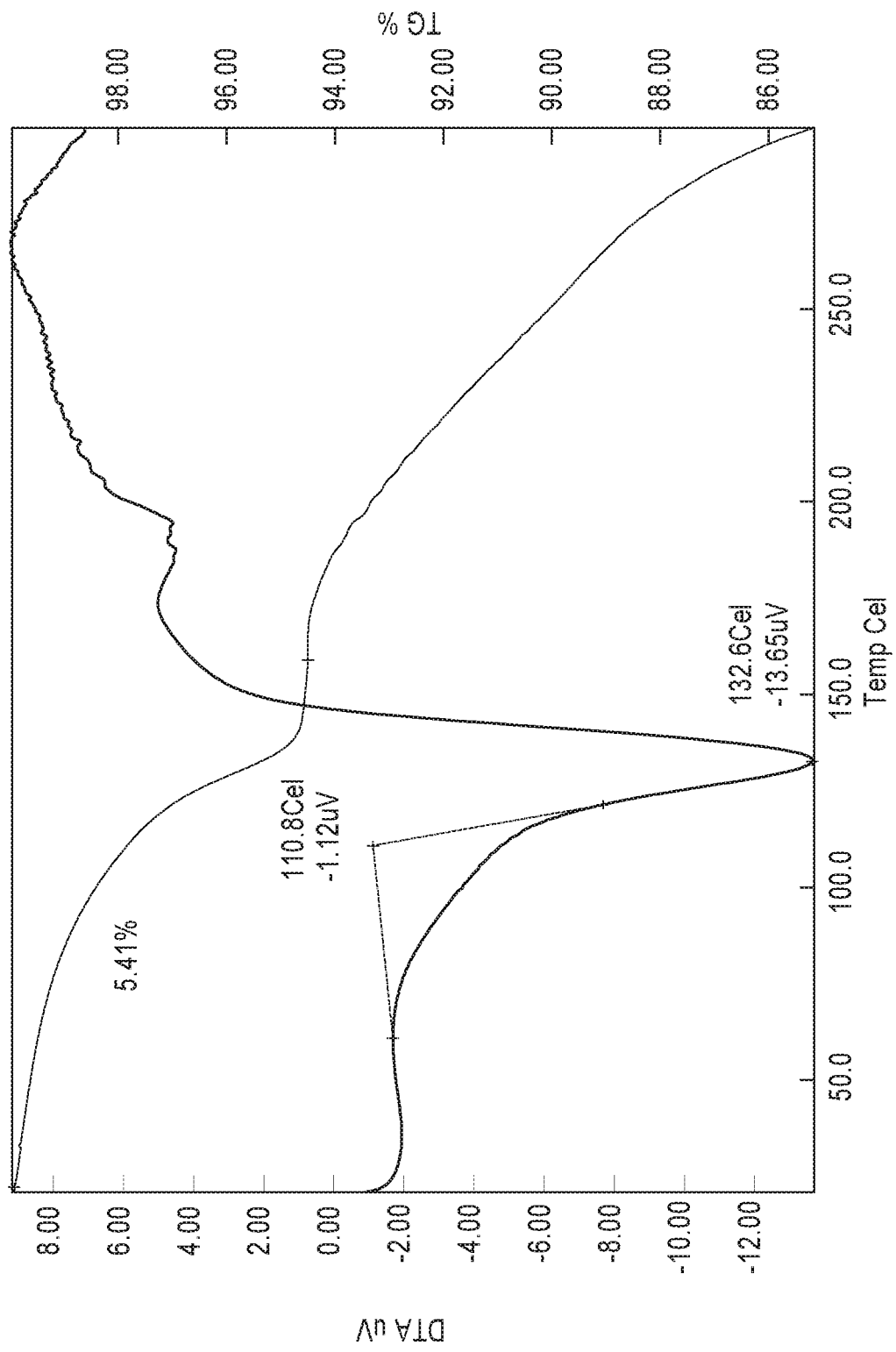
FIG. 21C sets forth thermal analysis by DTA and TG of Form G.
Figure 21D:
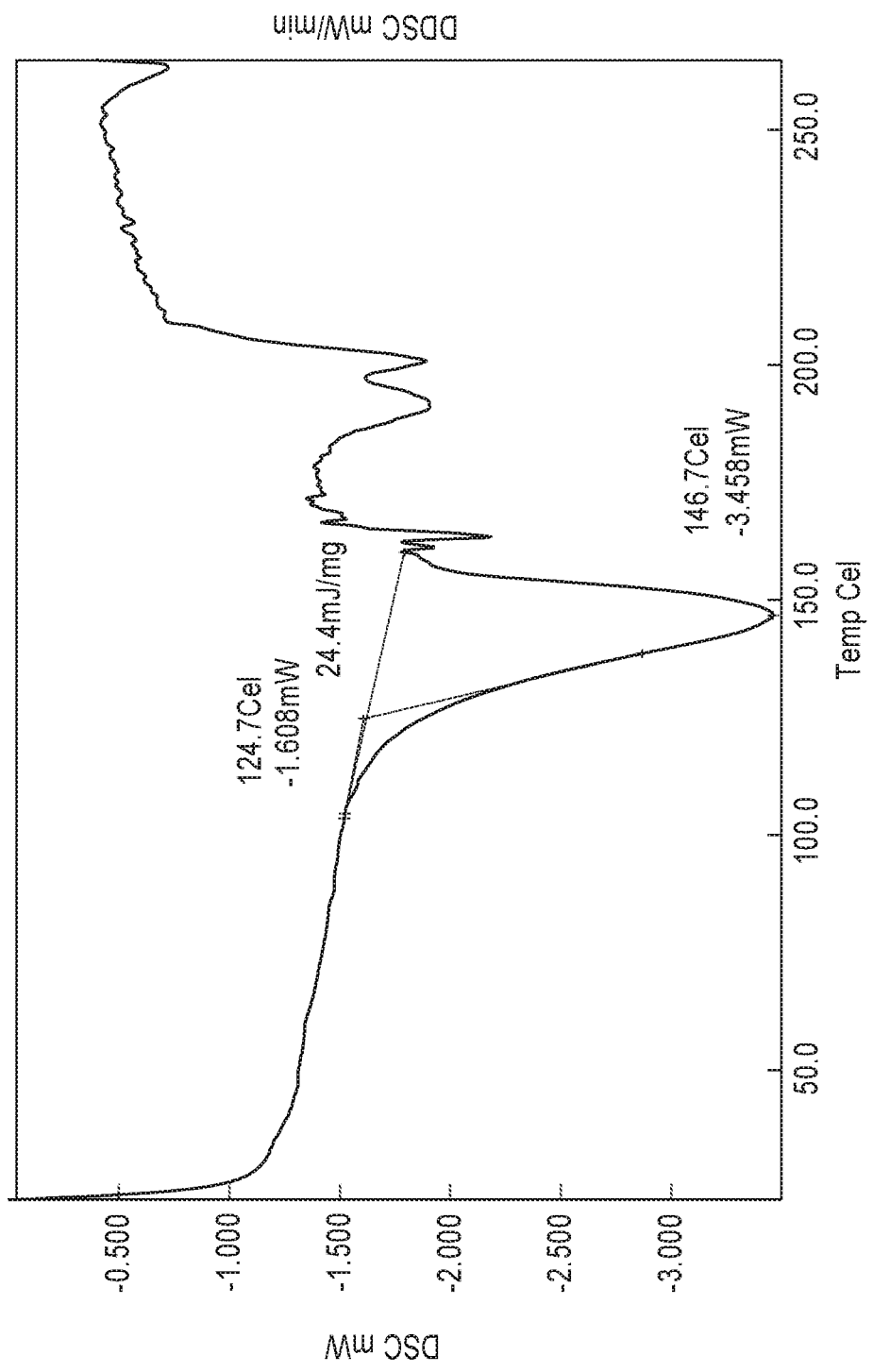
FIG. 21D sets forth analysis by DSC of Form G.

Analysis by DSC of Form G material dried under ambient conditions also showed a broad endotherm at 124.7° C. (peak ca. 146.7° C.) (FIG. 21D).

Analysis by DVS showed:

Sorption: 20 to 70% RH: 1.13% change in mass

Desorption: 70 to 0% RH: 1.32% change in mass

The increase in mass of 1.13% between 20 and 70% RH indicates that Form G is slightly hygroscopic. No dehydration/rehydration step was observed, indicating that Form G is likely a stable hydrate.

Figure 22:
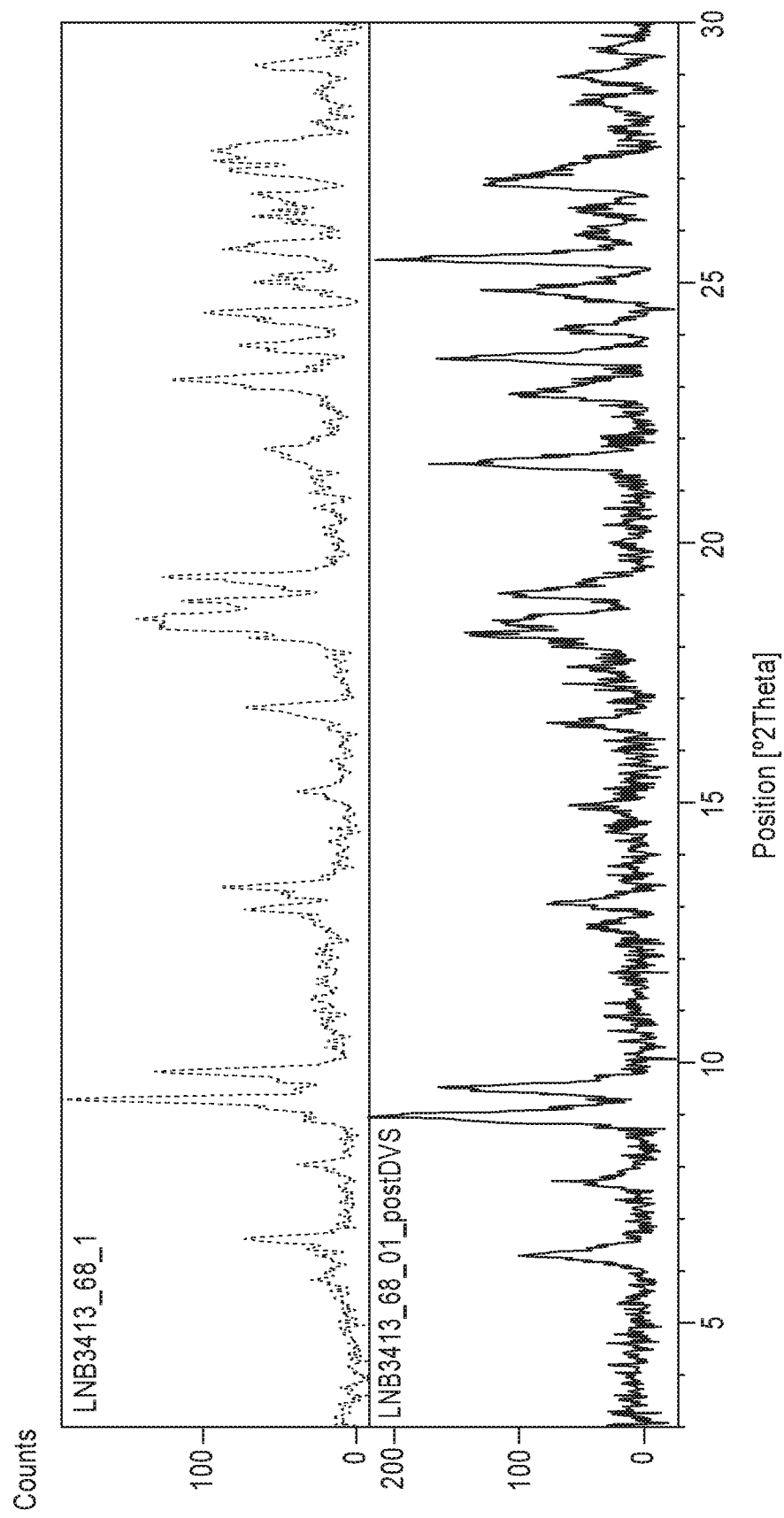
FIG. 22 sets forth X-ray powder diffraction patterns of Form G before (top panel) and after (bottom panel) DVS analysis.

Post DVS analysis by XRPD (FIG. 22) showed no change in polymorphic form.

Preparation of Form G and Characterization

Approximately 139.5 mg Compound A was dissolved in 2 mL of acetone:water (85:15%) at 50° C. The reaction mixture was then cooled to 20° C. over 1 hour. Crystallization was observed. A small portion of the slurry was filtered at 20° C. and concentration was determined by HPLC analysis; the isolated solid material was characterized by XRPD and PLM. Approximately 4 mL of acetone was then added slowly at 20° C. to achieve an acetone:water composition of 95:5%. A small portion of the slurry was filtered at 20° C. and concentration was determined by HPLC analysis; the isolated solid material was characterized by XRPD and PLM.

TABLE 10

Solubility and polymorphic form results

| Solvent System & Temperature | Solubility | Solid Form | Morphology |
|---|---|---|---|
| Acetone:water (85:15%) at 20° C. | 39.3 mg/mL | Form G | Needle-like |
| Acetone:water (95:5%) at 20° C. | 1.3 mg/mL | Form G | Needle-like |

TABLE 11

Summary of further characterization of Form G

| Analysis | Form G |
|---|---|
| XRPD (crystallity) | Flat plate and capillary: High |
| PLM | Birefringent needles |
| HSM | No observable events |
| TGA (weight loss) | 5.2% (5.4%)* |
| DTA (endotherms) | 112.4° C., peak ca. 132° C., (110.8° C., peak ca. 133° C.)* |

TABLE 11-continued

Summary of further characterization of Form G

| Analysis | Form G |
|---|---|
| DVS (hygroscopicity) | slightly hygroscopic (1.1% uptake), very stable hydrate |
| XRPD post DVS (form changes) | No change in form, improved crystallinity |
| KF (water content) | 4.9% |
| $^1$H-NMR | Spectrum consistent with structure, high water content |
| IR | For reference |
| IC (API:hydrochloride) | 1:2.15 |
| Thermodynamic aqueous solubility | 118.55 mg mL−1, (no change in Form, final pH: 1.1) |
| 1 Week Stability Study | High purity (>99.5%), no change in Form |

*TG/DTA carried out on material dried under vacuum 3 g Scale Preparation

Approximately 3 g of Compound A was weighed into a 20 mL flask. 3 mL 2-propanol:water (25:75%) was added and the resultant slurry was stirred at 50° C. for 4 hours. The slurry became very thick, and a further 2 mL solvent was added. After ca. 30 minutes, total dissolution was observed so the temperature was reduced to 40° C. and further to RT overnight. The slurry became very thick, and a further 1 mL solvent was added and the slurry re-heated to 40° C. After 1 hour, XRPD analysis was carried out and the temperature reduced to 30° C. After 1.5 hours a large amount of material was observed to have precipitated and final XRPD analysis was carried out. The resultant solid material was filtered, washed with 2-propanol:water (50:50%) and dried under vacuum for ca.17 hours.

7 g Scale Preparation

Approximately 7 g of Compound A was weighed into a 20 mL flask. 12 mL 2-propanol:water (25:75%) was added and the resultant slurry was stirred at 50° C. for ca. 3 hours. A further 1 mL solvent was added and the slurry heated to 60° C. until dissolution was observed. The temperature was reduced to 30° C. and the slurry stirred for 1 hour before cooling first to room temperature and then 5° C. XRPD analysis of the resultant solid material was carried out, and the material was filtered and dried under vacuum for ca. 72 hours.

15 g Scale Preparation and Characterization

Approximately 15 g of Compound A was weighed into a 100 mL flask and 30 mL 2-propanol:water (25:75%) was added at the following temperatures:

17 mL solvent was added at RT (ca. 22° C.)
13 mL solvent was added at 40° C.

The resultant slurry was stirred at 40° C. overnight, followed by stirring at RT for a further ca. 5.5 hours. The resultant solid material was isolated by filtration and washed with 2-propanol:water (50:50%). The filter cake was then dried under ambient conditions overnight and under vacuum for a further 27 hours. The yield was calculated from the resulting dry material.

Analysis by XRPD (FIG. 20B) before and after drying showed highly crystalline Form G. Analysis by PLM showed that Form G consists of small birefringent needles. Thermal analysis by TG showed an initial weight loss of 1.44%, likely due to unbound water or solvent, followed by a second gradual weight loss of 5.71% between ca. 40° C. and ca. 150° C., which is slightly higher than the previously observed TG/DT analysis of Form G and is likely due to unbound water/solvent (1 mole equivalent water=3.3%). Thermal analysis by DT showed a large, broad endotherm at onset ca.112.7° C. (peak ca. 131° C.), corresponding to the second weight loss observed by TGA. Analysis by KF titration indicated a water percentage of 5.7% (±0.5%), which corresponds to the loss in mass observed by TG/DTA.

Stability of Form G

Figure 23:
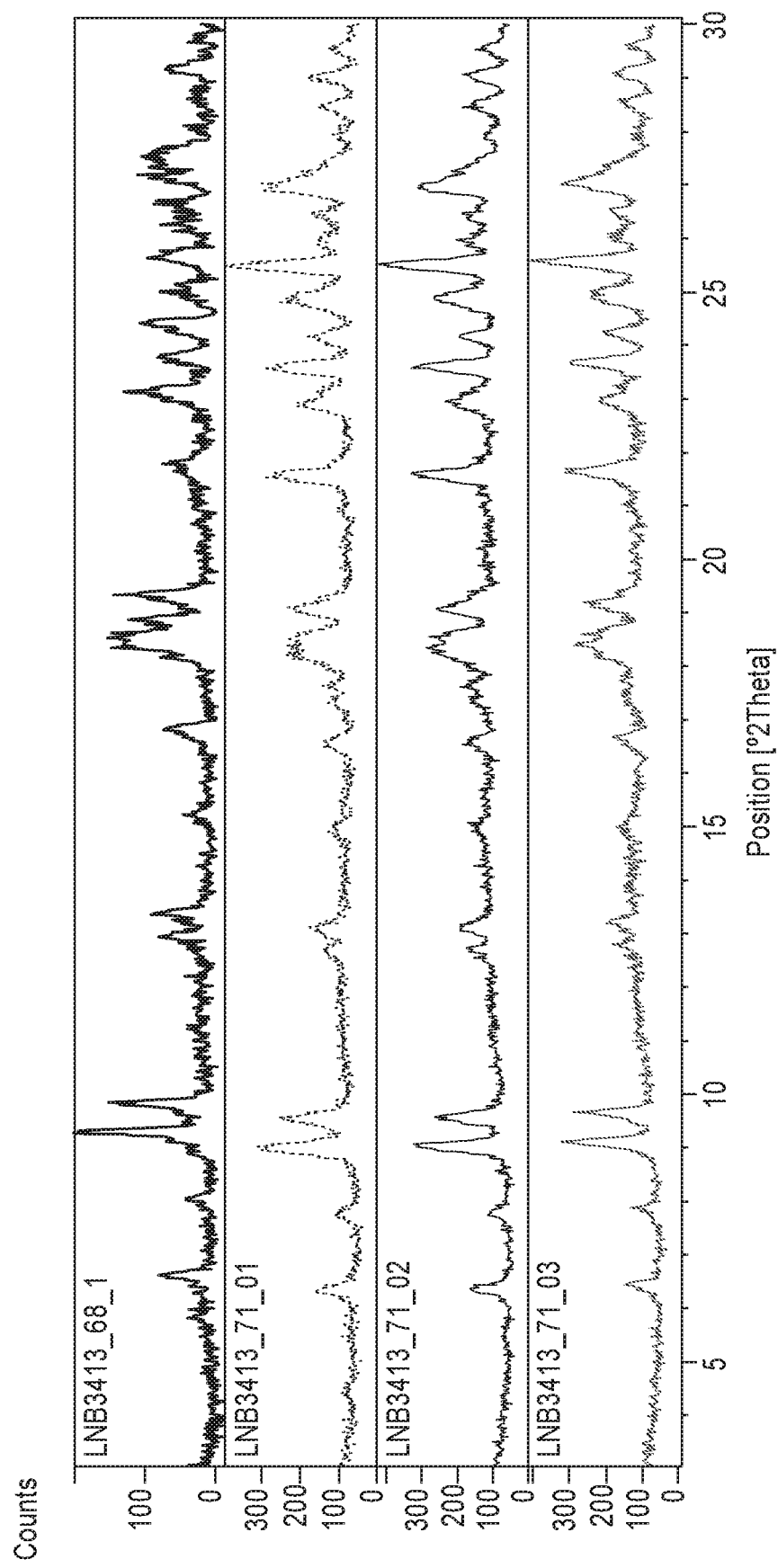
FIG. 23 sets forth X-ray powder diffraction patterns of Form G before (top panel), and after storage at 40° C. and 75% RH (second row from the top), at 40° C. (third row from the top), and 60° C. (bottom panel).

Form G was stored in the humidity chamber at 40° C./75% RH, 40° C. and 60° C. for 1 week, and analyzed by XRPD (FIG. 23) and HPLC. No changes in polymorphic form and purity of the resulting material were observed.

40° C./75% RH: 99.6%
40° C.: 99.7%
60° C.: 99.6%

Thermodynamic Aqueous Solubility of Form G

Approximately 100 mg Form G material was slurried in ca. 1 mL deionised water, with continuous agitation for a period of 24 hours. The pH of the deionised water used and the final pH of the filtered solution were measured. Thermodynamic aqueous solubility determination was carried out by HPLC analysis with post XRPD analysis on the remaining solid material.

Thermodynamic solubility of Form G in water was measured by HPLC analysis:

118.55 mg/mL

Figure 24:
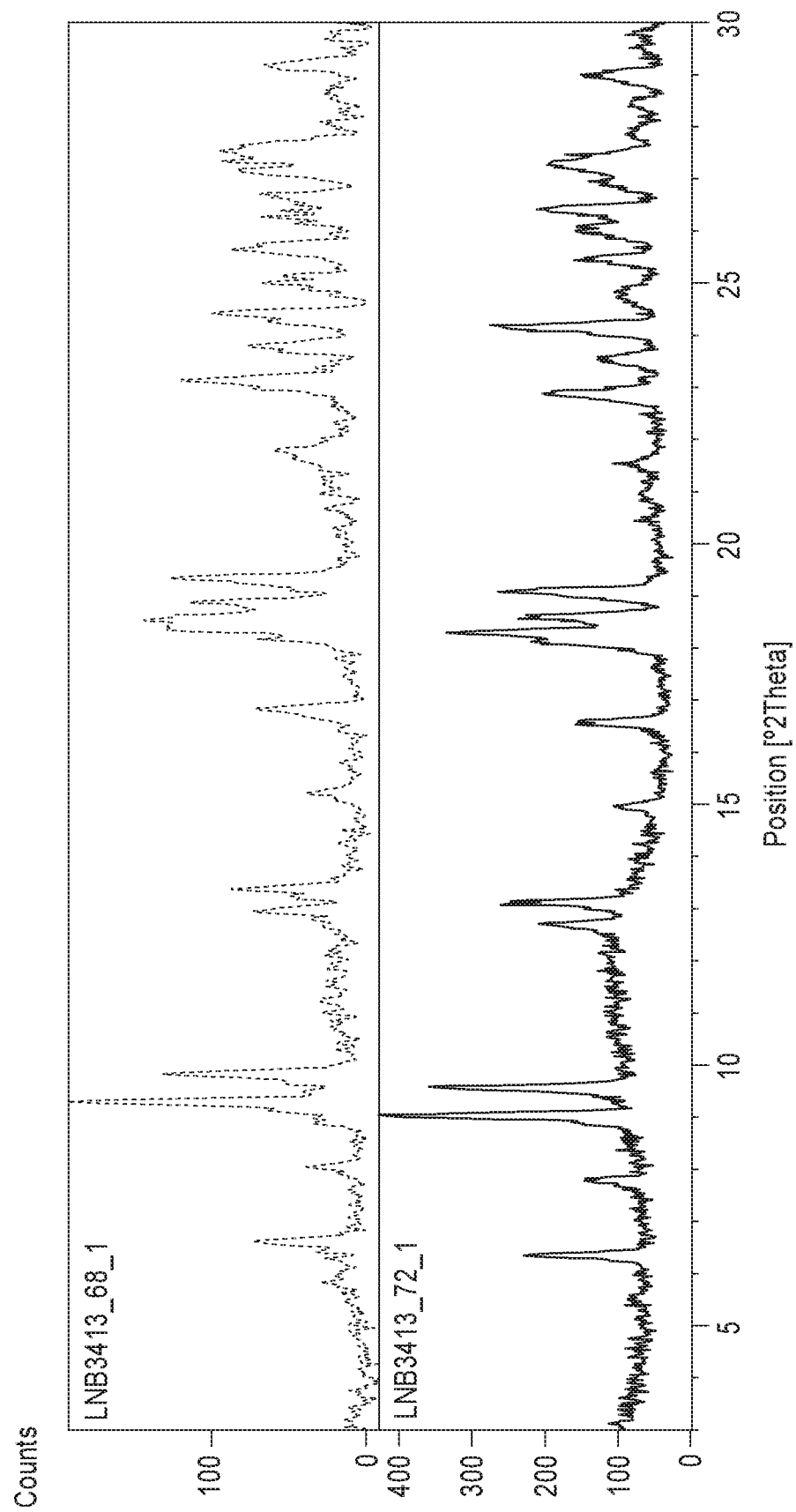
FIG. 24 sets forth X-ray powder diffraction patterns of Form G before (top panel) and after (bottom panel) thermodynamic aqueous solubility determination.

XRPD (FIG. 24) showed no change in form and a slight increase in crystallinity.

Changes in pH resulting from dissolution of the Bis-HCl salt were as follows:

Deionised water (dissolution medium): pH 6.4 (±pH 0.1)
Resultant solution (25 h stirring at RT): pH 1.1 (±pH 0.1)

Example 8: Preparation and Characterization of Form B

Figure 26:
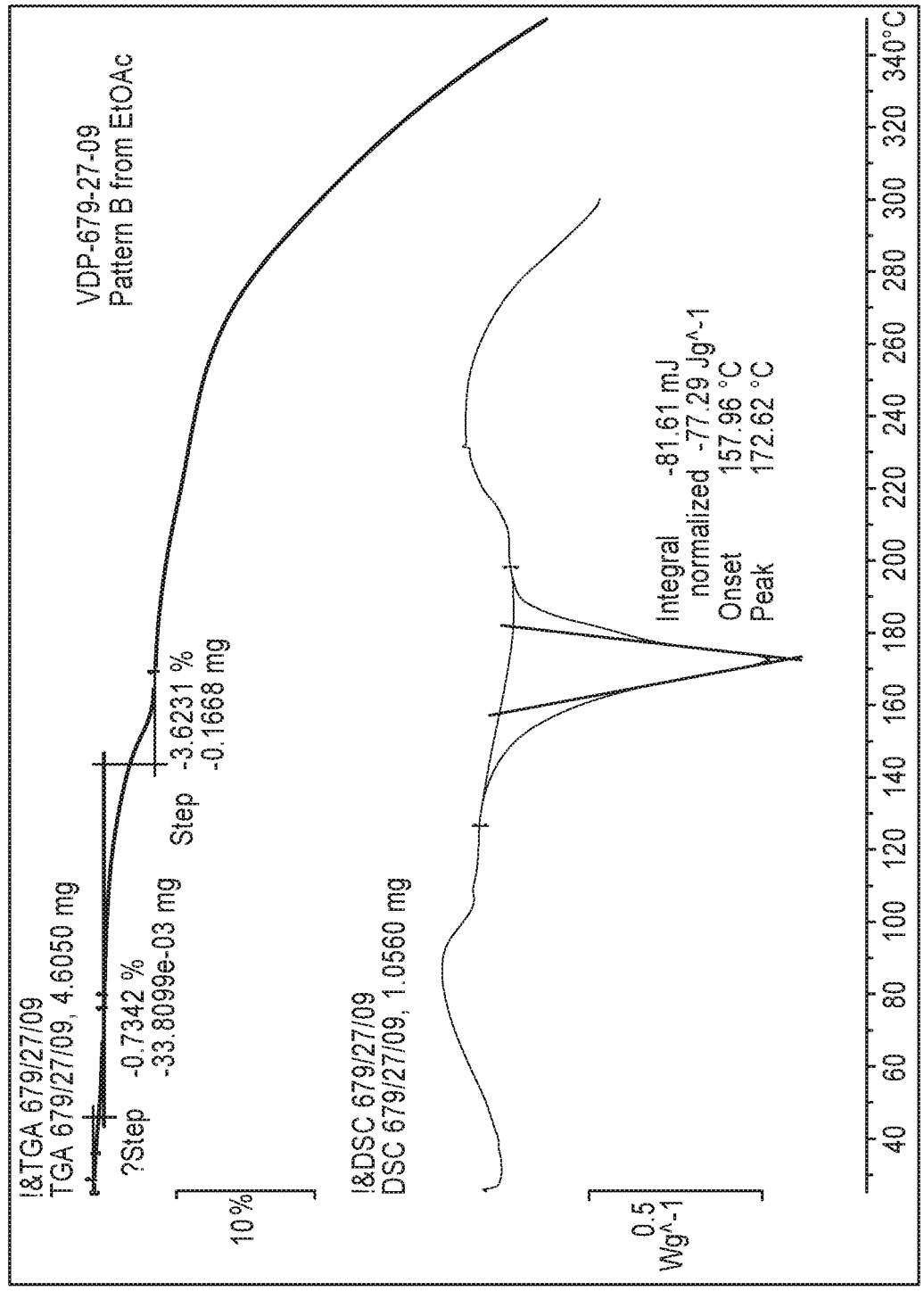
FIG. 26 sets forth thermal analysis by DSC and TG of the Form B solid form of Compound A.

Form B was obtained as a partially crystalline solid by maturation in a range of solvents, starting either from Form A or amorphous Compound A. The most crystalline Form B pattern was obtained from EtOAc. XRPD of Form B is show in FIG. 25. Thermal analysis by DSC and TGA showed a weight loss (0.7% w/w) at low temperature, which may be due to the presence of unbound solvent (FIG. 26). A second weight loss was observed at 80–100° C. (3.6% w/w) which probably corresponded to solvent bound to the crystalline structure (FIG. 26). No residual organic solvent was observed in the $^1$H-NMR spectrum, confirming that the solvent is water. Degradation of the material occurred soon after the solvent was lost. The DSC thermogram showed several events at low temperature related to the initial weight loss, and a more significant endotherm (onset at 158° C.), triggered by the water being lost from the crystal (FIG. 26). In addition, VT-XRPD experiments were performed between room temperature and 100° C. (to prevent the loss of solvent from the crystalline structure) to assess whether the crystallinity of the Form B improved with heating. However, no significant changes were observed in the crystalline pattern as the sample was heated.

Example 9: Single Crystal X-Ray Structure of Compound A

The single crystal X-ray structure of Compound A monohydrate was determined from crystals grown by recrystallization from an oil, obtained by slow evaporation in NMP. The structure is monoclinic, space group P2$_1$, with two independent molecules of Compound A and two independent molecules of water of hydration in the asymmetric unit related by a pseudo center of symmetry. The absolute stereochemistry was determined as R at C7A and C7B, molecule A and B respectively, from consideration of the Flack parameter which was determined to be 0.006(12).

TABLE 12

Sample and crystal data.

| | |
|---|---|
| Identification code | PHX-10-035 |
| Compound number | VDP-679-14-18 |
| Project/Program/F.S. | P1585 |
| Chemist's lab book | VDP-679-14-18 |
| X-ray lab book | PHX-10-035 |
| Crystallization lab book | VDP-679-14-18 |
| Crystallization solvents | NMP |
| Crystallization method | Recrystallization from an oil |
| Empirical formula | $C_{29}H_{33}Cl_2FN_4O_2$ |
| Formula weight | 559.49 |
| Temperature | 100(1) K. |
| Wavelength | 1.5418 Å |
| Crystal size | 0.20 × 0.08 × 0.02 mm |
| Crystal habit | Yellow Plate |
| Crystal system | Monoclinic |
| Space group | P2$_1$ |
| Unit cell dimensions | a = 9.70320(10) Å    α = 90° |
| | b = 16.5616(3) Å    β = 92.322(2)° |
| | c = 16.8628(3) Å    γ = 90° |
| Volume | 2707.64(7) Å$^3$ |
| Z | 4 |
| Density (calculated) | 1.373 Mg/m$^3$ |
| Absorption coefficient | 2.498 mm$^{-1}$ |
| F(000) | 1176 |

TABLE 13

Data collection and structure refinement.

| | |
|---|---|
| Diffractometer | SuperNova, Dual, Cu at zero, Atlas |
| Radiation source | SuperNova (Cu) X-ray Source, CuKα |
| Data collection method | phi and omega scans |
| Theta range for data collection | 3.74 to 62.20° |
| Index ranges | −11 ≤ h ≤ 10, −18 ≤ k ≤ 18, −16 ≤ l ≤ 19 |
| Reflections collected | 15483 |
| Independent reflections | 8250 [R(int) = 0.0327] |
| Coverage of independent reflections | 99.1% |
| Variation in check reflections | N/A |
| Absorption correction | Semi-empirical from equivalents |
| Max. and min. transmission | 1.00000 and 0.83454 |
| Structure solution technique | direct |
| Structure solution program | Bruker SHELXTL |
| Refinement technique | Full-matrix least-squares on F$^2$ |
| Refinement program | Bruker SHELXTL |
| Function minimized | $\Sigma w(Fo^2-Fc^2)^2$ |
| Data/restraints/parameters | 8250/1/731 |
| Goodness-of-fit on F$^2$ | 1.007 |
| D/s$_{max}$ | 0.000 |
| Final R indices | |
| 7179 data; I > 2σ(I) | R1 = 0.0381, wR2 = 0.0967 |
| all data | R1 = 0.0490, wR2 = 0.1080 |
| Weighting scheme | calc w = 1/[σ$^2$ (Fo$^2$) + ( 0.00730P)$^2$ + 0.2000P] where P = (F$_o^2$ + 2F$_c^2$)/3 |

TABLE 13-continued

Data collection and structure refinement.

| | |
|---|---|
| Absolute structure parameter | 0.006(12) |
| Largest diff. peak and hole | 0.268 and −0.310 e Å$^{-3}$ |
| Refinement summary: | |
| Ordered Non-H atoms, XYZ | Freely refining |
| Ordered Non-H atoms, U | Anisotropic |
| H atoms (on carbon), XYZ | Riding on parent atom |
| H atoms (on carbon), U | Isotropic |
| H atoms (on heteroatoms), XYZ | Freely refining |
| H atoms (on heteroatoms), U | Isotropic |
| Disordered atoms, OCC | Freely refining |
| Disordered atoms, XYZ | Freely refining |
| Disordered atoms, U | Anisotropic |

Figure 27:
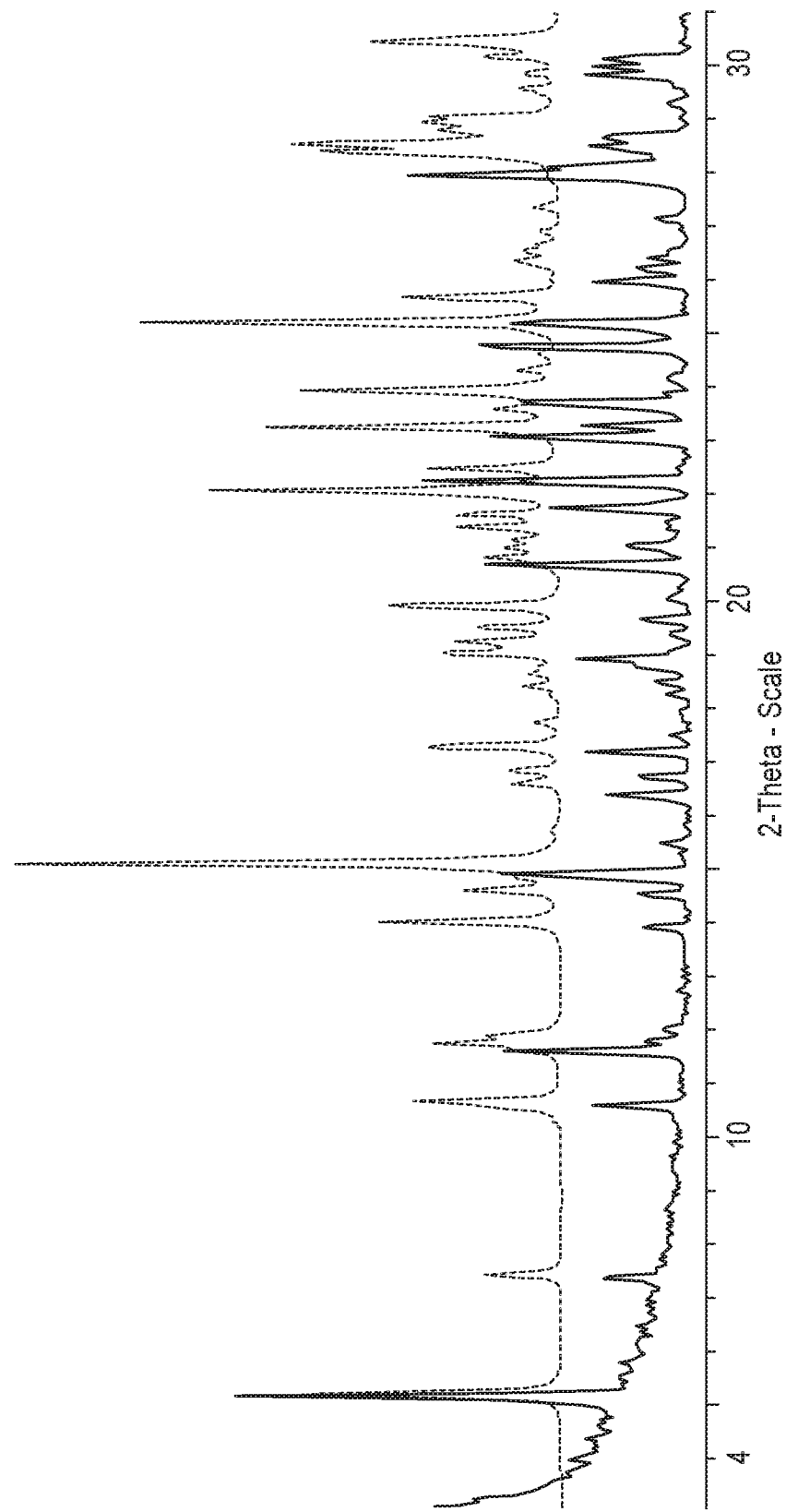
FIG. 27 sets forth X-ray powder diffraction patterns of a single crystal of Compound A (simulated, top) and of Form D (experimental, bottom).

As shown in FIG. 27, the simulated XRPD of the single crystal of Compound A is consistent with the XRPD of Form D.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method of making a polymorph of Compound A:

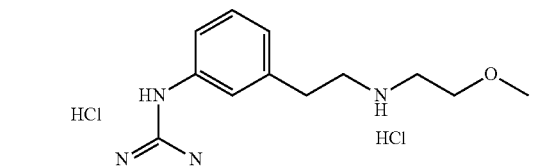

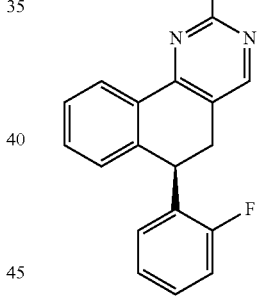

comprising:
step a) dissolving Compound A in a first solvent to form a solution;
step b) adding an anti-solvent to the solution to form a slurry; and
step c) cooling the slurry;
wherein the first solvent is selected from a mixture of acetone and water, 2-propanol and water, and acetonitrile and water, and wherein the anti-solvent is selected from acetone, 2-propanol, and acetonitrile,
wherein the polymorph is characterized by an X-ray powder diffraction pattern comprising peaks at approximately 14.9, 23.1, and 23.8 °2θ using Cu Kα radiation.

2. The method of claim 1, further comprising step d) isolating the polymorph of Compound A.

3. The method of claim 1, wherein the solution comprises water and in step b) the anti-solvent is added to decrease the percentage of water to between about 10% and about 5% in the solution.

4. The method of claim 1, wherein the solution comprises water and in step b) the anti-solvent is added to decrease the percentage of water to about 5% in the solution.

5. The method of claim 1, wherein the solution comprises water and after the addition of anti-solvent in step b) the percentage of water in the solution is about or less than 5%.

6. The method of claim 1, further comprising after step a) and before step b): step a0) heating the solution from step a).

7. The method of claim 6, wherein the solution is heated to a temperature of about 50° C.

8. The method of claim 1, wherein in step a) Compound A is dissolved in the first solvent at a temperature of at least 50° C.

9. The method of claim 1, wherein in step a) Compound A is dissolved in the first solvent at a temperature of about 50° C.

10. The method of claim 1, further comprising adding a seed polymorph of Compound A after the addition of the anti-solvent in step b), wherein the seed polymorph is characterized by an X-ray powder diffraction pattern comprising peaks at approximately 14.9, 23.1, and 23.8 °2θ using Cu Kα radiation; and/or
adding a seed polymorph of Compound A before the addition of the anti-solvent in step b), wherein the seed polymorph is characterized by an X-ray powder diffraction pattern comprising peaks at approximately 14.9, 23.1, and 23.8 °2θ using Cu Kα radiation.

11. The method of claim 1, further comprising step a2) adding a seed polymorph of Compound A before the addition of the anti-solvent in step b), wherein the seed polymorph is characterized by an X-ray powder diffraction pattern comprising peaks at approximately 14.9, 23.1, and 23.8 °2θ using Cu Kα radiation; and after step a2) and before step b), step a3): aging the slurry.

12. The method of claim 11, wherein the slurry is aged for 30 to 60 min.

13. The method of claim 10, wherein the slurry is cooled to a temperature of about 20° C.

14. The method of claim 10, further comprising one or more steps selected from the following: agitating the slurry and filtering and drying the slurry to produce a polymorph of Compound A.

15. The method of claim 1, wherein the polymorph of Compound A is characterized by an X-ray powder diffraction pattern comprising peaks at approximately 10.6, 14.9, 23.1, 23.8, and 24.8 °2θ using Cu Kα radiation.

16. The method of claim 1, wherein the polymorph of Compound A is characterized by an X-ray powder diffraction pattern comprising peaks at approximately 10.6, 11.6, 13.9, 14.9, 19.0, 21.8, 22.3, 23.1, 23.8, 24.8, 25.3, 28.1, 28.2, and 28.7 °2θ using Cu Kα radiation.

17. The method of claim 1, further comprising a step of formulating the polymorph of Compound A as a pharmaceutical composition with at least one pharmaceutically acceptable excipient or carrier.

18. The method of claim 1, wherein the first solvent is acetone and water and the anti-solvent is acetone.

19. The method of claim 18, further comprising step d) isolating the polymorph of Compound A.

20. The method of claim 18, wherein step b) comprises adding acetone to the solution in an amount to achieve a vol/vol ratio of acetone:water of about 95:5.

21. The method of claim 18, wherein in step b) the anti-solvent is added to decrease the percentage of water to between about 10% and about 5% in the solution.

22. The method of claim 18, wherein in step b) the anti-solvent is added to decrease the percentage of water to about 5% in the solution.

23. The method of claim 18, wherein in step b) the percentage of water in the solution is about or less than 5%.

24. The method of claim 18, wherein the vol/vol ratio of acetone:water in step a) is 85:15.

25. The method of claim 18, further comprising after step a) and before step b), step a1): adding acetone to achieve a vol/vol ratio of acetone:water of about 88.5:11.5.

26. The method of claim 18, further comprising after step a) and before step b): step a0) heating the solution from step a).

27. The method of claim 26, wherein the solution is heated to a temperature of about 50° C.

28. The method of claim 18, wherein in step a) Compound A is dissolved in the first solvent at a temperature of at least 50° C.

29. The method of claim 18, wherein in step a) Compound A is dissolved in the first solvent at a temperature of about 50° C.

30. The method of claim 18, further comprising adding a seed polymorph of Compound A after the addition of the anti-solvent in step b), wherein the seed polymorph is characterized by an X-ray powder diffraction pattern comprising peaks at approximately 14.9, 23.1, and 23.8 °2θ using Cu Kα radiation; and/or adding a seed polymorph of Compound A before the addition of the anti-solvent in step b), wherein the seed polymorph is characterized by an X-ray powder diffraction pattern comprising peaks at approximately 14.9, 23.1, and 23.8 °2θ using Cu Kα radiation.

31. The method of claim 30, further comprising step a2) adding a seed polymorph of Compound A before the addition of the anti-solvent in step b), wherein the seed polymorph is characterized by an X-ray powder diffraction pattern comprising peaks at approximately 14.9, 23.1, and 23.8 °2θ using Cu Kα radiation; and after step a2) and before step b), step a3): aging the slurry.

32. The method of claim 31, wherein the slurry is aged for 30 to 60 min.

33. The method of claim 30, wherein the slurry is cooled to a temperature of about 20° C.

34. The method of claim 30, further comprising one or more steps selected from the following: agitating the slurry and filtering and drying the slurry to produce a polymorph of Compound A.

35. The method of claim 18, wherein the polymorph of Compound A is characterized by an X-ray powder diffraction pattern comprising peaks at approximately 10.6, 14.9, 23.1, 23.8, and 24.8 °2θ using Cu Kα radiation.

36. The method of claim 18, wherein the polymorph of Compound A is characterized by an X-ray powder diffraction pattern comprising peaks at approximately 10.6, 11.6, 13.9, 14.9, 19.0, 21.8, 22.3, 23.1, 23.8, 24.8, 25.3, 28.1, 28.2, and 28.7 °2θ using Cu Kα radiation.

37. The method of claim 18, further comprising a step of formulating the polymorph of Compound A as a pharmaceutical composition with at least one pharmaceutically acceptable excipient or carrier.

* * * * *